(12) United States Patent
Keasling et al.

(10) Patent No.: US 7,927,794 B2
(45) Date of Patent: Apr. 19, 2011

(54) METHODS FOR IDENTIFYING A BIOSYNTHETIC PATHWAY GENE PRODUCT

(75) Inventors: Jay D. Keasling, Berkeley, CA (US);
Jack D. Newman, Berkeley, CA (US);
Douglas J. Pitera, Oakland, CA (US);
Sydnor T. Withers, III, Richmond, CA (US); Keith Kinkead Reiling, San Francisco, CA (US); Vincent J. J. Martin, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 1139 days.

(21) Appl. No.: 10/573,796

(22) PCT Filed: Sep. 29, 2004

(86) PCT No.: PCT/US2004/032407
§ 371 (c)(1),
(2), (4) Date: Dec. 8, 2006

(87) PCT Pub. No.: WO2005/033287
PCT Pub. Date: Apr. 14, 2005

(65) Prior Publication Data
US 2007/0141574 A1    Jun. 21, 2007

Related U.S. Application Data

(60) Provisional application No. 60/507,220, filed on Sep. 29, 2003.

(51) Int. Cl.
*C12Q 1/68* (2006.01)
*C12N 15/64* (2006.01)
*C07H 21/04* (2006.01)

(52) U.S. Cl. ............ 435/6; 435/166; 435/468; 435/471; 536/23.2

(58) Field of Classification Search .................. None
See application file for complete search history.

(56) References Cited

U.S. PATENT DOCUMENTS

| 5,187,071 A | 2/1993 | Fischer et al. |
| 7,172,886 B2 | 2/2007 | Keasling et al. |
| 2003/0148416 A1 | 8/2003 | Berry et al. |
| 2003/0148479 A1 | 8/2003 | Keasling et al. |

FOREIGN PATENT DOCUMENTS
WO    WO0131043 A1    5/2001

OTHER PUBLICATIONS

Back and Chappell, "Identifying functional domains within terpene cyclases using a domain-swapping strategy" Prac. Natl. Acad. Sci. (1996), vol. 93, pp. 6841-6845.
Martin et al., "Engineering a mevalonate pathway in *Escherichia coli* for production of terpenoids" Nature Biotechnology (2003), vol. 21, No. 7, pp. 796-802.
Trapp and Croteau, "Genomic Organization of Plant Terpene Synthases and Molecular Evolutionary Implications" Genetics (2001), vol. 158, pp. 811-831.
Hamano, Y., et al. Cloning of a gene cluster encoding enzymes responsible for the mevalonate pathway from a terpenoid-antibiotic-producing streptomyces strain. Bioscience, Biotechnology, Biochemistry. 2001, vol. 65, No. 7, pp. 1627-1635.
Jackson, B., et al. Metabolic engineering to produce sesquiterpenes in yeast. Organic Letters. 2003, vol. 5, No. 10, pp. 1629-1632.
Paiva, N. An introduction to the biosynthesis of chemicals used in plant-microbe communication. Journal of Plant Growth Regulation. 2000, vol. 19, pp. 131-143.
Pitera, D., et al. Optimizing a heterologous mevalonate pathway for the production of terpenoids in *Escherichia coli*. Abstracts of the General Meeting of the American Society for Microbiology, the Society, Washington DC, US, 2004, vol. 104, pp. 471.
Polakowski, T., et al. Overexpression of a cytosolic hydroxymethylglutaryl-CoA reductase leads to squalene accumulation in yeast. Applied Microbiology and Biotechnology. 1998, vol. 49, pp. 66-71.
Wang, K., et al. Isoprenyl diphosphate synthases. Biochimica et Biophysica Acta. 2000, vol. 1529, pp. 33-48.

*Primary Examiner* — Nancy Vogel
(74) *Attorney, Agent, or Firm* — Paula A. Borden; Bozicevic, Field & Francis LLP

(57) ABSTRACT

The present invention provides isolated, genetically modified host cells, where a host cell is genetically modified with a nucleic acid that includes a nucleotide sequence encoding a biosynthetic pathway enzyme. Synthesis of the enzyme in the host cell results in conversion of a substrate for the enzyme into a biosynthetic pathway intermediate, which intermediate is produced in an amount effective to inhibit growth of the genetically modified host cell. The present invention further provides compositions and kits comprising a subject genetically modified host cell. Subject host cells are useful for identifying a gene product having activity in a biosynthetic pathway. The present invention further provides methods of identifying a gene product having activity in a biosynthetic pathway.

56 Claims, 13 Drawing Sheets

Mevalonate pathway

DXP pathway

```
                                T-1
GATTAAGGCATGCACCATGGCCCTGACCGAAGAGAAACCGATCCGCCCGATCGCTAACT
CTAATTCCGTACGTGGTACCGGGACTGGCTTCTCTTTGGCTAGGCGGGCTAGCGATTGA
         B-1                                       B-2

T-2                                              T-3
TCCCGCCGTCTATCTGGGGTGACCAGTTCCTGATCTACGAAAAGCAGGTTGAGCAGGGT
AGGGCGGCAGATAGACCCCACTGGTCAAGGACTAGATGCTTTTCGTCCAACTCGTCCCA
                        B-3
                            T-4
GTTGAACAGATCGTAAACGACCTGAAGAAAGAAGTTCGTCAGCTGCTGAAAGAAGCTCT
CAACTTGTCTAGCATTTGCTGGACTTCTTTCTTCAAGCAGTCGACGACTTTCTTCGAGA
B-4                                                   B-5
T-5                                       T-6
GGACATCCCGATGAAACACGCTAACCTGCTGAAACTGATCGACGAGATCCAGCGTCTGG
CCTGTAGGGCTACTTTGTGCGATTGGACGACTTTGACTAGCTGCTCTAGGTCGCAGACC
                          B-6
                         T-7
GTATCCCGTACCACTTCGAACGCGAAATCGACCACGCACTGCAGTGCATCTACGAAACC
CATAGGGCATGGTGAAGCTTGCGCTTTAGCTGGTGCGTGACGTCACGTAGATGCTTTGG
B-7                                                   B-8
     T-8                                      T-9
TACGGCGACAACTGGAACGGCGACCGTTCTTCTCTGTGGTTTCGTCTGATGCGTAAACA
ATGCCGCTGTTGACCTTGCCGCTGGCAAGAAGAGACACCAAAGCAGACTACGCATTTGT
                       B-9
                      T-10
GGGCTACTACGTTACCTGTGACGTTTTTAACAACTACAAGGACAAGAACGGTGCTTTCA
CCCGATGATGCAATGGACACTGCAAAAATTGTTGATGTTCCTGTTCTTGCCACGAAAGT
           B-10                                    B-11
T-11                                          T-12
AACAGTCTCTGGCTAACGACGTTGAAGCCTGCTGGAACTGTACGAAGCGACCTCCATG
TTGTCAGAGACCGATTGCTGCAACTTCCGGACGACCTTGACATGCTTCGCTGGAGGTAC
                           B-12
                         T-13
CGTGTACCGGGTGAAATCATCCTGGAGGACGCGCTGGGTTTCACCCGTTCTCGTCTGTC
GCACATGGCCCACTTTAGTAGGACCTCCTGCGCGACCCAAAGTGGGCAAGAGCAGACAG
     B-13                                            B-14

T-14                                         T-15
CATTATGACTAAAGACGCTTTCTCTACTAACCCGGCTCTGTTCACCGAAATCCAGCGTG
GTAATACTGATTTCTGCGAAAGAGATGATTGGGCCGAGACAAGTGGCTTTAGGTCGCAC
```

FIG. 12A

```
                    T-16
CTCTGAAACAG|CCGCTGTGGAAACGTCTGCCGCGTATCGAAGCAGCACAG|TACATTCCG
GAGACTTTGTCGGCGACACCTTTGCAGACG|GCGCATAGCTTCGTCGTGTCATGTAAGGC
         B-16                                          B-17
         T-17                                          T-18
TTTTACCAGCAGCAGGACTCTCACAACAAG|ACCCTGCTGAAACTGGCTAAGCTGGAATT
AAAATGGTCGTCGT|CCTGAGAGTGTTGTTCTGGGACGACTTTGACCGATT|CGACCTTAA
                              B-18
                              T-19
CAACCTGCTGC|AGTCTCTGCACAAAGAAGAACTGTCTCACGTTTGTAAGTG|GTGGAAGG
GTTGGACGACGTCAGAGACGTGTTTCTT|CTTGACAGAGTGCAAACATTCACCACCTTCC
         B-19                                          B-20
         T-20                                          T-21
CATTTGACATCAAGAAAAACGCGCCGTGCCTG|CGTGACCGTATCGTTGAATGTTACTTC
GTAAACTGTA|GTTCTTTTTGCGCGGCACGGACGCACTGGCATAGCAACTTA|CAATGAAG
                              B-21
                              T-22
TGGGGTCTGGGTTC|TGGTTATGAACCACAGTACTCCCGTGCACGTGTGTTCTTC|ACTAA
ACCCCAGACCCAAGACCAATACTTGGTGTCATGA|GGGCACGTGCACACAAGAAGTGATT
         B-22                                          B-23
         T-23                                          T-24
AGCTGTAGCTGTTATCACCCTGATCGATGACACTTAC|GATGCTTACGGCACCTACGAAG
TCGACATCGACAATA|GTGGGACTAGCTACTGTGAATGCTACGAATGCCGTGGATG|CTTC
                              B-24
                              T-25
AACTGAAGATCTTTACTG|AAGCTGTAGAACGCTGGTCTATCACTTGCCTGGACACTC|TG
TTGACTTCTAGAAATGACTTCGACATCTTGCGACCA|GATAGTGAACGGACCTGTGAGAC
         B-25                                          B-26
         T-26                                          T-27
CCGGAGTACATGAAACCGATCTACAAACTGTTCATGG|ATACCTACACCGAAATGGAGGA
GGCCTCATGTACTTTGG|CTAGATGTTTGACAAGTACCTATGGATGTGGCTTTACCTC|CT
                              B-27
                              T-28
ATTCCTGGCAAAAGAAGG|CCGTACCGACCTGTTCAACTGCGGTAAAGAGTTTGTTAAAG
TAAGGACCGTTTTCTTCCGGCATGGCTGGACAAGTTGA|CGCCATTTCTCAAACAATTTC
         B-28                                          B-29
                              T-29
AATTCGTACGTAACCTGATGGTTGAAGCTAAATGGGCTAAC|GAAGGCCATATCCCGACT
TTAAGCATGCATTGGACTAC|CAACTTCGATTTACCCGATTGCTTCCGGTATAGGGCTGA
                                                       B-30
T-30                                          T-31
ACCGAAGAACATGACCCGGTTG|TTATCATCACCGGCGGTGCAAACCTGCTGACCACCAC
T|GGCTTCTTGTACTGGGCCAACAATAGTAGTGGCCGCCAC|GTTTGGACGACTGGTGGTG
                              B-31
```

FIG. 12B

```
                              T-32
TTG CTATCTGGGTATGTCCGACATCTTTACCAAGGAATCTGTT G AATGGGCTGTTTCTG
AAC GATAGACCCATACAGGCT GTAGAAATGGTTCCTTAGACAA CTTACCCGACAAAGAC
B-32                                                      B-33
T-33                                                      T-34
CACCGCCGCTGTTCCGTTACTCCGG TATTCTGGGTCGTCGTCTGAACGACCTGATGACC
GTG GCGGCGACAAGGCAATGAGGCCATAAGACCCAGCAGCAGA CTTGCTGGACTACTGG
                    B-34
                    T-35
CACAAAG CAGAGCAGGAACGTAAACACTCTTCCTCCTCTCTGGAATC CTACATGAAGGA
GTGTTTCGTCTCGTCCTTGCATTT GTGAGAAGGAGGAGAGACCTTAGGATGTACTTCCT
       B-35                                       B-36
            T-36                                       T-37
ATATAACGTTAACGAGGAGTACGCACAG ACTCTGATCTATAAAGAAGTTGAAGACGTAT
TATATT GCAATTGCTCCTCATGCGTGTCTGAGACTAGATATT T CTTCAACTTCTGCATA
                          B-37
                          T-38
GGAAAGAC ATCAACCGTGAATACCTGACTACTAAAAACATCCCGCGCC CGCTGCTGATG
CCTTTCTGTAGTTGGCACTTATGGACT GATGATTTTTGTAGGGCGCGGGCGACGACTAC
        B-38                                      B-39
             T-39                                       T-40
GCAGTAATCTACCTGTGCCAGTTCCTGG AAGTACAGTACGCTGGTAAAGATAACTTCAC
CGTCATTA GATGGACACGGTCAAGGACCTTCATGTCATGCGACCATTT CTATTGAAGTG
                           B-40
                           T-41
TCGCATGG CGACGAATACAAACACCTGATCAAATCCCTGCTGGTTTAC CCGATGTCCA
AGCGTACCCGCTGCTTATGTTTGTGGA CTAGTTTAGGGACGACCAAATGGGCTACAGGT
       B-41                                            B-stop
T-stop
TCTGATCCCGGGATTAGAT  SEQ ID NO: 23
AGACTAGGGCCCTAATCTA  SEQ ID NO: 24
```

FIG. 12C

SEQUENCE LISTING

<160> NUMBER OF SEQ ID NOS: 37

<210> SEQ ID NO 1
<211> LENGTH: 44
<212> TYPE: DNA
<213> ORGANISM: Artificial Sequence
<220> FEATURE:
<223> OTHER INFORMATION: primer

<400> SEQUENCE: 1
gatctgcagt aggaggaatt aaccatgcat taccgttctt aact                 44

<210> SEQ ID NO 2
<211> LENGTH: 33
<212> TYPE: DNA

<213> ORGANISM: Artificial Sequence
<220> FEATURE:
<223> OTHER INFORMATION: primer

<400> SEQUENCE: 2
ttgatctgcc tcctatgaag tccatggtaa att                                    33

<210> SEQ ID NO 3
<211> LENGTH: 42
<212> TYPE: DNA
<213> ORGANISM: Artificial Sequence
<220> FEATURE:
<223> OTHER INFORMATION: primer

<400> SEQUENCE: 3
acttcatagg aggcagatca aatgtcagag ttgagagcct tc                          42

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
gagtattacc tcctatttat caagataagt ttc                                    33

<210> SEQ ID NO 5
<211> LENGTH: 42
<212> TYPE: DNA
<213> ORGANISM: Artificial Sequence
<220> FEATURE:
<223> OTHER INFORMATION: primer

<400> SEQUENCE: 5
gataaatagg aggtaatact catgaccgtt tacacagcat cc                          42

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tacctgcagt tattcctttg gtagaccagt                                        30

<210> SEQ ID NO 7
<211> LENGTH: 45
<212> TYPE: DNA
<213> ORGANISM: Artificial Sequence
<220> FEATURE:
<223> OTHER INFORMATION: primer

<400> SEQUENCE: 7
gatgtcgact aggaggaata taaaatgaaa aattgtgtca tcgtc                       45

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
ttagctgtcc tccttaattc aaccgttcaa tcac                                   34

<210> SEQ ID NO 9
<211> LENGTH: 46
<212> TYPE: DNA
<213> ORGANISM: Artificial Sequence
<220> FEATURE:
<223> OTHER INFORMATION: primer

<400> SEQUENCE: 9
gatgtcgaca ggaggacagc taaatgaaac tctcaactaa actttg    46

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
agtgtaatcc tccttatttt ttaacatcgt aag    33

<210> SEQ ID NO 11
<211> LENGTH: 46
<212> TYPE: DNA
<213> ORGANISM: Artificial Sequence
<220> FEATURE:
<223> OTHER INFORMATION: primer

<400> SEQUENCE: 11
ttaaaaaata aggaggatta cactatggtt ttaaccaata aaacag    46

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
atcgtcgact taggatttaa tgcaggtgac ggacc    35

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
atcccgggag gaggattact atatgcaaac ggaacacgtc    40

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
atcccgggtt atttaagctg ggtaaatg    28

<210> SEQ ID NO 15
<211> LENGTH: 43
<212> TYPE: DNA
<213> ORGANISM: Artificial Sequence
<220> FEATURE:
<223> OTHER INFORMATION: primer -continued

```
<400> SEQUENCE: 15
agatccgcgg aggaggaatg agtaatggac tttccgcagc aac                    43

<210> SEQ ID NO 16
<211> LENGTH: 81
<212> TYPE: DNA
<213> ORGANISM: Artificial Sequence
<220> FEATURE:
<223> OTHER INFORMATION: primer

<400> SEQUENCE: 16
agtgagagct cttatttatt acgctggatg atgttgggct agcaggagga attcaccatg    60
agttttgata ttgccaaata c                                            81

<210> SEQ ID NO 17
<211> LENGTH: 50
<212> TYPE: DNA
<213> ORGANISM: Artificial Sequence
<220> FEATURE:
<223> OTHER INFORMATION: primer

<400> SEQUENCE: 17
tctgagcaac gaacgaagca tatatttatg tcctccaggc cttgattttg              50

<210> SEQ ID NO 18
<211> LENGTH: 50
<212> TYPE: DNA
<213> ORGANISM: Artificial Sequence
<220> FEATURE:
<223> OTHER INFORMATION: primer

<400> SEQUENCE: 18
caaaatcaag gcctggagga cataaatata tgcttcgttc gttgctcaga              50

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
gcatccatgg tatcatcctc cgttgatgtg atg                               33

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
tgataccatg gactttccgc agcaactcg                                    29

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
gtacatgcat ttatttatta cgctggatga tg                                32

<210> SEQ ID NO 22
```

<211> LENGTH: 59
<212> TYPE: DNA
<213> ORGANISM: Artificial Sequence
<220> FEATURE:
<223> OTHER INFORMATION: primer

<400> SEQUENCE: 22

```
gggtaccggg ccccccctcg cctctagagt cgactaggag gaattcacca tgagttttg         59
```

<210> SEQ ID NO 23
<211> LENGTH: 1671
<212> TYPE: DNA
<213> ORGANISM: Artificial Sequence
<220> FEATURE:
<223> OTHER INFORMATION: synthetic amorphadiene synthase gene

<400> SEQUENCE: 23

```
gattaaggca tgcaccatgg ccctgaccga agagaaaccg atccgcccga tcgctaactt         60
cccgccgtct atctggggtg accagttcct gatctacgaa aagcaggttg agcagggtgt        120
tgaacagatc gtaaacgacc tgaagaaaga agttcgtcag ctgctgaaag aagctctgga        180
catcccgatg aaacacgcta acctgctgaa actgatcgac gagatccagc gtctgggtat        240
cccgtaccac ttcgaacgcg aaatcgacca cgcactgcag tgcatctacg aaacctacgg        300
cgacaactgg aacggcgacc gttcttctct gtggtttcgt ctgatgcgta acagggcta         360
ctacgttacc tgtgacgttt taacaacta caaggacaag aacggtgctt tcaaacagtc        420
tctggctaac gacgttgaag gcctgctgga actgtacgaa gcgacctcca tgcgtgtacc        480
gggtgaaatc atcctggagg acgcgctggg tttcacccgt tctcgtctgt ccattatgac        540
taaagacgct ttctctacta acccggctct gttcaccgaa atccagcgtg ctctgaaaca        600
gccgctgtgg aaacgtctgc cgcgtatcga agcagcacag tacattccgt tttaccagca        660
gcaggactct cacaacaaga ccctgctgaa actggctaag ctggaattca acctgctgca        720
gtctctgcac aaagaagaac tgtctcacgt ttgtaagtgg tggaaggcat ttgacatcaa        780
gaaaaacgcg ccgtgcctgc gtgaccgtat cgttgaatgt tacttctggg gtctgggttc        840
tggttatgaa ccacagtact cccgtgcacg tgtgttcttc actaaagctg tagctgttat        900
caccctgatc gatgacactt acgatgctta cggcacctac gaagaactga agatctttac        960
tgaagctgta gaacgctggt ctatcacttg cctggacact ctgccggagt acatgaaacc       1020
gatctacaaa ctgttcatgg atacctacac cgaaatggag gaattcctgg caaaagaagg       1080
ccgtaccgac ctgttcaact gcggtaaaga gtttgttaaa gaattcgtac gtaacctgat       1140
ggttgaagct aaatgggcta acgaaggcca tatcccgact accgaagaac atgacccggt       1200
tgttatcatc accggcggtg caaacctgct gaccaccact tgctatctgg gtatgtccga       1260
catctttacc aaggaatctg ttgaatgggc tgtttctgca ccgccgctgt tccgttactc       1320
cggtattctg ggtcgtcgtc tgaacgacct gatgacccac aaagcagagc aggaacgtaa       1380
acactcttcc tcctctctgg aatcctacat gaaggaatat aacgttaacg aggagtacgc       1440
acagactctg atctataaag aagttgaaga cgtatggaaa gacatcaacc gtgaatacct       1500
gactactaaa aacatcccgc gcccgctgct gatggcagta atctacctgt gccagttcct       1560
ggaagtacag tacgctggta agataacctt cactcgcatg ggcgacgaat acaaacacct       1620
gatcaaatcc ctgctggttt acccgatgtc catctgatcc cgggattaga t                1671
```

<210> SEQ ID NO 24
<211> LENGTH: 1671
<212> TYPE: DNA

-continued

<213> ORGANISM: Artificial Sequence
<220> FEATURE:
<223> OTHER INFORMATION: synthetic amorphadiene synthase gene

<400> SEQUENCE: 24

| | | | | | |
|---|---|---|---|---|---|
| ctaattccgt | acgtggtacc | gggactggct | tctctttggc | taggcgggct | agcgattgaa | 60 |
| gggcggcaga | tagaccccac | tggtcaagga | ctagatgctt | ttcgtccaac | tcgtcccaca | 120 |
| acttgtctag | catttgctgg | acttcttttct | tcaagcagtc | gacgactttc | ttcgagacct | 180 |
| gtagggctac | tttgtgcgat | tggacgactt | tgactagctg | ctctaggtcg | cagacccata | 240 |
| gggcatggtg | aagcttgcgc | tttagctggt | gcgtgacgtc | acgtagatgc | tttggatgcc | 300 |
| gctgttgacc | ttgccgctgg | caagaagaga | caccaaagca | gactacgcat | ttgtcccgat | 360 |
| gatgcaatgg | acactgcaaa | aattgttgat | gttcctgttc | ttgccacgaa | agtttgtcag | 420 |
| agaccgattg | ctgcaacttc | cggacgacct | tgacatgctt | cgctggaggt | acgcacatgg | 480 |
| cccactttag | taggacctcc | tgcgcgaccc | aaagtgggca | agagcagaca | ggtaatactg | 540 |
| atttctgcga | aagagatgat | tgggccgaga | caagtggctt | taggtcgcac | gagactttgt | 600 |
| cggcgacacc | tttgcagacg | gcgcatagct | tcgtcgtgtc | atgtaaggca | aaatggtcgt | 660 |
| cgtcctgaga | gtgttgttct | gggacgactt | tgaccgattc | gaccttaagt | tggacgacgt | 720 |
| cagagacgtg | tttcttcttg | acagagtgca | aacattcacc | accttccgta | aactgtagtt | 780 |
| cttttttgcgc | ggcacggacg | cactggcata | gcaacttaca | atgaagaccc | cagacccaag | 840 |
| accaatactt | ggtgtcatga | gggcacgtgc | acacaagaag | tgatttcgac | atcgacaata | 900 |
| gtgggactag | ctactgtgaa | tgctacgaat | gccgtggatg | cttcttgact | tctagaaatg | 960 |
| acttcgacat | cttgcgacca | gatagtgaac | ggacctgtga | gacggcctca | tgtactttgg | 1020 |
| ctagatgttt | gacaagtacc | tatggatgtg | gctttacctc | cttaaggacc | gttttcttcc | 1080 |
| ggcatggctg | gacaagttga | cgccatttct | caaacaattt | cttaagcatg | cattggacta | 1140 |
| ccaacttcga | tttacccgat | tgcttccggt | ataggctga | tggcttcttg | tactgggcca | 1200 |
| acaatagtag | tggccgccac | gtttggacga | ctggtggtga | acgatagacc | catacaggct | 1260 |
| gtagaaatgg | ttccttagac | aacttacccg | acaaagacgt | ggcggcgaca | aggcaatgag | 1320 |
| gccataagac | ccagcagcag | acttgctgga | ctactgggtg | tttcgtctcg | tccttgcatt | 1380 |
| tgtgagaagg | aggagagacc | ttaggatgta | cttcctttata | ttgcaattgc | tcctcatgcg | 1440 |
| tgtctgagac | tagatatttc | ttcaacttct | gcatacctttt | ctgtagttgg | cacttatgga | 1500 |
| ctgatgattt | ttgtagggcg | cgggcgacga | ctaccgtcat | tagatggaca | cggtcaagga | 1560 |
| ccttcatgtc | atgcgaccat | ttctattgaa | gtgagcgtac | ccgctgctta | tgtttgtgga | 1620 |
| ctagtttagg | gacgaccaaa | tgggctacag | gtagactagg | gccctaatct | a | 1671 |

<210> SEQ ID NO 25
<211> LENGTH: 1185
<212> TYPE: DNA
<213> ORGANISM: Escherichia coli

<400> SEQUENCE: 25

| | | | | | |
|---|---|---|---|---|---|
| atgaaaaatt | gtgtcatcgt | cagtgcggta | cgtactgcta | tcggtagttt | taacggttca | 60 |
| ctcgcttcca | ccagcgccat | cgacctgggg | gcgacagtaa | ttaaagccgc | cattgaacgt | 120 |
| gcaaaaatcg | attcacaaca | cgttgatgaa | gtgattatgg | gtaacgtgtt | acaagccggg | 180 |
| ctggggcaaa | atccggcgcg | tcaggcactg | ttaaaaagcg | ggctggcaga | aacggtgtgc | 240 |
| ggattcacgg | tcaataaagt | atgtggttcg | ggtcttaaaa | gtgtggcgct | tgccgcccag | 300 |

```
gccattcagg caggtcaggc gcagagcatt gtggcggggg gtatggaaaa tatgagttta    360
gccccctact tactcgatgc aaaagcacgc tctggttatc gtcttggaga cggacaggtt    420
tatgacgtaa tcctgcgcga tggcctgatg tgcgccaccc atggttatca tatggggatt    480
accgccgaaa acgtggctaa agagtacgga attacccgtg aaatgcagga tgaactggcg    540
ctacattcac agcgtaaagc ggcagccgca attgagtccg gtgcttttac agccgaaatc    600
gtcccggtaa atgttgtcac tcgaaagaaa accttcgtct tcagtcaaga cgaattcccg    660
aaagcgaatt caacggctga agcgttaggt gcattgcgcc cggccttcga taaagcagga    720
acagtcaccg ctgggaacgc gtctggtatt aacgacggtg ctgccgctct ggtgattatg    780
gaagaatctg cggcgctggc agcaggcctt accccctgg ctcgcattaa aagttatgcc     840
agcggtggcg tgcccccgc attgatggg atggggccag tacctgccac gcaaaaagcg      900
ttacaactgg cggggctgca actggcggat attgatctca ttgaggctaa tgaagcattt    960
gctgcacagt tccttgccgt tgggaaaaac ctgggctttg attctgagaa agtgaatgtc   1020
aacggcgggg ccatcgcgct cgggcatcct atcggtgcca gtggtgctcg tattctggtc   1080
acactattac atgccatgca ggcacgcgat aaaacgctgg ggctggcaac actgtgcatt   1140
ggcggcggtc agggaattgc gatggtgatt gaacggttga attaa                   1185

<210> SEQ ID NO 26
<211> LENGTH: 1476
<212> TYPE: DNA
<213> ORGANISM: Escherichia coli

<400> SEQUENCE: 26
atgaaactct caactaaact ttgttggtgt ggtattaaag gaagacttag gccgcaaaag     60
caacaacaat tacacaatac aaacttgcaa atgactgaac taaaaaaaca aaagaccgct    120
gaacaaaaaa ccagacctca aaatgtcggt attaaaggta ccaaattta catcccaact    180
caatgtgtca accaatctga gctagagaaa tttgatggcg tttctcaagg taaatacaca    240
attggtctgg gccaaaccaa catgtctttt gtcaatgaca gagaagatat ctactcgatg    300
tccctaactg ttttgtctaa gttgatcaag agttacaaca tcgacaccaa caaaattggt    360
agattagaag tcggtactga aactctgatt gacaagtcca gtctgtcaa gtctgtcttg     420
atgcaattgt ttggtgaaaa cactgacgtc gaaggtattg acacgcttaa tgcctgttac    480
ggtggtacca acgcgttgtt caactctttg aactggattg aatctaacgc atgggatggt    540
agagacgcca ttgtagtttg cggtgatatt gccatctacg ataagggtgc cgcaagacca    600
accggtggtg ccggtactgt tgctatgtgg atcggtcctg atgctccaat tgtatttgac    660
tctgtaagag cttcttacat ggaacacgcc tacgattttt acaagccaga tttcaccagc    720
gaatatcctt acgtcgatgg tcatttttca ttaacttgtt acgtcaaggc tcttgatcaa    780
gtttacaaga gttattccaa gaaggctatt tctaaagggt tggttagcga tcccgctggt    840
tcggatgctt tgaacgtttt gaaatatttc gactacaacg ttttccatgt tccaacctgt    900
aaattggtca caaaatcata cggtagatta ctatataacg atttcagagc caatcctcaa    960
ttgttcccag aagttgacgc cgaattagct actcgcgatt atgacgaatc tttaaccgat   1020
aagaacattg aaaaaacttt tgttaatgtt gctaagccat ccacaaaaga gagagttgcc   1080
caatctttga ttgttccaac aaacacaggt aacatgtaca ccgcatctgt ttatgccgcc   1140
tttgcatctc tattaactat tgttggatct gacgacttac aaggcaagcg tgttggttta   1200
ttttcttacg gttccggttt agctgcatct ctatattctt gcaaaattgt tggtgacgtc   1260
```

```
caacatatta tcaaggaatt agatattact aacaaattag ccaagagaat caccgaaact    1320
ccaaaggatt acgaagctgc catcgaattg agagaaaatg cccatttgaa gaagaacttc    1380
aaacctcaag gttccattga gcatttgcaa agtggtgttt actacttgac caacatcgat    1440
gacaaattta gaagatctta cgatgttaaa aaataa                              1476

<210> SEQ ID NO 27
<211> LENGTH: 1509
<212> TYPE: DNA
<213> ORGANISM: Artificial Sequence
<220> FEATURE:
<223> OTHER INFORMATION: Truncated HMG-CoA reductase nucleotide
      sequence

<400> SEQUENCE: 27
atggttttaa ccaataaaac agtcatttct ggatcgaaag tcaaaagttt atcatctgcg     60
caatcgagct catcaggacc ttcatcatct agtgaggaag atgattcccg cgatattgaa    120
agcttggata agaaaatacg tccttttagaa gaattagaag cattattaag tagtggaaat    180
acaaaacaat gaagaacaa agaggtcgct gccttggtta ttcacggtaa gttacctttg    240
tacgctttgg agaaaaaatt aggtgatact acgagagcgg ttgcggtacg taggaaggct    300 cttttcaattt tggcagaagc tcctgtatta gcatctgatc gtttaccata taaaaattat    360
gactacgacc gcgtatttgg cgcttgttgt gaaaatgtta taggttacat gcctttgccc    420
gttggtgtta taggccccctt ggttatcgat ggtacatctt atcatatacc aatggcaact    480
acagagggtt gtttggtagc ttctgccatg cgtggctgta aggcaatcaa tgctggcggt    540
ggtgcaacaa ctgttttaac taaggatggt atgacaagag gcccagtagt ccgtttccca    600
actttgaaaa gatctggtgc ctgtaagata tggttagact cagaagaggg acaaaacgca    660
attaaaaaag cttttaactc tacatcaaga tttgcacgtc tgcaacatat tcaaacttgt    720
ctagcaggag atttactctt catgagattt agaacaacta ctggtgacgc aatgggtatg    780
aatatgattt ctaaaggtgt cgaatactca ttaaagcaaa tggtagaaga gtatggctgg    840
gaagatatgg aggttgtctc cgtttctggt aactactgta ccgacaaaaa accagctgcc    900
atcaactgga tcgaaggtcg tggtaagagt gtcgtcgcag aagctactat tcctggtgat    960
gttgtcagaa aagtgttaaa aagtgatgtt tccgcattgg ttgagttgaa cattgctaag    1020
aatttggttg atctgcaat ggctgggtct gttggtggat ttaacgcaca tgcagctaat    1080
ttagtgacag ctgttttctt ggcattagga caagatcctg cacaaaatgt tgaaagttcc    1140
aactgtataa cattgatgaa agaagtggac ggtgatttga gaatttccgt atccatgcca    1200
tccatcgaag taggtaccat cggtggtggt actgttctag aaccacaagg tgccatgttg    1260
gacttattag gtgtaagagg cccgcatgct accgctcctg gtaccaacgc acgtcaatta    1320
gcaagaatag ttgcctgtgc cgtcttggca ggtgaattat ccttatgtgc tgccctagca    1380
gccggccatt tggttcaaag tcatatgacc cacaacagga aacctgctga accaacaaaa    1440
cctaacaatt tggacgccac tgatataaat cgtttgaaag atgggtccgt cacctgcatt    1500
aaatcctaa                                                            1509

<210> SEQ ID NO 28
<211> LENGTH: 1332
<212> TYPE: DNA
<213> ORGANISM: Saccharomyces cerevisiae

<400> SEQUENCE: 28
atgtcattac cgttcttaac ttctgcaccg ggaaaggtta ttattttttgg tgaacactct     60
```

```
gctgtgtaca acaagcctgc cgtcgctgct agtgtgtctg cgttgagaac ctacctgcta      120
ataagcgagt catctgcacc agatactatt gaattggact tcccggacat tagctttaat      180
cataagtggt ccatcaatga tttcaatgcc atcaccgagg atcaagtaaa ctcccaaaaa      240
ttggccaagg ctcaacaagc caccgatggc ttgtctcagg aactcgttag tcttttggat      300
ccgttgttag ctcaactatc cgaatccttc cactaccatg cagcgttttg tttcctgtat      360
atgtttgttt gcctatgccc ccatgccaag aatattaagt tttctttaaa gtctacttta      420
cccatcggtg ctgggttggg ctcaagcgcc tctatttctg tatcactggc cttagctatg      480
gcctacttgg ggggttaat aggatctaat gacttggaaa agctgtcaga aaacgataag      540
catatagtga atcaatgggc cttcataggt gaaaagtgta ttcacggtac cccttcagga      600
atagataacg ctgtggccac ttatggtaat gccctgctat ttgaaaaaga ctcacataat      660
ggaacaataa acacaaacaa ttttaagttc ttagatgatt cccagccat tccaatgatc      720 ctaacctata ctagaattcc aaggtctaca aaagatcttg ttgctcgcgt tcgtgtgttg      780
gtcaccgaga aatttcctga agttatgaag ccaattctag atgccatggg tgaatgtgcc      840
ctacaaggct tagagatcat gactaagtta agtaaatgta aaggcaccga tgacgaggct      900
gtagaaacta ataatgaact gtatgaacaa ctattggaat tgataagaat aaatcatgga      960
ctgcttgtct caatcggtgt ttctcatcct ggattagaac ttattaaaaa tctgagcgat     1020
gatttgagaa ttggctccac aaaacttacc ggtgctggtg gcggcggttg ctctttgact     1080
ttgttacgaa gagacattac tcaagagcaa attgacagct tcaaaaagaa attgcaagat     1140
gattttagtt acgagacatt tgaaacagac ttgggtggga ctggctgctg tttgttaagc     1200
gcaaaaaatt tgaataaaga tcttaaaatc aaatccctag tattccaatt atttgaaaat     1260
aaaactacca caaagcaaca aattgacgat ctattattgc caggaaacac gaatttacca     1320
tggacttcat ag                                                         1332

<210> SEQ ID NO 29
<211> LENGTH: 1356
<212> TYPE: DNA
<213> ORGANISM: Saccharomyces cerevisiae

<400> SEQUENCE: 29
atgtcagagt tgagagcctt cagtgcccca gggaaagcgt tactagctgg tggatattta       60
gttttagata caaatatga agcatttgta gtcggattat cggcaagaat gcatgctgta      120
gcccatcctt acggttcatt gcaagggtct gataagtttg aagtgcgtgt gaaaagtaaa      180
caatttaaag atgggagtg gctgtaccat ataagtccta aaagtggctt cattcctgtt      240
tcgataggcg gatctaagaa ccctttcatt gaaaaagtta tcgctaacgt atttagctac      300
tttaaaccta acatgacga ctactgcaat agaaacttgt tcgttattga tattttctct      360
gatgatgcct accattctca ggaggatagc gttaccgaac atcgtggcaa cagaagattg      420
agttttcatt cgcacagaat tgaagaagtt cccaaaacag ggctgggctc ctcggcaggt      480
ttagtcacag ttttaactac agctttggcc tcctttttg tatcggacct ggaaaataat      540
gtagacaaat atagaagt tattcataat ttagcacaag ttgctcattg tcaagctcag      600
ggtaaaattg gaagcgggtt tgatgtagcg gcggcagcat atggatctat cagatataga      660
agattcccac ccgcattaat ctctaatttg ccagatattg gaagtgctac ttacggcagt      720 aaactgcgc atttggttga tgaagaagac tggaatatta cgattaaaag taaccattta      780
ccttcgggat taactttatg gatgggcgat attaagaatg gttcagaaac agtaaaactg      840
```

| | |
|---|---|
| gtccagaagg taaaaaattg gtatgattcg catatgccag aaagcttgaa aatatataca | 900 |
| gaactcgatc atgcaaattc tagatttatg gatggactat ctaaactaga tcgcttacac | 960 |
| gagactcatg acgattacag cgatcagata tttgagtctc ttgagaggaa tgactgtacc | 1020 |
| tgtcaaaagt atcctgaaat cacagaagtt agagatgcag ttgccacaat tagacgttcc | 1080 |
| tttagaaaaa taactaaaga atctggtgcc gatatcgaac ctcccgtaca aactagctta | 1140 |
| ttggatgatt gccagacctt aaaaggagtt cttacttgct taatacctgg tgctggtggt | 1200 |
| tatgacgcca ttgcagtgat tactaagcaa gatgttgatc ttagggctca aaccgctaat | 1260 |
| gacaaaagat tttctaaggt tcaatggctg gatgtaactc aggctgactg gggtgttagg | 1320 |
| aaagaaaaag atccggaaac ttatcttgat aaatag | 1356 |

<210> SEQ ID NO 30
<211> LENGTH: 1191
<212> TYPE: DNA
<213> ORGANISM: Saccharomyces cerevisiae

<400> SEQUENCE: 30

| | |
|---|---|
| atgaccgttt acacagcatc cgttaccgca cccgtcaaca tcgcaaccct taagtattgg | 60 |
| gggaaaaggg acacgaagtt gaatctgccc accaattcgt ccatatcagt gactttatcg | 120 |
| caagatgacc tcagaacgtt gacctctgcg gctactgcac ctgagtttga acgcgacact | 180 |
| ttgtggttaa atggagaacc acacagcatc gacaatgaaa gaactcaaaa ttgtctgcgc | 240 |
| gacctacgcc aattaagaaa ggaaatggaa tcgaaggacg cctcattgcc acattatct | 300 |
| caatggaaac tccacattgt ctccgaaaat aactttccta cagcagctgg tttagcttcc | 360 |
| tccgctgctg gctttgctgc attggtctct gcaattgcta agttataccaa attaccacag | 420 |
| tcaacttcag aaatatctag aatagcaaga aaggggtctg gttcagcttg tagatcgttg | 480 |
| tttggcggat acgtggcctg ggaaatggga aaagctgaag atggtcatga ttccatggca | 540 |
| gtacaaatcg cagacagctc tgactggcct cagatgaaag cttgtgtcct agttgtcagc | 600 |
| gatattaaaa aggatgtgag ttccactcag ggtatgcaat tgaccgtggc aacctccgaa | 660 |
| ctatttaaag aaagaattga acatgtcgta ccaaagagat ttgaagtcat gcgtaaagcc | 720 |
| attgttgaaa aagatttcgc caccttttgca aaggaaacaa tgatggattc caactctttc | 780 |
| catgccacat gtttggactc tttccctcca atattctaca tgaatgacac ttccaagcgt | 840 |
| atcatcagtt ggtgccacac cattaatcag ttttacggag aaacaatcgt tgcatacacg | 900 |
| tttgatgcag gtccaaatgc tgtgttgtac tacttagctg aaaatgagtc gaaactcttt | 960 |
| gcatttatct ataaattgtt tggctctgtt cctggatggg acaagaaatt tactactgag | 1020 |
| cagcttgagg ctttcaacca tcaatttgaa tcatctaact ttactgcacg tgaattggat | 1080 |
| cttgagttgc aaaaggatgt tgccagagtg attttaactc aagtcggttc aggcccacaa | 1140 |
| gaaacaaacg aatctttgat tgacgcaaag actggtctac caaaggaata a | 1191 |

<210> SEQ ID NO 31
<211> LENGTH: 9253
<212> TYPE: DNA
<213> ORGANISM: Artificial Sequence
<220> FEATURE:
<223> OTHER INFORMATION: "single operon" nucleotide sequence

<400> SEQUENCE: 31

| | |
|---|---|
| gacgcttttt atcgcaactc tctactgttt ctccataccc gttttttttgg gctagcagga | 60 |
| ggaattcacc atggtacccg ggaggaggat tactatatgc aaacggaaca cgtcatttta | 120 |

```
ttgaatgcac agggagttcc cacgggtacg ctggaaaagt atgccgcaca cacggcagac    180
acccgcttac atctcgcgtt ctccagttgg ctgtttaatg ccaaaggaca attattagtt    240
acccgccgcg cactgagcaa aaaagcatgg cctggcgtgt ggactaactc ggtttgtggg    300
cacccacaac tgggagaaag caacgaagac gcagtgatcc gccgttgccg ttatgagctt    360
ggcgtggaaa ttacgcctcc tgaatctatc tatcctgact ttcgctaccg cgccaccgat    420
ccgagtggca ttgtggaaaa tgaagtgtgt ccggtatttg ccgcacgcac cactagtgcg    480
ttacagatca atgatgatga agtgatggat tatcaatggt gtgatttagc agatgtatta    540
cacggtattg atgccacgcc gtgggcgttc agtccgtgga tggtgatgca ggcgacaaat    600
cgcgaagcca gaaaacgatt atctgcattt acccagctta ataacccgg  ggatcctcta    660
gagtcgacta ggaggaatat aaaatgaaaa attgtgtcat cgtcagtgcg gtacgtactg    720
ctatcggtag ttttaacggt tcactcgctt ccaccagcgc catcgacctg ggggcgacag    780
taattaaagc cgccattgaa cgtgcaaaaa tcgattcaca acacgttgat gaagtgatta    840
tgggtaacgt gttacaagcc gggctggggc aaaatccggc gcgtcaggca ctgttaaaaa    900
gcgggctggc agaaacggtg tgcggattca cggtcaataa agtatgtggt tcgggtctta    960
aaagtgtggc gcttgccgcc caggccattc aggcaggtca ggcgcagagc attgtggcgg   1020
ggggtatgga aaatatgagt ttagcccccct acttactcga tgcaaaagca cgctctggtt   1080
atcgtcttgg agacggacag gtttatgacg taatcctgcg cgatggcctg atgtgcgcca   1140
cccatggtta tcatatgggg attaccgccg aaaacgtggc taaagagtac ggaattaccc   1200
gtgaaatgca ggatgaactg gcgctacatt cacagcgtaa agcggcagcc gcaattgagt   1260
ccggtgcttt tacagccgaa atcgtcccgg taaatgttgt cactcgaaag aaaaccttcg   1320
tcttcagtca agacgaattc ccgaaagcga attcaacggc tgaagcgtta ggtgcattgc   1380
gcccggcctt cgataaagca ggaacagtca ccgctgggaa cgcgtctggt attaacgacg   1440
gtgctgccgc tctggtgatt atggaagaat ctgcggcgct ggcagcaggc cttaccccc    1500
tggctcgcat taaaagttat gccagcggtg gcgtgccccc cgcattgatg ggtatggggc   1560
cagtacctgc cacgcaaaaa gcgttacaac tggcggggct gcaactggcg gatattgatc   1620
tcattgaggc taatgaagca tttgctgcac agttccttgc cgttgggaaa acctgggct    1680
ttgattctga gaaagtgaat gtcaacggcg gggccatcgc gctcgggcat cctatcggtg   1740
ccagtggtgc tcgtattctg gtcacactat tacatgccat gcaggcacgc gataaaacgc   1800
tggggctggc aacactgtgc attggcggcg gtcagggaat tgcgatggtg attgaacggt   1860
tgaattaagg aggacagcta aatgaaactc tcaactaaac tttgttggtg tggtattaaa   1920
ggaagactta ggccgcaaaa gcaacaacaa ttacacaata caaacttgca aatgactgaa   1980
ctaaaaaaac aaaagaccgc tgaacaaaaa accagacctc aaaatgtcgg tattaaaggt   2040
atccaaattt acatcccaac tcaatgtgtc aaccaatctg agctagagaa atttgatggc   2100
gtttctcaag gtaaatacac aattggtctg ggccaaacca acatgtcttt tgtcaatgac   2160
agagaagata tctactcgat gtccctaact gttttgtcta agttgatcaa gagttacaac   2220
atcgacacca acaaaattgg tagattagaa gtcggtactg aaactctgat tgacaagtcc   2280
aagtctgtca gtctgtcttt gatgcaattg tttggtgaaa acactgacgt cgaaggtatt   2340
gacacgctta atgcctgtta cggtggtacc aacgcgttgt tcaactcttt gaactggatt   2400
gaatctaacg catgggatgg tagagacgcc attgtagttt gcggtgatat tgccatctac   2460
gataagggtg ccgcaagacc aaccggtggt gccggtactg ttgctatgtg gatcggtcct   2520
```

```
gatgctccaa ttgtatttga ctctgtaaga gcttcttaca tggaacacgc ctacgatttt    2580
tacaagccag atttcaccag cgaatatcct tacgtcgatg gtcattttc attaacttgt     2640 tacgtcaagg ctcttgatca agtttacaag agttattcca agaaggctat ttctaaaggg    2700
ttggttagcg atcccgctgg ttcggatgct ttgaacgttt tgaaatattt cgactacaac    2760
gttttccatg ttccaacctg taaattggtc acaaaatcat acggtagatt actatataac    2820
gatttcagag ccaatcctca attgttccca gaagttgacg ccgaattagc tactcgcgat    2880
tatgacgaat cttaaccga taagaacatt gaaaaaactt ttgttaatgt tgctaagcca     2940
ttccacaaag agagagttgc ccaatctttg attgttccaa caaacacagg taacatgtac    3000
accgcatctg tttatgccgc ctttgcatct ctattaaact atgttggatc tgacgactta    3060
caaggcaagc gtgttggttt attttcttac ggttccggtt tagctgcatc tctatattct    3120
tgcaaaattg ttggtgacgt ccaacatatt atcaaggaat tagatattac taacaaatta    3180
gccaagagaa tcaccgaaac tccaaaggat tacgaagctg ccatcgaatt gagagaaaat    3240
gcccatttga agaagaactt caaacctcaa ggttccattg agcatttgca aagtggtgtt    3300
tactacttga ccaacatcga tgacaaattt agaagatctt acgatgttaa aaaataagga    3360
ggattacact atggttttaa ccaataaaac agtcatttct ggatcgaaag tcaaaagttt    3420
atcatctgcg caatcgagct catcaggacc ttcatcatct agtgaggaag atgattcccg    3480
cgatattgaa agcttggata agaaaatacg tcctttagaa gaattagaag cattattaag    3540
tagtggaaat acaaaacaat tgaagaacaa agaggtcgct gccttggtta ttcacggtaa    3600
gttacctttg tacgctttgg agaaaaaatt aggtgatact acgagagcgg ttgcggtacg    3660
taggaaggct ctttcaattt tggcagaagc tcctgtatta gcatctgatc gtttaccata    3720
taaaaattat gactacgacc gcgtatttgg cgcttgttgt gaaaatgtta taggttacat    3780
gcctttgccc gttggtgtta taggcccctt ggttatcgat ggtacatctt atcatatacc    3840
aatggcaact acagagggtt gtttggtagc ttctgccatg cgtggctgta aggcaatcaa    3900
tgctggcggt ggtgcaacaa ctgttttaac taaggatggt atgacaagag gcccagtagt    3960
ccgtttccca actttgaaaa gatctggtgc ctgtaagata tggttagact cagaagaggg    4020
acaaaacgca attaaaaaag cttttaactc tacatcaaga tttgcacgtc tgcaacatat    4080
tcaaacttgt ctagcaggag atttactctt catgagattt agaacaacta ctggtgacgc    4140
aatgggtatg aatatgattt ctaaaggtgt cgaatactca ttaaagcaaa tggtagaaga    4200
gtatggctgg gaagatatgg aggttgtctc cgtttctggt aactactgta ccgacaaaaa    4260
accagctgcc atcaactgga tcgaaggtcg tggtaagagt gtcgtcgcag aagctactat    4320
tcctggtgat gttgtcagaa aagtgttaaa aagtgatgtt tccgcattgg ttgagttgaa    4380
cattgctaag aatttggttg atctgcaat ggctgggtct gttggtggat ttaacgcaca      4440
tgcagctaat ttagtgacag ctgttttctt ggcattagga caagatcctg cacaaaatgt    4500
tgaaagttcc aactgtataa cattgatgaa agaagtggac ggtgatttga gaatttccgt    4560
atccatgcca tccatcgaag taggtaccat cggtggtggt actgttctag aaccacaagg    4620
tgccatgttg gacttattag gtgtaagagg cccgcatgct accgctcctg gtaccaacgc    4680
acgtcaatta gcaagaatag ttgcctgtgc cgtcttggca ggtgaattat ccttatgtgc    4740
tgccctagca gccggccatt tggttcaaag tcatatgacc cacaacagga aacctgctga    4800
accaacaaaa cctaacaatt tggacgccac tgatataaat cgtttgaaag atgggtccgt    4860
cacctgcatt aaatcctaag tcgacctgca gtaggaggaa ttaaccatgt cattaccgtt    4920
```

```
cttaacttct gcaccgggaa aggttattat ttttggtgaa cactctgctg tgtacaacaa    4980
gcctgccgtc gctgctagtg tgtctgcgtt gagaacctac ctgctaataa gcgagtcatc    5040
tgcaccagat actattgaat tggacttccc ggacattagc tttaatcata agtggtccat    5100
caatgatttc aatgccatca ccgaggatca agtaaactcc caaaaattgg ccaaggctca    5160
acaagccacc gatggcttgt ctcaggaact cgttagtctt ttggatccgt tgttagctca    5220
actatccgaa tccttccact accatgcagc gttttgtttc ctgtatatgt ttgtttgcct    5280
atgcccccat gccaagaata ttaagttttc tttaaagtct actttaccca tcggtgctgg    5340
gttgggctca agcgcctcta tttctgtatc actggcctta gctatggcct acttgggggg    5400
gttaatagga tctaatgact tggaaaagct gtcagaaaac gataagcata tagtgaatca    5460
atgggccttc ataggtgaaa agtgtattca cggtacccct tcaggaatag ataacgctgt    5520
ggccacttat ggtaatgccc tgctatttga aaaagactca cataatggaa caataaacac    5580
aaacaatttt aagttcttag atgatttccc agccattcca atgatcctaa cctatactag    5640
aattccaagg tctacaaaag atcttgttgc tcgcgttcgt gtgttggtca ccgagaaatt    5700
tcctgaagtt atgaagccaa ttctagatgc catgggtgaa tgtgccctac aaggcttaga    5760
gatcatgact aagttaagta aatgtaaagg caccgatgac gaggctgtag aaactaataa    5820
tgaactgtat gaacaactat tggaattgat aagaataaat catggactgc ttgtctcaat    5880
cggtgtttct catcctggat tagaacttat taaaaatctg agcgatgatt tgagaattgg    5940
ctccacaaaa cttaccggtg ctggtggcgg cggttgctct ttgactttgt tacgaagaga    6000
cattactcaa gagcaaattg acagcttcaa aaagaaattg caagatgatt ttagttacga    6060
gacatttgaa acagacttgg gtgggactgg ctgctgtttg ttaagcgcaa aaaatttgaa    6120
taaagatctt aaaatcaaat ccctagtatt ccaattattt gaaaataaaa ctaccacaaa    6180
gcaacaaatt gacgatctat tattgccagg aaacacgaat ttaccatgga cttcatagga    6240
ggcagatcaa atgtcagagt tgagagcctt cagtgcccca gggaaagcgt tactagctgg    6300
tggatattta gttttagata caaaatatga agcatttgta gtcggattat cggcaagaat    6360
gcatgctgta gcccatcctt acggttcatt gcaagggtct gataagtttg aagtgcgtgt    6420
gaaaagtaaa caatttaaag atggggagtg gctgtaccat ataagtccta aaagtggctt    6480
cattcctgtt tcgataggcg gatctaagaa ccctttcatt gaaaaagtta tcgctaacgt    6540
atttagctac tttaaaccta acatggacga ctactgcaat agaaacttgt tcgttattga    6600
tattttctct gatgatgcct accattctca ggaggatagc gttaccgaac atcgtggcaa    6660
cagaagattg agttttcatt cgcacagaat tgaagaagtt cccaaaacag ggctgggctc    6720
ctcggcaggt ttagtcacag ttttaactac agctttggcc tccttttttg tatcggacct    6780
ggaaaataat gtagacaaat atagagaagt tattcataat ttagcacaag ttgctcattg    6840
tcaagctcag ggtaaaattg gaagcgggtt tgatgtagcg gcggcagcat atggatctat    6900
cagatataga agattcccac ccgcattaat ctctaatttg ccagatattg aagtgctac    6960 ttacggcagt aaactggcgc atttggttga tgaagaagac tggaatatta cgattaaaag    7020
taaccattta ccttcgggat taactttatg gatgggcgat attaagaatg gttcagaaac    7080
agtaaaactg gtccagaagg taaaaaattg gtatgattcg catatgccag aaagcttgaa    7140
aatatataca gaactcgatc atgcaaattc tagatttatg gatggactat ctaaactaga    7200
tcgcttacac gagactcatg acgattacag cgatcagata tttgagtctc ttgagaggaa    7260
tgactgtacc tgtcaaaagt atcctgaaat cacagaagtt agagatgcag ttgccacaat    7320
```

```
tagacgttcc tttagaaaaa taactaaaga atctggtgcc gatatcgaac ctcccgtaca    7380
aactagctta ttggatgatt gccagacctt aaaaggagtt cttacttgct taatacctgg    7440
tgctggtggt tatgacgcca ttgcagtgat tactaagcaa gatgttgatc ttagggctca    7500
aaccgctaat gacaaaagat tttctaaggt tcaatggctg gatgtaactc aggctgactg    7560
gggtgttagg aaagaaaaag atccggaaac ttatcttgat aaataggagg taatactcat    7620
gaccgtttac acagcatccg ttaccgcacc cgtcaacatc gcaacccttg agtattgggg    7680
gaaaagggac acgaagttga atctgcccac caattcgtcc atatcagtga ctttatcgca    7740
agatgacctc agaacgttga cctctgcggc tactgcacct gagtttgaac gcgacacttt    7800
gtggttaaat ggagaaccac acagcatcga caatgaaaga actcaaaatt gtctgcgcga    7860
cctacgccaa ttaagaaagg aaatggaatc gaaggacgcc tcattgccca cattatctca    7920
atggaaactc acattgtct  ccgaaaataa cttttcctaca gcagctggtt agcttcctc     7980 cgctgctggc tttgctgcat tggtctctgc aattgctaag ttataccaat taccacagtc    8040
aacttcagaa atatctagaa tagcaagaaa ggggtctggt tcagcttgta gatcgttgtt    8100
tggcggatac gtggcctggg aaatgggaaa agctgaagat ggtcatgatt ccatggcagt    8160
acaaatcgca gacagctctg actggcctca gatgaaagct tgtgtcctag ttgtcagcga    8220
tattaaaaag gatgtgagtt ccactcaggg tatgcaattg accgtggcaa cctccgaact    8280
atttaaagaa agaattgaac atgtcgtacc aaagagattt gaagtcatgc gtaaagccat    8340
tgttgaaaaa gatttcgcca cctttgcaaa ggaaacaatg atggattcca actctttcca    8400
tgccacatgt ttggactctt tccctccaat attctacatg aatgacactt ccaagcgtat    8460
catcagttgg tgccacacca ttaatcagtt ttacggagaa acaatcgttg catacacgtt    8520
tgatgcaggt ccaaatgctg tgttgtacta cttagctgaa aatgagtcga actctttgc     8580 atttatctat aaattgtttg gctctgttcc tggatgggac aagaaattta ctactgagca    8640
gcttgaggct ttcaaccatc aatttgaatc atctaacttt actgcacgtg aattggatct    8700
tgagttgcaa aaggatgttg ccagagtgat tttaactcaa gtcggttcag gcccacaaga    8760
aacaaacgaa tctttgattg acgcaaagac tggtctacca aaggaataac tgcaggcatg    8820
caagcttggc tgttttggcg gatgagagaa gattttcagc ctgatacaga ttaaatcaga    8880
acgcagaagc ggtctgataa aacagaattt gcctggcggc agtagcgcgg tggtcccacc    8940
tgaccccatg ccgaactcag aagtgaaacg ccgtagcgcc gatggtagtg tggggtctcc    9000
ccatgcgaga gtagggaact gccaggcatc aaataaaacg aaaggctcag tcgaaagact    9060
gggcctttcg ttttatctgt tgtttgtcgg tgaacgctct cctgagtagg acaaatccgc    9120
cgggagcgga tttgaacgtt gcgaagcaac ggcccggagg gtggcgggca ggacgcccgc    9180
cataaactgc caggcatcaa attaagcaga aggccatcct gacggatggc ctttttgcgt    9240
ttctacaaac tct                                                       9253

<210> SEQ ID NO 32
<211> LENGTH: 4760
<212> TYPE: DNA
<213> ORGANISM: Artificial Sequence
<220> FEATURE:
<223> OTHER INFORMATION: "MEVT" operon nucleotide sequence

<400> SEQUENCE: 32 gacgctttt atcgcaactc tctactgttt ctccatacc gttttttgg gctagcagga       60 ggaattcacc atggtacccg ggatcctct agagtcgact aggaggaata taaaatgaaa    120
```

```
aattgtgtca tcgtcagtgc ggtacgtact gctatcggta gttttaacgg ttcactcgct    180
tccaccagcg ccatcgacct gggggcgaca gtaattaaag ccgccattga acgtgcaaaa    240
atcgattcac aacacgttga tgaagtgatt atgggtaacg tgttacaagc cgggctgggg    300
caaaatccgg cgcgtcaggc actgttaaaa agcgggctgg cagaaacggt gtgcggattc    360
acggtcaata agtatgtgg ttcgggtctt aaaagtgtgg cgcttgccgc ccaggccatt    420
caggcaggtc aggcgcagag cattgtggcg gggggtatgg aaaatatgag tttagccccc    480
tacttactcg atgcaaaagc acgctctggt tatcgtcttg gagacggaca ggtttatgac    540
gtaatcctgc gcgatggcct gatgtgcgcc acccatggtt atcatatggg gattaccgcc    600
gaaaacgtgg ctaaagagta cggaattacc cgtgaaatgc aggatgaact ggcgctacat    660
tcacagcgta aagcggcagc cgcaattgag tccggtgctt ttacagccga aatcgtcccg    720
gtaaatgttg tcactcgaaa gaaaaccttc gtcttcagtc aagacgaatt cccgaaagcg    780
aattcaacgg ctgaagcgtt aggtgcattg cgcccggcct tcgataaagc aggaacagtc    840
accgctggga acgcgtctgg tattaacgac ggtgctgccg ctctggtgat tatggaagaa    900
tctgcggcgc tggcagcagg ccttacccccc ctggctcgca ttaaaagtta tgccagcggt    960
ggcgtgcccc ccgcattgat gggtatgggg ccagtacctg ccacgcaaaa agcgttacaa   1020
ctggcggggc tgcaactggc ggatattgat ctcattgagg ctaatgaagc atttgctgca   1080
cagttccttg ccgttgggaa aaacctgggc tttgattctg agaaagtgaa tgtcaacggc   1140
ggggccatcg cgctcgggca tcctatcggt gccagtggtg ctcgtattct ggtcacacta   1200
ttacatgcca tgcaggcacg cgataaaacg ctggggctgg caacactgtg cattggcggc   1260
ggtcagggaa ttgcgatggt gattgaacgg ttgaattaag gaggacagct aaatgaaact   1320
ctcaactaaa cttgttggt gtggtattaa aggaagactt aggccgcaaa agcaacaaca   1380
attacacaat acaaacttgc aaatgactga actaaaaaaa caaagaccg ctgaacaaaa   1440 aaccagacct caaaatgtcg gtattaaagg tatccaaatt tacatcccaa ctcaatgtgt   1500
caaccaatct gagctagaga aatttgatgg cgtttctcaa ggtaaataca caattggtct   1560
gggccaaacc aacatgtctt ttgtcaatga cagagaagat atctactcga tgtccctaac   1620
tgttttgtct aagttgatca agagttacaa catcgacacc aacaaaattg gtagattaga   1680
agtcggtact gaaactctga ttgacaagtc caagtctgtc aagtctgtct tgatgcaatt   1740
gtttggtgaa aacactgacg tcgaaggtat tgacacgctt aatgcctgtt acggtggtac   1800
caacgcgttg ttcaactctt tgaactggat tgaatctaac gcatgggatg gtagagacgc   1860
cattgtagtt tgcggtgata ttgccatcta cgataagggt gccgcaagac caaccgtgg   1920 tgccggtact gttgctatgt ggatcggtcc tgatgctcca attgtatttg actctgtaag   1980
agcttcttac atggaacacg cctacgattt ttacaagcca gatttcacca gcgaatatcc   2040
ttacgtcgat ggtcattttt cattaacttg ttacgtcaag gctcttgatc aagtttacaa   2100
gagttattcc aagaaggcta tttctaaagg gttggttagc gatcccgctg gttcggatgc   2160
tttgaacgtt ttgaaatatt tcgactacaa cgttttccat gttccaacct gtaaattggt   2220
cacaaaatca tacggtagat tactatataa cgatttcaga gccaatcctc aattgttccc   2280
agaagttgac gccgaattag ctactcgcga ttatgacgaa tctttaaccg ataagaacat   2340
tgaaaaaact tttgttaatg ttgctaagcc attccacaaa gagagagttg cccaatcttt   2400
gattgttcca acaaacacag gtaacatgta caccgcatct gtttatgccg cctttgcatc   2460
tctattaaac tatgttggat ctgacgactt acaaggcaag cgtgttggtt tatttttctta   2520
```

```
cggttccggt ttagctgcat ctctatattc ttgcaaaatt gttggtgacg tccaacatat    2580
tatcaaggaa ttagatatta ctaacaaatt agccaagaga atcaccgaaa ctccaaagga    2640
ttacgaagct gccatcgaat tgagagaaaa tgcccatttg aagaagaact tcaaacctca    2700
aggttccatt gagcatttgc aaagtggtgt ttactacttg accaacatcg atgacaaatt    2760
tagaagatct tacgatgtta aaaaataagg aggattacac tatggtttta accaataaaa    2820
cagtcatttc tggatcgaaa gtcaaaagtt tatcatctgc gcaatcgagc tcatcaggac    2880
cttcatcatc tagtgaggaa gatgattccc gcgatattga agcttggat aagaaaatac     2940 gtcctttaga agaattagaa gcattattaa gtagtggaaa tacaaaacaa ttgaagaaca    3000
aagaggtcgc tgccttggtt attcacggta agttacctt gtacgctttg gagaaaaaat     3060
taggtgatac tacgagagcg gttgcggtac gtaggaaggc tctttcaatt ttggcagaag    3120
ctcctgtatt agcatctgat cgtttaccat ataaaaatta tgactacgac cgcgtatttg    3180
gcgcttgttg tgaaaatgtt ataggttaca tgcctttgcc cgttggtgtt ataggcccct    3240
tggttatcga tggtacatct tatcatatac caatggcaac tacagagggt tgtttggtag    3300
cttctgccat gcgtggctgt aaggcaatca atgctggcgg tggtgcaaca actgttttaa    3360
ctaaggatgg tatgacaaga ggcccagtag tccgtttccc aactttgaaa agatctggtg    3420
cctgtaagat atggttagac tcagaagagg gacaaaacgc aattaaaaaa gcttttaact    3480
ctacatcaag atttgcacgt ctgcaacata ttcaaacttg tctagcagga gatttactct    3540
tcatgagatt tagaacaact actggtgacg caatgggtat gaatatgatt tctaaaggtg    3600
tcgaatactc attaaagcaa atggtagaag agtatggctg ggaagatatg gaggttgtct    3660
ccgtttctgg taactactgt accgacaaaa aaccagctgc catcaactgg atcgaaggtc    3720
gtggtaagag tgtcgtcgca gaagctacta ttcctggtga tgttgtcaga aaagtgttaa    3780
aaagtgatgt ttccgcattg gttgagttga acattgctaa gaatttggtt ggatctgcaa    3840
tggctgggtc tgttggtgga tttaacgcac atgcagctaa tttagtgaca gctgttttct    3900
tggcattagg acaagatcct gcacaaaatg ttgaaagttc caactgtata acattgatga    3960
aagaagtgga cggtgatttg agaatttccg tatccatgcc atccatcgaa gtaggtacca    4020
tcggtggtgg tactgttcta gaaccacaag gtgccatgtt ggacttatta ggtgtaagag    4080
gcccgcatgc taccgctcct ggtaccaacg cacgtcaatt agcaagaata gttgcctgtg    4140
ccgtcttggc aggtgaatta tccttatgtg ctgccctagc agccggccat ttggttcaaa    4200
gtcatatgac ccacaacagg aaacctgctg aaccaacaaa acctaacaat ttggacgcca    4260
ctgatataaa tcgtttgaaa gatgggtccg tcacctgcat taaatcctaa gtcgacctgc    4320
aggcatgcaa gcttggctgt tttggcggat gagagaagat tttcagcctg atacagatta    4380
aatcagaacg cagaagcggt ctgataaaac agaatttgcc tggcggcagt agcgcggtgg    4440
tcccacctga ccccatgccg aactcagaag tgaaacgccg tagcgccgat ggtagtgtgg    4500
ggtctcccca tgcgagagta gggaactgcc aggcatcaaa taaaacgaaa ggctcagtcg    4560
aaagactggg cctttcgttt tatctgttgt ttgtcggtga acgctctcct gagtaggaca    4620
aatccgccgg gagcggattt gaacgttgcg aagcaacggc ccggagggtg cgggcagga    4680 cgcccgccat aaactgccag gcatcaaatt aagcagaagg ccatcctgac ggatggcctt    4740
tttgcgtttc tacaaactct                                                 4760
```

<210> SEQ ID NO 33
<211> LENGTH: 4482

<212> TYPE: DNA
<213> ORGANISM: Artificial Sequence
<220> FEATURE:
<223> OTHER INFORMATION: "MEVB" operon nucleotide sequence

<400> SEQUENCE: 33

```
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctggg     180
taccgggccc cccctcgagg tcgacggtat cgataagctt gatatcgaat tcctgcagta     240
ggaggaatta accatgtcat taccgttctt aacttctgca ccgggaaagg ttattatttt     300
tggtgaacac tctgctgtgt acaacaagcc tgccgtcgct gctagtgtgt ctgcgttgag     360
aacctacctg ctaataagcg agtcatctgc accagatact attgaattgg acttcccgga     420
cattagcttt aatcataagt ggtccatcaa tgatttcaat gccatcaccg aggatcaagt     480
aaactcccaa aaattggcca aggctcaaca agccaccgat ggcttgtctc aggaactcgt     540
tagtcttttg gatccgttgt tagctcaact atccgaatcc ttccactacc atgcagcgtt     600
ttgtttcctg tatatgtttg tttgcctatg ccccatgcc aagaatatta gttttctttt     660
aaagtctact ttacccatcg gtgctgggtt gggctcaagc gcctctattt ctgtatcact     720
ggccttagct atggcctact tggggggggtt aataggatct aatgacttgg aaaagctgtc     780
agaaaacgat aagcatatag tgaatcaatg ggccttcata ggtgaaaagt gtattcacgg     840
tacccccttca ggaatagata cgctgtggc cacttatggt aatgccctgc tatttgaaaa     900
agactcacat aatggaacaa taaacacaaa caattttaag ttcttagatg atttcccagc     960
cattccaatg atcctaacct atactagaat tccaaggtct acaaaagatc ttgttgctcg    1020
cgttcgtgtg ttggtcaccg agaaatttcc tgaagttatg aagccaattc tagatgccat    1080
gggtgaatgt gccctacaag gcttagagat catgactaag ttaagtaaat gtaaaggcac    1140
cgatgacgag gctgtagaaa ctaataatga actgtatgaa caactattgg aattgataag    1200
aataaatcat ggactgcttg tctcaatcgg tgtttctcat cctggattag aacttattaa    1260
aaatctgagc gatgatttga gaattggctc cacaaaactt accggtgctg gtggcggcgg    1320
ttgctctttg actttgttac gaagagacat tactcaagag caaattgaca gcttcaaaaa    1380
gaaattgcaa gatgatttta gttacgagac atttgaaaca gacttgggtg ggactggctg    1440
ctgtttgtta agcgcaaaaa atttgaataa agatcttaaa atcaaatccc tagtattcca    1500
attatttgaa aataaaacta ccacaaagca acaaattgac gatctattat tgccaggaaa    1560
cacgaattta ccatggactt cataggaggc agatcaaatg tcagagttga gagccttcag    1620
tgccccaggg aaagcgttac tagctggtgg atatttagtt ttagatacaa aatatgaagc    1680
atttgtagtc ggattatcgg caagaatgca tgctgtagcc catccttacg gttcattgca    1740
agggtctgat aagtttgaag tgcgtgtgaa aagtaaacaa tttaaagatg gggagtggct    1800
gtaccatata agtcctaaaa gtggcttcat tcctgtttcg ataggcggat ctaagaaccc    1860
tttcattgaa aaagttatcg ctaacgtatt tagctacttt aaacctaaca tggacgacta    1920
ctgcaataga aacttgttcg ttattgatat tttctctgat gatgcctacc attctcagga    1980
ggatagcgtt accgaacatc gtggcaacag aagattgagt tttcattcgc acagaattga    2040
agaagttccc aaaacagggc tgggctcctc ggcaggttta gtcacagttt taactacagc    2100
tttggcctcc tttttgtat cggacctgga aaataatgta gacaaatata gagaagttat    2160
tcataattta gcacaagttg ctcattgtca agctcagggt aaaattggaa gcgggtttga    2220
```

```
tgtagcggcg gcagcatatg gatctatcag atatagaaga ttcccacccg cattaatctc    2280
taatttgcca gatattggaa gtgctactta cggcagtaaa ctggcgcatt tggttgatga    2340
agaagactgg aatattacga ttaaaagtaa ccatttacct tcgggattaa ctttatggat    2400
gggcgatatt aagaatggtt cagaaacagt aaaactggtc cagaaggtaa aaaattggta    2460
tgattcgcat atgccagaaa gcttgaaaat atatacagaa ctcgatcatg caaattctag    2520
atttatggat ggactatcta aactagatcg cttacacgag actcatgacg attacagcga    2580
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaaagga    3720
aacaatgatg gattccaact cttttccatg ccacatgtttg gactctttcc ctccaatatt    3780
ctacatgaat gacacttcca gcgtatcat cagttggtgc cacaccatta atcagtttta    3840
cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat tgaatcatc     4020 taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccggggg atccactagt tctagagcgg ccgccaccgc    4200
ggtggagctc caattcgccc tatagtgagt cgtattacgc gcgctcactg gccgtcgttt    4260
tacaacgtcg tgactgggaa aaccctggcg ttacccaact taatcgcctt gcagcacatc    4320
cccctttcgc cagctggcgt aatagcgaag aggcccgcac cgatcgccct tcccaacagt    4380
tgcgcagcct gaatggcgaa tggaaattgt aagcgttaat attttgttaa aattcgcgtt    4440
aaatttttgt taaatcagct cattttttaa ccaataggcc ga                       4482
```

<210> SEQ ID NO 34
<211> LENGTH: 549

```
<212> TYPE: DNA
<213> ORGANISM: Escherichia coli

<400> SEQUENCE: 34
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttaccgc cgcgcactga gcaaaaaagc atggcctggc      180
gtgtggacta actcggtttg tgggcaccca caactgggag aaagcaacga agacgcagtg     240
atccgccgtt gccgttatga gcttggcgtg gaaattacgc ctcctgaatc tatctatcct     300
gactttcgct accgcgccac cgatccgagt ggcattgtgg aaaatgaagt gtgtccggta     360
tttgccgcac gcaccactag tgcgttacag atcaatgatg atgaagtgat ggattatcaa     420
tggtgtgatt tagcagatgt attacacggt attgatgcca cgccgtgggc gttcagtccg     480
tggatggtga tgcaggcgac aaatcgcgaa gccagaaaac gattatctgc atttacccag     540
cttaaataa                                                              549

<210> SEQ ID NO 35
<211> LENGTH: 900
<212> TYPE: DNA
<213> ORGANISM: Escherichia coli

<400> SEQUENCE: 35
atggactttc cgcagcaact cgaagcctgc gttaagcagg ccaaccaggc gctgagccgt      60
tttatcgccc cactgcccct tcagaacact cccgtggtcg aaaccatgca gtatggcgca     120
ttattaggtg gtaagcgcct gcgaccttc ctggtttatg ccaccggtca tatgttcggc      180
gttagcacaa acacgctgga cgcacccgct gccgccgttg agtgtatcca cgcttactca     240
ttaattcatg atgatttacc ggcaatggat gatgacgatc tgcgtcgcgg tttgccaacc     300
tgccatgtga gtttggcga agcaaacgcg attctcgctg cgacgctttt acaaacgctg     360
gcgttctcga tttttaagcga tgccgatatg ccggaagtgt cggaccgcga cagaatttcg     420
atgatttctg aactggcgag cgccagtggt attgccggaa tgtgcggtgg tcaggcatta     480
gatttagacg cggaaggcaa acacgtacct ctggacgcgc ttgagcgtat tcatcgtcat     540
aaaaccggcg cattgattcg cgccgccgtt cgccttggtg cattaagcgc cggagataaa     600
ggacgtcgtg ctctgccggt actcgacaag tatgcagaga gcatcggcct tgccttccag     660
gttcaggatg acatcctgga tgtggtggga gatactgcaa cgttgggaaa acgccagggt     720
gccgaccagc aacttggtaa aagtacctac cctgcacttc tgggtcttga gcaagcccgg     780
aagaaagccc gggatctgat cgacgatgcc cgtcagtcgc tgaaacaact ggctgaacag     840
tcactcgata cctcggcact ggaagcgcta gcggactaca tcatccagcg taataaataa     900

<210> SEQ ID NO 36
<211> LENGTH: 5051
<212> TYPE: DNA
<213> ORGANISM: Artificial Sequence
<220> FEATURE:
<223> OTHER INFORMATION: MBI operon

<400> SEQUENCE: 36
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctggg     180
taccgggccc cccctcgagg tcgacggtat cgataagctt gatatcgaat tcctgcagta     240
```

```
ggaggaatta accatgtcat taccgttctt aacttctgca ccgggaaagg ttattatttt    300
tggtgaacac tctgctgtgt acaacaagcc tgccgtcgct gctagtgtgt ctgcgttgag    360
aacctacctg ctaataagcg agtcatctgc accagatact attgaattgg acttcccgga    420
cattagcttt aatcataagt ggtccatcaa tgatttcaat gccatcaccg aggatcaagt    480
aaactcccaa aaattggcca aggctcaaca agccaccgat ggcttgtctc aggaactcgt    540
tagtcttttg gatccgttgt tagctcaact atccgaatcc ttccactacc atgcagcgtt    600
ttgtttcctg tatatgtttg tttgcctatg cccccatgcc aagaatatta agttttcttt    660
aaagtctact ttacccatcg gtgctgggtt gggctcaagc gcctctattt ctgtatcact    720
ggccttagct atggcctact tgggggggtt aataggatct aatgacttgg aaaagctgtc    780
agaaaacgat aagcatatag tgaatcaatg ggccttcata ggtgaaaagt gtattcacgg    840
taccccttca ggaatagata acgctgtggc cacttatggt aatgccctgc tatttgaaaa    900
agactcacat aatggaacaa taaacacaaa caattttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgatttta gttacgagac atttgaaaca gacttgggtg ggactggctg   1440
ctgtttgtta agcgcaaaaa atttgaataa agatcttaaa atcaaatccc tagtattcca   1500
attatttgaa aataaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa aatatgaagc   1680
atttgtagtc ggattatcgg caagaatgca tgctgtagcc catccttacg gttcattgca   1740
agggtctgat aagtttgaag tgcgtgtgaa aagtaaacaa tttaaagatg gggagtggct   1800
gtaccatata agtcctaaaa gtggcttcat tcctgtttcg ataggcggat ctaagaaccc   1860
tttcattgaa aaagttatcg ctaacgtatt tagctacttt aaacctaaca tggacgacta   1920
ctgcaataga aacttgttcg ttattgatat tttctctgat gatgcctacc attctcagga   1980
ggatagcgtt accgaacatc gtggcaacag aagattgagt tttcattcgc acagaattga   2040
agaagttccc aaaacagggc tgggctcctc ggcaggttta gtcacagttt taactacagc   2100
tttggcctcc ttttttgtat cggacctgga aaataatgta gacaaatata gagaagttat   2160
tcataattta gcacaagttg ctcattgtca agctcagggt aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt tggttgatga   2340
agaagactgg aatattacga ttaaaagtaa ccatttacct tcgggattaa ctttatggat   2400
gggcgatatt aagaatggtt cagaaacagt aaaactggtc cagaaggtaa aaaattggta   2460
tgattcgcat atgccagaaa gcttgaaaat atatacagaa ctcgatcatg caaattctag   2520
atttatggat ggactatcta aactagatcg cttacacgag actcatgacg attacagcga   2580
tcagatattt gagtctcttg agaggaatga ctgtacctgt caaaagtatc ctgaaatcac   2640
```

```
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attgggggaa aagggacacg aagttgaatc tgccccaccaa   3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taagaaaga attgaacatg tcgtaccaaa    3660
gagatttgaa gtcatgcgta aagccattgt tgaaaaagat ttcgccacct ttgcaaagga    3720
aacaatgatg gattccaact cttttccatgc cacatgtttg gactcttttcc ctccaatatt    3780
ctacatgaat gacacttcca agcgtatcat cagttggtgc cacaccatta atcagtttta    3840
cggagaaaca atcgttgcat acacgtttga tgcaggtcca aatgctgtgt tgtactactt    3900
agctgaaaat gagtcgaaac tctttgcatt tatctataaa ttgttttgct ctgttcctgg    3960
atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200
attttattga atgcacaggg agttcccacg ggtacgctgg aaaagtatgc cgcacacacg    4260
gcagacaccc gcttacatct cgcgttctcc agttggctgt ttaatgccaa aggacaatta    4320
ttagttaccc gccgcgcact gagcaaaaaa gcatggcctg gcgtgtggac taactcggtt    4380
tgtgggcacc cacaactggg agaaagcaac gaagacgcag tgatccgccg ttgccgttat    4440
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattcacg gtattgatgc cacgccgtgg gcgttcagtc cgtggatggt gatgcaggcg    4680
acaaatcgcg aagccagaaa acgattatct gcatttaccc agcttaaata acccggggga    4740
tccactagtt ctagagcggc cgccaccgcg gtggagctcc aattcgccct atagtgagtc    4800
gtattacgcg cgctcactgg ccgtcgtttt acaacgtcgt gactgggaaa accctggcgt    4860
tacccaactt aatcgccttg cagcacatcc ccctttcgcc agctggcgta atagcgaaga    4920
ggcccgcacc gatcgccctt cccaacagtt gcgcagcctg aatggcgaat ggaaattgta    4980
agcgttaata ttttgttaaa attcgcgtta aattttgtt aaatcagctc attttttaac    5040
```

-continued caataggccg a                                                5051

<210> SEQ ID NO 37
<211> LENGTH: 5963
<212> TYPE: DNA
<213> ORGANISM: Artificial Sequence
<220> FEATURE:
<223> OTHER INFORMATION: MBIS operon

<400> SEQUENCE: 37

| | | | | | |
|---|---|---|---|---|---|
| gcgcaacgca | attaatgtga | gttagctcac | tcattaggca | ccccaggctt | tacactttat | 60 |
| gcttccggct | cgtatgttgt | gtggaattgt | gagcggataa | caatttcaca | caggaaacag | 120 |
| ctatgaccat | gattacgcca | agcgcgcaat | taaccctcac | taaagggaac | aaaagctggg | 180 |
| tacccggccc | cccctcgagg | tcgacggtat | cgataagctt | gatatcgaat | tcctgcagta | 240 |
| ggaggaatta | accatgtcat | taccgttctt | aacttctgca | ccgggaaagg | ttattatttt | 300 |
| tggtgaacac | tctgctgtgt | acaacaagcc | tgccgtcgct | gctagtgtgt | ctgcgttgag | 360 |
| aacctacctg | ctaataagcg | agtcatctgc | accagatact | attgaattgg | acttcccgga | 420 |
| cattagcttt | aatcataagt | ggtccatcaa | tgatttcaat | gccatcaccg | aggatcaagt | 480 |
| aaactcccaa | aaattggcca | aggctcaaca | agccaccgat | ggcttgtctc | aggaactcgt | 540 |
| tagtctttg | gatccgttgt | tagctcaact | atccgaatcc | ttccactacc | atgcagcgtt | 600 |
| ttgtttcctg | tatatgtttg | tttgcctatg | cccccatgcc | aagaatatta | agttttcttt | 660 |
| aaagtctact | ttacccatcg | gtgctgggtt | gggctcaagc | gcctctattt | ctgtatcact | 720 |
| ggccttagct | atggcctact | tgggggggtt | aataggatct | aatgacttgg | aaaagctgtc | 780 |
| agaaaacgat | aagcatatag | tgaatcaatg | gccttcata | ggtgaaaagt | gtattcacgg | 840 |
| taccccttca | ggaatagata | acgctgtggc | cacttatggt | aatgccctgc | tatttgaaaa | 900 |
| agactcacat | aatggaacaa | taaacacaaa | caattttaag | ttcttagatg | atttcccagc | 960 |
| cattccaatg | atcctaacct | atactagaat | tccaaggtct | acaaaagatc | ttgttgctcg | 1020 |
| cgttcgtgtg | ttggtcaccg | agaaatttcc | tgaagttatg | aagccaattc | tagatgccat | 1080 |
| gggtgaatgt | gccctacaag | gcttagagat | catgactaag | ttaagtaaat | gtaaaggcac | 1140 |
| cgatgacgag | gctgtagaaa | ctaataatga | actgtatgaa | caactattgg | aattgataag | 1200 |
| aataaatcat | ggactgcttg | tctcaatcgg | tgtttctcat | cctggattag | aacttattaa | 1260 |
| aaatctgagc | gatgatttga | gaattggctc | cacaaaactt | accggtgctg | gtggcggcgg | 1320 |
| ttgctctttg | actttgttac | gaagagacat | tactcaagag | caaattgaca | gcttcaaaaa | 1380 |
| gaaattgcaa | gatgattta | gttacgagac | atttgaaaca | gacttgggtg | ggactggctg | 1440 |
| ctgtttgtta | agcgcaaaaa | atttgaataa | agatcttaaa | atcaaatccc | tagtattcca | 1500 |
| attatttgaa | aataaaacta | ccacaaagca | acaaattgac | gatctattat | tgccaggaaa | 1560 |
| cacgaattta | ccatggactt | cataggaggc | agatcaaatg | tcagagttga | gagccttcag | 1620 |
| tgccccaggg | aaagcgttac | tagctggtgg | atatttagtt | ttagatacaa | aatatgaagc | 1680 |
| atttgtagtc | ggattatcgg | caagaatgca | tgctgtagcc | catccttacg | gttcattgca | 1740 |
| agggtctgat | aagtttgaag | tgcgtgtgaa | agtaaacaa | tttaaagatg | gggagtggct | 1800 |
| gtaccatata | agtcctaaaa | gtggcttcat | tcctgtttcg | ataggcggat | ctaagaaccc | 1860 |
| tttcattgaa | aaagttatcg | ctaacgtatt | tagctacttt | aaacctaaca | tggacgacta | 1920 |
| ctgcaataga | aacttgttcg | ttattgatat | tttctctgat | gatgcctacc | attctcagga | 1980 |
| ggatagcgtt | accgaacatc | gtggcaacag | aagattgagt | tttcattcgc | acagaattga | 2040 |

```
agaagttccc aaaacagggc tgggctcctc ggcaggttta gtcacagttt taactacagc   2100
tttggcctcc ttttttgtat cggacctgga aataatgta gacaaatata gagaagttat   2160
tcataattta gcacaagttg ctcattgtca agctcaggat aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt tggttgatga   2340
agaagactgg aatattacga ttaaaagtaa ccatttacct tcgggattaa ctttatggat   2400
gggcgatatt aagaatggtt cagaaacagt aaaactggtc cagaaggtaa aaaattggta   2460
tgattcgcat atgccagaaa gcttgaaaat atatacagaa ctcgatcatg caaattctag   2520
atttatggat ggactatcta aactagatcg cttacacgag actcatgacg attacagcga   2580
tcagatattt gagtctcttg agaggaatga ctgtacctgt caaaagtatc ctgaaatcac   2640
agaagttaga gatgcagttg ccacaattag acgttccttt agaaaaataa ctaaagaatc   2700
tggtgccgat atcgaacctc ccgtacaaac tagcttattg gatgattgcc agaccttaaa   2760
aggagttctt acttgcttaa tacctggtgc tggtggttat gacgccattg cagtgattac   2820
taagcaagat gttgatctta gggctcaaac cgctaatgac aaaagatttt ctaaggttca   2880
atggctggat gtaactcagg ctgactgggg tgttaggaaa gaaaagatc cggaaactta   2940 tcttgataaa taggaggtaa tactcatgac cgtttacaca gcatccgtta ccgcacccgt   3000
caacatcgca acccttaagt attggggaa aagggacacg aagttgaatc tgcccaccaa   3060
ttcgtccata tcagtgactt tatcgcaaga tgacctcaga acgttgacct ctgcggctac   3120
tgcacctgag tttgaacgcg acactttgtg gttaaatgga gaaccacaca gcatcgacaa   3180
tgaaagaact caaaattgtc tgcgcgacct acgccaatta agaaaggaaa tggaatcgaa   3240
ggacgcctca ttgcccacat tatctcaatg gaaactccac attgtctccg aaaataactt   3300
tcctacagca gctggtttag cttcctccgc tgctggcttt gctgcattgg tctctgcaat   3360
tgctaagtta taccaattac cacagtcaac ttcagaaata tctagaatag caagaaaggg   3420
gtctggttca gcttgtagat cgttgtttgg cggatacgtg gcctgggaaa tgggaaaagc   3480
tgaagatggt catgattcca tggcagtaca aatcgcagac agctctgact ggcctcagat   3540
gaaagcttgt gtcctagttg tcagcgatat taaaaaggat gtgagttcca ctcagggtat   3600
gcaattgacc gtggcaacct ccgaactatt taaagaaaga attgaacatg tcgtaccaaa   3660
gagatttgaa gtcatgcgta aagccattgt tgaaaaagat ttcgccacct ttgcaaagga   3720
aacaatgatg gattccaact cttttccatg cacatgtttg gactctttcc ctccaatatt   3780
ctacatgaat gacacttcca agcgtatcat cagttggtgc cacaccatta atcagtttta   3840
cggagaaaca atcgttgcat acacgtttga tgcaggtcca aatgctgtgt tgtactactt   3900
agctgaaaat gagtcgaaac tctttgcatt tatctataaa ttgtttggct ctgttcctgg   3960
atgggacaag aaatttacta ctgagcagct tgaggctttc aaccatcaat tgaatcatc   4020 taactttact gcacgtgaat tggatcttga gttgcaaaag gatgttgcca gagtgatttt   4080
aactcaagtc ggttcaggcc cacaagaaac aaacgaatct ttgattgacg caaagactgg   4140
tctaccaaag gaataactgc agcccgggag gaggattact atatgcaaac ggaacacgtc   4200
attttattga atgcacaggg agttcccacg ggtacgctgg aaaagtatgc cgcacacacg   4260
gcagacaccc gcttacatct cgcgttctcc agttggctgt ttaatgccaa aggacaatta   4320
ttagttaccc gccgcgcact gagcaaaaaa gcatggcctg gcgtgtggac taactcggtt   4380
tgtgggcacc cacaactggg agaaagcaac gaagacgcag tgatccgccg ttgccgttat   4440
```

-continued

```
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattacacg gtattgatgc cacgccgtgg gcgttcagtc cgtggatggt gatgcaggcg    4680
acaaatcgcg aagccagaaa acgattatct gcatttaccc agcttaaata acccggggga    4740
tccactagtt ctagagcggc cgccaccgcg gaggaggaat gagtaatgga ctttccgcag    4800
caactcgaag cctgcgttaa gcaggccaac caggcgctga gccgttttat cgccccactg    4860 cccttt caga cactcccgt ggtcgaaacc atgcagtatg gcgcattatt aggtggtaag    4920
cgcctgcgac ctttcctggt ttatgccacc ggtcatatgt tcggcgttag cacaaacacg    4980
ctggacgcac ccgctgccgc cgttgagtgt atccacgctt actcattaat tcatgatgat    5040
ttaccggcaa tggatgatga cgatctgcgt cgcggtttgc caacctgcca tgtgaagttt    5100
ggcgaagcaa acgcgattct cgctggcgac gctttacaaa cgctggcgtt ctcgatttta    5160
agcgatgccg atatgccgga agtgtcggac cgcgacagaa tttcgatgat ttctgaactg    5220
gcgagcgcca gtggtattgc cggaatgtgc ggtggtcagg cattagattt agacgcggaa    5280
ggcaaacacg tacctctgga cgcgcttgag cgtattcatc gtcataaaac cggcgcattg    5340
attcgcgccg ccgttcgcct tggtgcatta agcgccggag ataaaggacg tcgtgctctg    5400
ccggtactcg acaagtatgc agagagcatc ggccttgcct tccaggttca ggatgacatc    5460
ctggatgtgg tgggagatac tgcaacgttg ggaaaacgcc agggtgccga ccagcaactt    5520
ggtaaaagta cctaccctgc acttctgggt cttgagcaag cccggaagaa agcccgggat    5580
ctgatcgacg atgcccgtca gtcgctgaaa caactggctg aacagtcact cgatacctcg    5640
gcactggaag cgctagcgga ctacatcatc cagcgtaata aataagagct ccaattcgcc    5700
ctatagtgag tcgtattacg cgcgctcact ggccgtcgtt ttacaacgtc gtgactggga    5760
aaaccctggc gttacccaac ttaatcgcct tgcagcacat ccccctttcg ccagctggcg    5820
taatagcgaa gaggcccgca ccgatcgccc ttcccaacag ttgcgcagcc tgaatggcga    5880
atggaaattg taagcgttaa tattttgtta aaattcgcgt taaattttg ttaaatcagc    5940 tcattttta accaataggc cga                                             5963
```

METHODS FOR IDENTIFYING A BIOSYNTHETIC PATHWAY GENE PRODUCT

CROSS-REFERENCE

This application claims the benefit of U.S. Provisional Patent Application No. 60/507,220, filed Sep. 29, 2003, which application is incorporated herein by reference in its entirety.

STATEMENT REGARDING FEDERALLY SPONSORED RESEARCH

The U.S. government may have certain rights in this invention, pursuant to grant no. BES9911463 awarded by the National Science Foundation.

FIELD OF THE INVENTION

The present invention is in the field of identification and isolation of genes involved in biosynthetic pathways, and in particular to identification and isolation of genes involved in terpenoid biosynthesis.

BACKGROUND OF THE INVENTION

Isoprenoids constitute an extremely large and diverse group of natural products that have a common biosynthetic origin, i.e., a single metabolic precursor, isopentenyl diphosphate (IPP). At least 20,000 isoprenoids have been described. By definition, isoprenoids are made up of so-called isoprene (C5) units. The number of C-atoms present in the isoprenoids can be divided by five (C5, C10, C15, C20, C25, C30 and C40); although irregular isoprenoids and polyterpenes have been reported. Isoprenoid compounds are also referred to as "terpenes" or "terpenoids." Important members of the isoprenoids include the carotenoids, sesquiterpenoids, diterpenoids, and hemiterpenes. Carotenoids include, e.g., lycopene, β-carotene, and the like, many of which function as antioxidants. Sesquiterpenoids, include, e.g., artemisinin, a compound having anti-malarial activity. Diterpenoids, include, e.g., taxol, a cancer chemotherapeutic agent.

Identification and characterization of genes involved in biosynthetic pathways is of interest in basic and applied research. Identification of genes involved in biosynthetic pathways is typically carried out by identifying mutant genes that adversely affect the pathway, and isolating the mutant gene. Such processes are time-consuming and laborious, and in many cases identify genes not directly related to the biosynthetic pathway of interest. Other standard methods used to identify new biosynthetic pathway genes involve the identification of genes with nucleotide sequence similarity to previously discovered genes. However, these methods have limitations, as undiscovered biosynthetic pathway gene products may not bear sequence similarity to known biosynthetic pathway gene products. As such, there is a need in the art for methods of identifying genes involved in biosynthetic pathways. The present invention addresses this need.

LITERATURE

Martin et al. *Nature Biotechnology* 21(7):796-802 (2003); Wang and Ohnuma (2000) *Biochim. Biophys. Acta* 1529:33-48; Trapp and Croteau (2001) *Genetics* 158:811-832; Back and Chappell (1996) *Proc. Natl. Acad. Sci. USA* 93:6841-6845; U.S. Patent Publication No. 20030148479.

SUMMARY OF THE INVENTION

The present invention provides isolated, genetically modified host cells, where a host cell is genetically modified with a nucleic acid that includes a nucleotide sequence encoding a biosynthetic pathway enzyme. Synthesis of the enzyme in the host cell results in conversion of a substrate for the enzyme into a biosynthetic pathway intermediate, which intermediate is produced in an amount effective to inhibit growth of the genetically modified host cell. The present invention further provides compositions and kits comprising a subject genetically modified host cell. Subject host cells are useful for identifying a gene product having activity in a biosynthetic pathway. The present invention further provides methods of identifying a gene product having activity in a biosynthetic pathway.

BRIEF DESCRIPTION OF THE DRAWINGS

FIGS. 12A-C depict the nucleotide sequence of a synthetic nucleic acid that encodes amorphadiene synthase.

DEFINITIONS

Figure 1:
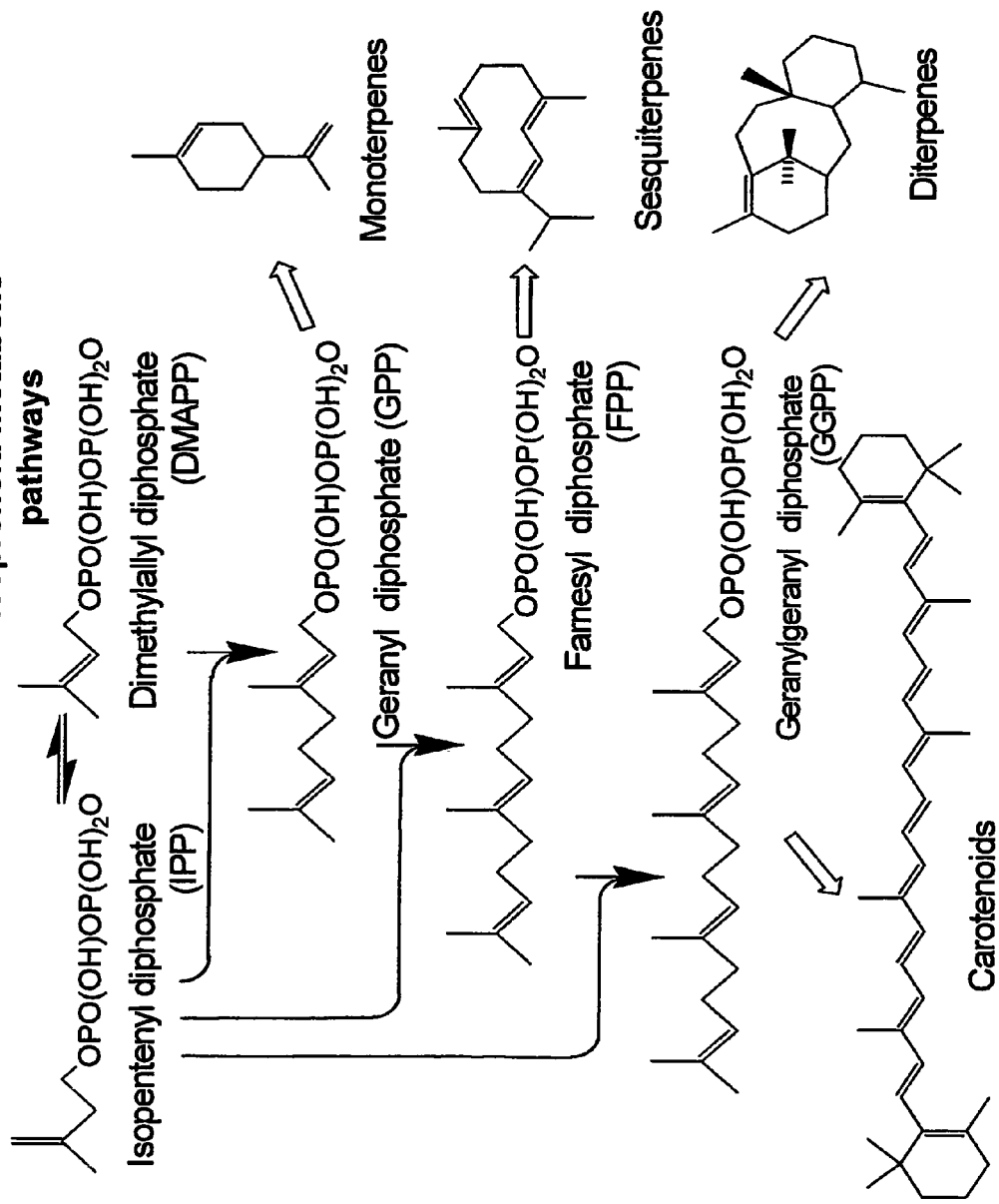
FIG. 1 is a schematic representation of isoprenoid metabolic pathways that result in the production of the terpene biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA or protein that is encoded by a DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring. Generally, the term naturally occurring refers to a nucleic acid, a cell, or an organism as present in a non-pathological (un-diseased) individual, such as would be typical for the species.

"Recombinant," as used herein, means that a particular DNA or RNA sequence is the product of various combinations of cloning, restriction, and/or ligation steps resulting in a construct having a structural coding or non-coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions.

Thus, e.g., the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. The term "recombinant" virus or viral RNA refers to one which is not naturally occurring, or is made by the artificial combination of two or more otherwise distinct viruses. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

Similarly, a "recombinant polypeptide" refers to a polypeptide or polyprotein which is not naturally occurring, or is made by the artificial combination of two otherwise separated segments of amino acid sequences. This artificial combination may be accomplished by standard techniques of recombinant DNA technology, such as described above, i.e., a recombinant polypeptide may be encoded by a recombinant polynucleotide. Thus, a recombinant polypeptide is an amino acid sequence encoded by all or a portion of a recombinant polynucleotide.

As used herein, the term "exogenous nucleic acid" refers to a nucleic acid that is not normally produced by a given bacterium, organism, or cell in nature.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a nucleic acid, e.g., an expression vector, that comprises a nucleotide sequence encoding one or more biosynthetic pathway gene products. Similarly, a subject prokaryotic host cell is a genetically modified prokaryotic host cell (e.g., a bacterium), by virtue of introduction into a suitable prokaryotic host cell an exogenous nucleic acid, e.g., a nucleic acid that is foreign to the prokaryotic host cell; and a subject eukaryotic host cell is a genetically modified eukaryotic host cell, by virtue of introduction into a suitable eukaryotic host cell an exogenous nucleic acid, e.g., a nucleic acid that is foreign to the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation region, the coding region for the protein of interest, and a transcriptional termination region. Transcriptional control regions include promoters that provide for overexpression of the protein of interest in the genetically modified host cell; control regions that provide for inducible expression, such that when an inducing agent is added to the culture medium, transcription of the coding region of the protein of interest is induced.

As used herein, the term "metabolic pathway" includes catabolic pathways and anabolic pathways. Anabolic pathways involve constructing a larger molecule from smaller molecules, a process requiring energy. Catabolic pathways involve breaking down of larger molecules, often releasing energy. An anabolic pathway is referred to herein as "a biosynthetic pathway."

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP through a MEV pathway intermediate.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of exemplary conditions uses a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions use higher temperatures in which the washes are identical to those above except for the temperature of the final two 30 minute washes in 0.2×SSC, 0.5% SDS was increased to 60° C. Another set of highly stringent conditions uses two final washes in 0.1×SSC, 0.1% SDS at 65° C. Another example of stringent hybridization conditions is hybridization at 50° C. or higher and 0.1× SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. An exemplary minimum length for a hybridizable nucleic acid is at least about 15 nucleotides; at least about 20 nucleotides; or at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a biosynthetic intermediate" includes a plurality of such intermediates, reference to "a nucleic acid" includes a plurality of such nucleic acids, and reference to "the genetically modified host cell" includes reference to one or more genetically modified host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides screening methods for identifying a gene product having activity in a biosynthetic pathway. The methods generally involve a) producing a test cell by introducing into a genetically modified host cell an exogenous nucleic acid comprising a nucleotide sequence encoding a candidate gene product, wherein the genetically modified host cell produces a biosynthetic pathway intermediate, which intermediate is produced in an amount effective to inhibit growth of the genetically modified host cell; and b) determining the effect, if any, of expression of the candidate gene product on the growth of the test cell. A reduction in growth inhibition of the test cell indicates that the exogenous nucleic acid encodes a gene product having activity in the biosynthetic pathway.

The present invention further provides isolated, genetically modified host cells; and libraries of genetically modified host cells. A subject genetically modified host cell is one that is genetically modified with one or more nucleic acids that include nucleotide sequences encoding one or more biosynthetic pathway enzymes, forming a genetically modified host cell. Synthesis of the biosynthetic pathway enzyme(s) in the host cell results in conversion of a substrate for the enzyme into a biosynthetic pathway intermediate, which intermediate is produced in an amount effective to inhibit growth of the genetically modified host cell. The present invention further provides compositions and kits comprising a subject genetically modified host cell; and compositions and kits comprising a subject genetically modified host cell library.

The present invention provides screening methods, for identifying a gene product having activity in a terpene biosynthetic pathway. The methods generally involve a) producing a test cell by introducing into a genetically modified host cell an exogenous nucleic acid comprising a nucleotide sequence encoding a candidate gene product, wherein the genetically modified host cell produces a terpene biosynthetic pathway intermediate, which intermediate is produced in an amount effective to inhibit growth of the genetically modified host cell; and b) determining the effect, if any, of expression of the candidate gene product on the growth of the test cell. A reduction in growth inhibition indicates that the exogenous nucleic acid encodes a gene product having activity in the terpene biosynthetic pathway.

Figure 2:
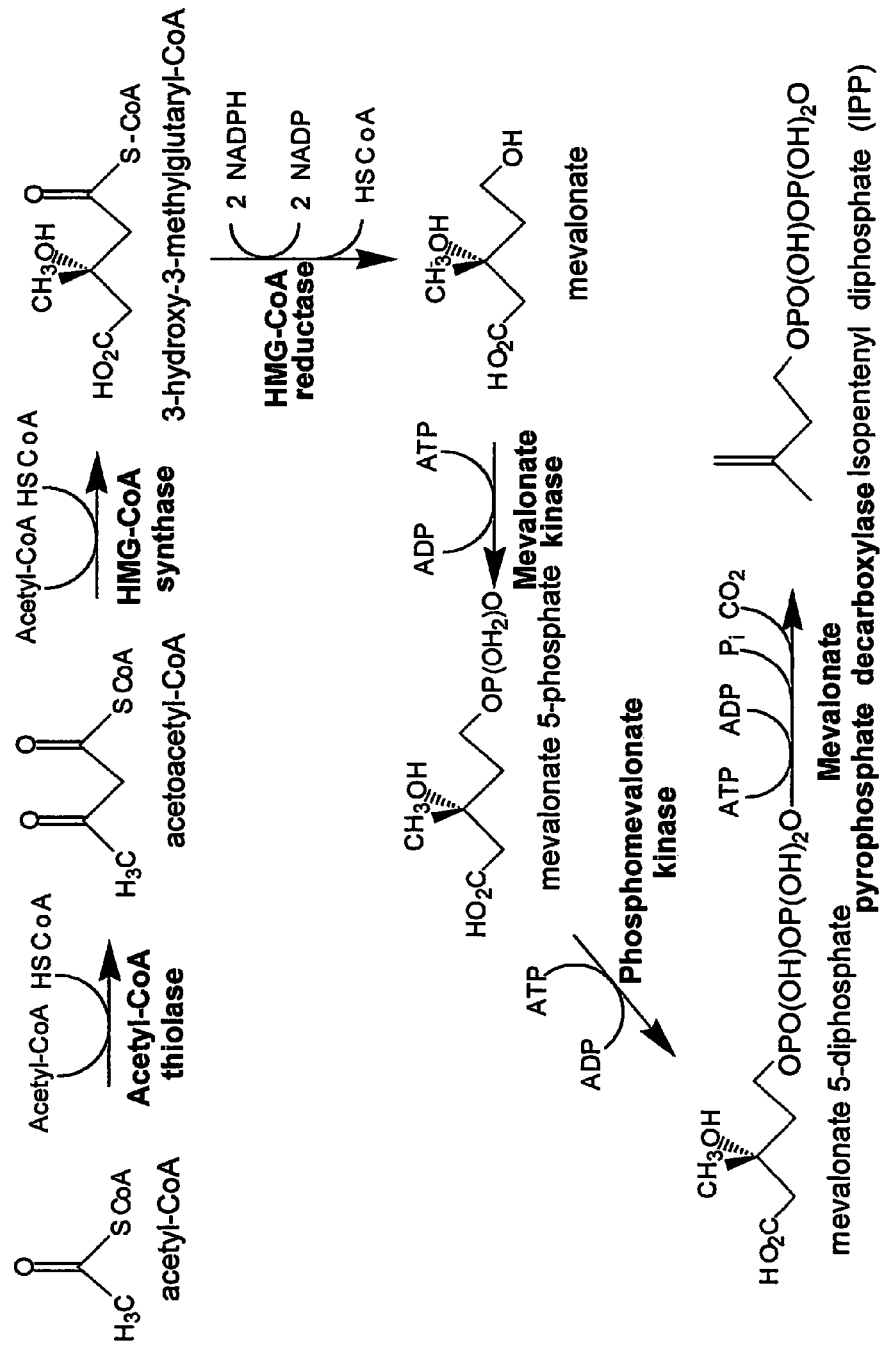
FIG. 2 is a schematic representation of the mevalonate (MEV) pathway for the production of IPP.
Figure 3:
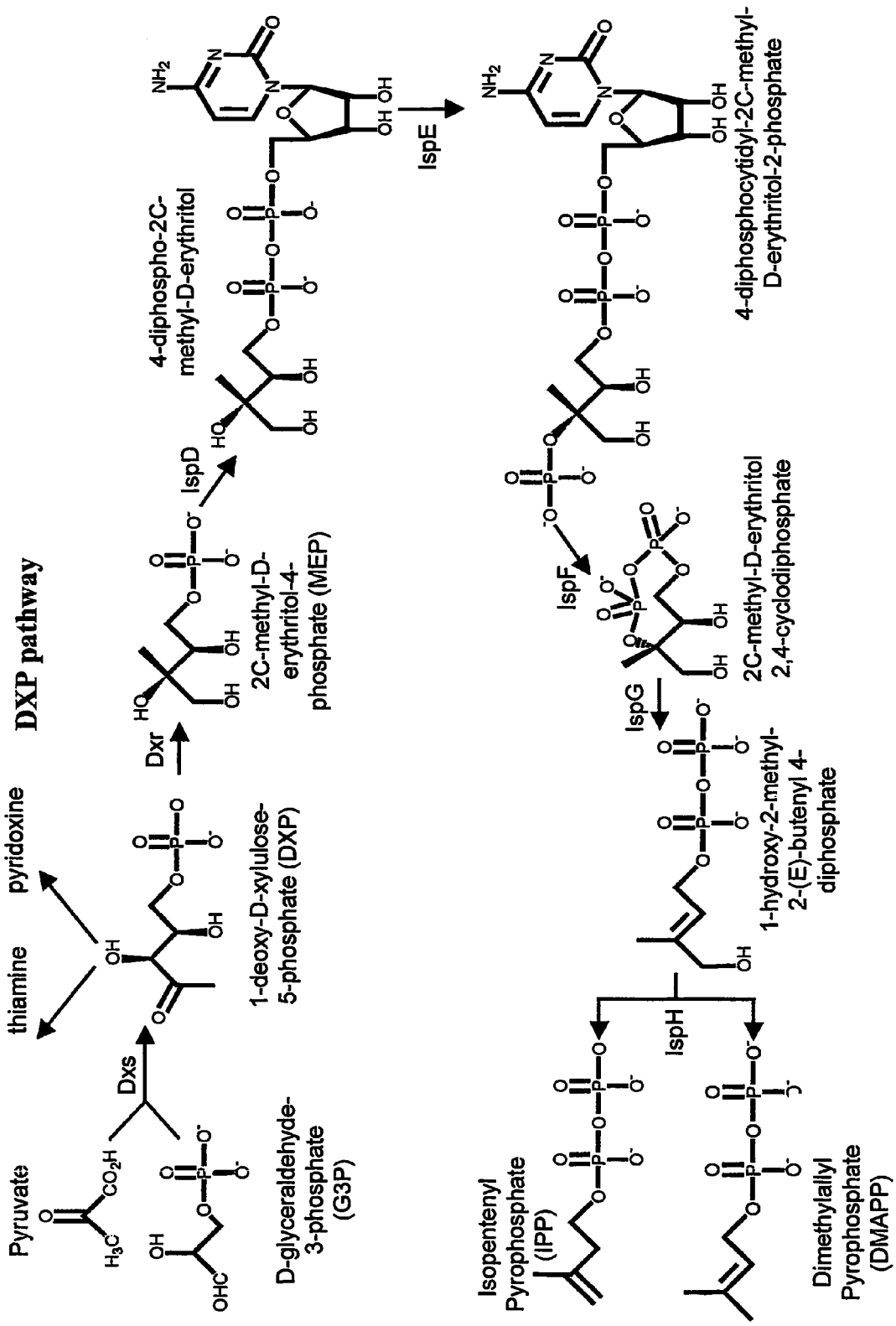
FIG. 3 is a schematic representation of the DXP pathway for the production of IPP and dimethylallyl pyrophosphate (DMAPP).

FIG. 1 depicts isoprenoid pathways involving modification of isopentenyl diphosphate (IPP) and/or its isomer dimethylallyl diphosphate (DMAPP) by prenyl transferases to generate the polyprenyl diphosphates geranyl diphosphate (GPP), farnesyl diphosphate (FPP), and geranylgeranyl diphosphate (GGPP). GPP and FPP are further modified by terpene synthases to generate monoterpenes and sesquiterpenes, respectively; and GGPP is further modified by terpene synthases to generate diterpenes and carotenoids. IPP and DMAPP are generated by one of two pathways: the mevalonate (V) pathway and the 1-deoxy-D-xylulose-5-phosphate (DXP) pathway. FIG. 2 depicts schematically the MEV pathway, where acetyl CoA is converted via a series of reactions to IPP. FIG. 3 depicts schematically the DXP pathway, in which pyruvate and D-glyceraldehyde-3-phosphate are converted via a series of reactions to IPP and DMAPP. Eukaryotic cells other than plant cells use the MEV isoprenoid pathway exclusively to convert acetyl-coenzyme A (acetyl-CoA) to IPP, which is subsequently isomerized to DMAPP. Plants use both the MEV and the mevalonate-independent, or DXP pathways for isoprenoid synthesis. Prokaryotes, with some exceptions, use the DXP pathway to produce IPP and DMAPP separately through a branch point.

Genetically Modified Host Cells

The present invention provides genetically modified host cells; libraries of genetically modified host cells; and compositions and kits comprising the genetically modified host cells. A subject genetically modified host cell is an isolated host cell that has been genetically modified with a nucleic acid(s) that comprises a nucleotide sequence(s) encoding a biosynthetic pathway enzyme(s); which genetically modified host cell produces the encoded biosynthetic pathway enzyme(s), which enzyme(s) results in conversion of a substrate for the enzyme into a biosynthetic pathway intermediate. When cultured in vitro under appropriate conditions, a subject genetically modified host cell produces a biosynthetic pathway intermediate in an amount that is effective to inhibit growth of the genetically modified host cell, or induce death of the genetically modified host cell. The genetically modified host cells are useful for identifying a gene product having activity in a biosynthetic pathway, as described in more detail below.

When cultured in vitro under appropriate conditions, a subject genetically modified host cell produces a biosynthetic pathway intermediate intracellularly in an amount that is greater than the amount of the biosynthetic pathway intermediate produced in a control cell, e.g., the same cell not genetically modified with one or more nucleic acids encoding a biosynthetic pathway enzyme(s). Thus, e.g., a subject genetically modified host cell produces at least about 10%, at least about 25%, at least about 50%, at least about 75%, at least about 2-fold, at least about 5-fold, or at least about 10-fold, or greater, more of the biosynthetic pathway intermediate than the amount of the biosynthetic pathway intermediate produced in a control cell, e.g., the same cell not genetically modified with one or more nucleic acids encoding a biosynthetic pathway enzyme(s). Whether a subject genetically modified host cell produces more of the biosynthetic pathway intermediate than a control cell is readily determined by measuring the level of the intermediate, using standard methods.

When cultured in vitro under appropriate conditions, a subject genetically modified host cell accumulates a biosynthetic pathway intermediate intracellularly in an amount that is toxic, e.g., growth inhibiting and/or death inducing. Whether a subject genetically modified host cell accumulates a biosynthetic pathway intermediate intracellularly in an amount that is growth inhibiting is readily determined by monitoring the optical density of a liquid culture of the genetically modified host cell. Whether a subject genetically modified host cell accumulates a biosynthetic pathway intermediate intracellularly in an amount that induces death of the genetically modified host cell is readily determined by monitoring the viability of the cells, e.g., by plating the cells on agar containing appropriate growth media at various times during culture of the cells, and counting the number of colonies formed (e.g., colony forming units, cfu).

The biosynthetic pathway enzymes produced by a subject genetically modified host cell are in some embodiments produced at a higher level than the level of such enzymes produced by a control cell, e.g., the same cell not genetically modified with one or more nucleic acids encoding a biosynthetic pathway enzyme(s). Thus, e.g., the biosynthetic pathway enzymes produced by a subject genetically modified host cell will in some embodiments be produced at a level that is at least 25%, at least 50%, at least 75%, at least 2-fold, or at least 5-fold, or more, higher than the level of such enzymes produced by a control cell, e.g., the same cell not genetically modified with one or more nucleic acids encoding a biosynthetic pathway enzyme(s).

In other embodiments, the biosynthetic pathway enzymes produced by a subject genetically modified host cell are catalytically more active than the enzymes produced by a control cell, e.g., the same cell not genetically modified with one or more nucleic acids encoding a biosynthetic pathway enzyme(s).

In some embodiments, a subject genetically modified host cell comprises one or more nucleic acids that comprise nucleotide sequences encoding one or more biosynthetic pathway enzyme(s); where the nucleic acids are maintained extrachromosomally, e.g., are maintained episomally. For example, in some embodiments, the nucleic acids are plasmids or other expression vectors that do not become integrated into the genome of the genetically modified host cell. In other embodiments, the nucleic acid is integrated into the genome of the genetically modified host cell. Integration includes multiple tandem integrations, multiple non-tandem integrations, targeted integration, and random integration.

Host Cells

Genetically modified host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like.

In other embodiments, the genetically modified host cell is a prokaryotic cell. Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995)

*Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like.

To generate a genetically modified host cell, one or more nucleic acids comprising nucleotide sequences encoding one or more biosynthetic pathway gene products is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In many embodiments, the nucleic acid with which the host cell is genetically modified is an expression vector that includes a nucleic acid comprising a nucleotide sequence that encodes a biosynthetic pathway enzyme. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). Thus, for example, a nucleic acid encoding a biosynthetic pathway gene product(s) is included in any one of a variety of expression vectors for expressing the biosynthetic pathway gene product(s). Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

The biosynthetic pathway gene product-encoding nucleotide sequence in the expression vector is operably linked to an appropriate expression control sequence(s) (promoter) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkuinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein— Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, recombinant expression vectors will include origins of replication and selectable markers permitting transformation of the host cell, e.g., the ampicillin resistance gene of *E. coli*, the *S. cerevisiae* TRP1 gene, etc.,; and a promoter derived from a highly-expressed gene to direct transcription of the biosynthetic pathway gene product-encoding sequence. Such promoters can be derived from operons encoding glycolytic enzymes such as 3-phosphoglycerate kinase (PGK), $\alpha$-factor, acid phosphatase, or heat shock proteins, among others.

In many embodiments, a genetically modified host cell is genetically modified with a nucleic acid that includes a nucleotide sequence encoding a biosynthetic pathway gene product, where the nucleotide sequence encoding a biosynthetic pathway gene product is operably linked to an inducible promoter. Inducible promoters are well known in the art. Suitable inducible promoters include, but are not limited to, the pL of bacteriophage $\lambda$; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177: 4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In many embodiments, a genetically modified host cell is genetically modified with a nucleic acid that includes a nucleotide sequence encoding a biosynthetic pathway gene product, where the nucleotide sequence encoding a biosynthetic pathway gene product is operably linked to a constitutive promoter. Suitable constitutive-promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. I, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

In some embodiments, a subject genetically modified host cell is one that is genetically modified with a nucleic acid comprising a nucleotide sequence encoding a single gene product in a biosynthesis pathway. In other embodiments, a subject host cell is genetically modified with a nucleic acid comprising nucleotide sequences encoding two or more gene products in a biosynthesis pathway. For example, the nucleic acid will in some embodiments comprise nucleotide sequences encoding the first and second enzymes in a biosynthetic pathway. In other embodiments, the nucleic acid will comprise nucleotide sequences encoding the first, second, and third enzymes in a biosynthetic pathway. In other embodiments, the nucleic acid will comprise nucleotide sequences encoding the second, third, and fourth enzymes in a biosynthetic pathway. In other embodiments, the nucleic acid will comprise nucleotide sequences encoding the third, fourth, and fifth enzymes in a biosynthetic pathway. In other embodiments, the nucleic acid will comprise nucleotide sequences encoding the fourth, fifth, and sixth enzymes in a biosynthetic pathway. In other embodiments, the nucleic acid will comprise nucleotide sequences encoding the first, third, and fifth enzymes in a biosynthetic pathway.

Where the host cell is genetically modified to express two or more gene products in a biosynthetic pathway, nucleotide sequences encoding the two or more gene products will in some embodiments each be contained on separate expression vectors. Where the host cell is genetically modified to express two or more gene products in a biosynthetic pathway, nucleotide sequences encoding the two or more gene products will in some embodiments be contained in a single expression vector. Where nucleotide sequences encoding the two or more gene products are contained in a single expression vector, in some embodiments, the nucleotide sequences will be operably linked to a common control element (e.g., a promoter), e.g., the common control element controls expression of all of the biosynthetic pathway gene product-encoding nucleotide sequences on the single expression vector.

In some embodiments, a nucleotide sequence encoding a biosynthetic pathway gene product will be operably linked to an inducible promoter. In other embodiments, a nucleotide sequence encoding a biosynthetic pathway gene product will be operably linked to a constitutive promoter. In some embodiments, where two or more biosynthetic pathway gene products are encoded by two or more nucleotide sequences, one of the nucleotide sequences will be operably linked to an inducible promoter, and one or more of the other nucleotide sequences will be operably linked to a constitutive promoter.

Host Cells Genetically Modified with a Nucleic Acid Encoding a Terpene Biosynthetic Pathway Enzyme A description of host cells genetically modified to express terpene biosynthetic pathway gene products follows. It should be noted that the following description is intended to provide an example, and is in no way limiting. In some embodiments, a subject genetically modified host cell is a prokaryotic host cell genetically modified with a nucleic acid comprising a nucleotide sequence encoding gene product(s) in the terpene biosynthesis pathway. In some embodiments, a subject genetically modified host cell is a eukaryotic host cell genetically modified with a nucleic acid comprising a nucleotide sequence encoding gene product(s) in the terpene biosynthesis pathway.

Toxic intermediates (e.g., intermediates that are cell growth inhibiting and/or cell death inducing when accumulated in a subject genetically modified host cell) in a terpene biosynthetic pathway include, but are not limited to, HMG-CoA, IPP, DMAPP, and a polyprenyl diphosphate (e.g., GPP, FPP, GGPP, GFPP, HexPP, HepPP, OPP, SPP, DPP, NPP, UPP, etc.).

In some embodiments, a subject genetically modified host cell is one that is genetically modified with one or more nucleic acids comprising nucleotide sequences encoding gene products that are active in the MEV pathway. In some embodiments, where a subject genetically modified host cell is one that is genetically modified with a nucleic acid comprising a nucleotide sequence encoding gene product(s) in the MEV pathway, the host cell is one that lacks endogenous genes encoding MEV pathway enzymes. In other embodiments, the host cell has a functional endogenous MEV pathway; however, the endogenous MEV pathway does not produce levels of a terpene biosynthetic pathway intermediate that are growth inhibiting or toxic.

In other embodiments, a subject genetically modified host cell is one that is genetically modified with one or more nucleic acids comprising nucleotide sequences encoding gene products that are active in the DXP pathway. In some embodiments, where a subject genetically modified host cell is one that is genetically modified with a nucleic acid comprising a nucleotide sequence encoding gene product(s) in the DXP pathway, the host cell is one that lacks endogenous genes encoding DXP pathway enzymes. In other embodiments, the host cell has a functional endogenous DXP pathway; however, the endogenous DXP pathway does not produce levels of a terpene biosynthetic pathway intermediate that are growth inhibiting or toxic.

In some embodiments, each terpene biosynthetic pathway gene product is encoded on a separate nucleic acid. In other embodiments, two or more terpene biosynthetic pathway gene products are encoded on one expression vector. For example, in some embodiments, nucleotide sequences encoding acetoacetyl-CoA thiolase, HMGS, HMGR, MK, PMK, MPD, and IDI are present on separate nucleic acids, e.g., on separate expression vectors. In other embodiments, nucleotide sequences encoding two or more of acetoacetyl-CoA thiolase, HMGS, HMGR, MK, PMK, MPD, and IDI are present on a single nucleic acid, e.g., on a single expression vector. As another example, in some embodiments, nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase are present on separate nucleic acids. In other embodiments, nucleotide sequences encoding two or more of 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase are present on a single nucleic acid, e.g., on a single expression vector.

In some embodiments, a nucleotide sequence encoding a biosynthetic pathway gene product will be operably linked to an inducible promoter. In other embodiments, a nucleotide sequence encoding a biosynthetic pathway gene product will be operably linked to a constitutive promoter. In some embodiments, where two or more biosynthetic pathway gene products are encoded by two or more nucleotide sequences, one of the nucleotide sequences will be operably linked to an inducible promoter, and one or more of the other nucleotide sequences will be operably linked to a constitutive promoter. For example, in some embodiments, where one or more nucleic acids comprising nucleotide sequences encoding one or more of 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase are used to genetically modified a host cell, one nucleotide sequence (e.g., the nucleotide sequence encoding 1-deoxy-D-xylulose-5-phosphate synthase) is operably linked to an inducible promoter, and the nucleotide sequences encoding one or more of 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase are operably linked to constitutive promoters. As another non-limiting example, in some embodiments, where one or more nucleic acids comprising nucleotide sequences encoding one or more of acetoacetyl-CoA thiolase, HMGS, HMGR, MK, PMK, MPK, and IDI are used to genetically modified a host cell, one nucleotide sequence, one nucleotide sequence (e.g., the nucleotide sequence encoding acetoacetyl-CoA thiolase, or the nucleotide sequence encoding MK) is operably linked to an inducible promoter, and the nucleotide sequences encoding one or more of the other MEV pathway enzymes are operably linked to a constitutive promoter.

In some embodiments, two or more of the terpene biosynthetic pathway enzymes are arranged in a single transcription unit (an "operon"). In some of these embodiments, the nucleotide sequences in the operon that encode the terpene biosynthetic pathway enzymes are operably linked to an inducible promoter. In other embodiments, the nucleotide sequences in the operon that encode the terpene biosynthetic pathway enzymes are operably linked to a constitutive promoter. See, e.g., FIG. 13, for exemplary, non-limiting examples of such operons.

MEV Pathway

In some embodiments, a subject genetically modified host cell is one that is genetically modified with one or more nucleic acids comprising nucleotide sequences encoding gene products that are active in the MEV pathway (FIG. 2). In some embodiments, each of the MEV pathway gene products is encoded on separate nucleic acids. In other embodiments, two or more MEV pathway gene products are encoded on a single nucleic acid. In some embodiments, each terpene biosynthetic pathway gene product is encoded on a separate nucleic acid. In other embodiments, two or more terpene biosynthetic pathway gene products are encoded on one expression vector. For example, in some embodiments, nucleotide sequences encoding acetoacetyl-CoA thiolase, HMGS, HMGR, MK, PMK, MPD, and IDI are present on separate nucleic acids. In other embodiments, nucleotide sequences encoding two or more of acetoacetyl-CoA thiolase, HMGS, HMGR, MK, PMK, MPD, and IDI are present on a single nucleic acid, e.g., on a single expression vector.

In some embodiments, a subject genetically modified host cell is one that is genetically modified with a nucleic acid comprising nucleotide sequences encoding acetoacetyl-CoA thiolase, hydroxymethylglutaryl-CoA synthase (HMGS), and hydroxymethylglutaryl-CoA reductase (HMGR), which are the first three enzymes of the mevalonate (MEV) pathway of terpene synthesis (see FIG. 2), and which will generate synthesis of mevalonate. In other embodiments, a subject genetically modified host cell is one that is genetically modified with a nucleic acid comprising nucleotide sequences encoding mevalonate kinase (MK), phosphomevalonate kinase (PMK), and mevalonate pyrophosphate decarboxylase (MPD), which are the last three enzymes in the terpene biosynthetic pathway, and will yield IPP (see FIG. 2). In other embodiments, a subject genetically modified host cell is one that is genetically modified with a nucleic acid comprising nucleotide sequences encoding MK, PMK, MPD, and isopentenyl diphosphate isomerase (IDI).

In other embodiments, a subject genetically modified host cell is one that is genetically modified with a first nucleic acid comprising nucleotide sequences encoding acetoacetyl-CoA thiolase, HMGS, and HMGR; and a second nucleic acid comprising nucleotide sequences encoding MK, PMK, and MPD. In other embodiments, a host cell is genetically modified with a first nucleic acid comprising nucleotide sequences encoding acetoacetyl-CoA thiolase, HMGS, and HMGR; and a second nucleic acid comprising nucleotide sequences encoding MK, PMK, MPD, and IDI. In other embodiments, a subject genetically modified host cell is one that is genetically modified with a nucleic acid comprising nucleotide sequences encoding acetoacetyl-CoA thiolase, HMGS, HMGR, MK, PMK, and MPD. In other embodiments, a subject genetically modified host cell is one that is genetically modified with a nucleic acid comprising nucleotide sequences encoding acetoacetyl-CoA thiolase, HMGS, HMGR, MK, PMK, MPD, and IDI. In particular embodiments of interest, the genetically modified host cell is a prokaryotic cell.

In particular embodiments of interest, the genetically modified host cell is a prokaryotic cell that is genetically modified with nucleic acids encoding MEV pathway gene products. Thus, in some embodiments, a subject genetically modified host cell is a prokaryotic cell (e.g., E. coli) that is genetically modified with a nucleic acid that comprises nucleotide sequences encoding acetoacetyl-CoA thiolase, HMGS, and HMGR In other embodiments, a subject genetically modified host cell is a prokaryotic cell (e.g., E. coli) that is genetically modified with a nucleic acid that comprises nucleotide sequences encoding MK, PMK, and MPD. In other embodiments, a subject genetically modified host cell is a prokaryotic cell (e.g., E. coli) that is genetically modified with a nucleic acid that comprises nucleotide sequences encoding MK, PMK, MPD, and IDI. In other embodiments, a subject genetically modified host cell is a prokaryotic cell (e.g., E. coli) that is genetically modified with a first nucleic acid comprising nucleotide sequences encoding acetoacetyl-CoA thiolase, HMGS, and HMGR; and a second nucleic acid comprising nucleotide sequences encoding MK, PMK, and MPD. In other embodiments, a subject genetically modified host cell is a prokaryotic cell (e.g., E. coli) that is genetically modified with a first nucleic acid comprising nucleotide sequences encoding acetoacetyl-CoA thiolase, HMGS, and HMGR; and a second nucleic acid comprising nucleotide sequences encoding MK, PMK, MPD, and IDI. In other embodiments, a subject genetically modified host cell is a prokaryotic cell (e.g., E. coli) that is genetically modified with a nucleic acid comprising nucleotide sequences encoding acetoacetyl-CoA thiolase, HMGS, HMGR, MK, PMK, and MPD. In other embodiments, a subject genetically modified host cell is prokaryotic cell (e.g., E. coli) that is genetically modified with a nucleic acid comprising nucleotide sequences encoding acetoacetyl-CoA thiolase, HMGS, HMGR, MK, PMK, MPD, and IDI.

Typically, as discussed above, a nucleic acid comprising a nucleotide sequence encoding a MEV pathway gene product is an expression vector. A wide variety of expression vectors are known in the art, and a number of suitable expression vectors are discussed hereinabove. In many embodiments, the expression vector is one that is suitable for use in prokaryotic cells. In some embodiments, a nucleotide sequence encoding a MEV pathway gene product, where the MEV pathway gene product-encoding nucleotide sequence is operably linked to (e.g., under the transcriptional control of) an inducible promoter. Inducible promoters are well known in the art, and a number of suitable inducible promoters are discussed hereinabove.

In some embodiments, a subject genetically modified host cell is a prokaryotic cell (e.g., E. coli) that is genetically modified with a nucleic acid that comprises a nucleotide sequence encoding acetoacetyl-CoA thiolase, HMGS, and HMGR, where the nucleotide sequence is operably linked to an inducible promoter, where the nucleic acid is an expression vector suitable for use to effect expression of a nucleic acid in a prokaryotic cell. In some embodiments, a subject genetically modified host cell is a prokaryotic cell (e.g., E. coli) that is genetically modified with a nucleic acid that comprises a nucleotide sequence encoding MK, PMK, and MPD, where the nucleotide sequence is operably linked to an inducible promoter, where the nucleic acid is an expression vector suitable for use to effect expression of a nucleic acid in a prokaryotic cell. In some embodiments, a subject genetically modified host cell is a prokaryotic cell (e.g., E. coli) that is genetically modified with a nucleic acid that comprises a nucleotide sequence encoding N, PMK, MPD, and IDI, where the nucleotide sequence is operably linked to an inducible promoter, where the nucleic acid is an expression vector suitable for use to effect expression of a nucleic acid in a prokaryotic cell. In some embodiments, a subject genetically modified host cell is a prokaryotic cell (e.g., E. coli) that is genetically modified with a first nucleic acid that comprises a nucleotide sequence encoding acetoacetyl-CoA thiolase, HMGS, and HMGR, where the nucleotide sequence is operably linked to an inducible promoter, where the nucleic acid is an expression vector suitable for use to effect expression of a nucleic acid in a prokaryotic cell; and a second nucleic acid that comprises a nucleotide sequence encoding MK, PMK, and MPD, where the nucleotide sequence is operably linked to an inducible promoter, where the nucleic acid is an expression vector suitable for use to effect expression of a nucleic acid in a prokaryotic cell. In some embodiments, a subject genetically modified host cell is a prokaryotic cell (e.g., E. coli) that is genetically modified with a first nucleic acid that comprises a nucleotide sequence encoding acetoacetyl-CoA thiolase, HMGS, and HMGR, where the nucleotide sequence is operably linked to an inducible promoter, where the nucleic acid is an expression vector suitable for use to effect expression of a nucleic acid in a prokaryotic cell; and a second nucleic acid that comprises a nucleotide sequence encoding MK, PMK, MPD, and IDI, where the nucleotide sequence is operably linked to an inducible promoter, where the nucleic acid is an expression vector suitable for use to effect expression of a nucleic acid in a prokaryotic cell. In some embodiments, the inducible promoter is a $P_{LAC}$ promoter.

In some of these embodiments, the nucleotide sequences are arranged in a single transcription unit (an "operon"). See, e.g., FIG. 13. For example, in some embodiments, a subject genetically modified host cell is a prokaryotic cell (e.g., E. coli) that is genetically modified with a nucleic acid comprising nucleotide sequences that encode acetoacetyl-CoA thiolase, HMGS, and HMGR, arranged in a single transcription unit and operably linked to an inducible promoter. In some embodiments, a subject genetically modified host cell is a prokaryotic cell (e.g., E. coli) that is genetically modified with a nucleic acid comprising nucleotide sequences that encode MK, PMK, and MPD, arranged in a single transcription unit and operably linked to an inducible promoter. In some embodiments, a subject genetically modified host cell is a prokaryotic cell (e.g., E. coli) that is genetically modified with a nucleic acid comprising nucleotide sequences that encode MK, PMK, MPD, and IDI arranged in a single transcription unit and operably linked to an inducible promoter. In other embodiments, a subject genetically modified host cell is a prokaryotic cell (e.g., E. coli) that is genetically modified with two of the above-described operons.

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; E. coli), (D49362; Paracoccus denitrificans); and (L20428; Saccharomyces cerevisiae); HMGS: (NC_001145. complement 19061 . . . 20536; Saccharomyces cerevisiae), (X96617; Saccharomyces cerevisiae), (X83882; Arabidopsis thaliana), (AB037907; Kitasatospora griseola), and (BT007302; Homo sapiens); HMGR: (NM_206548; Drosophila melanogaster), (NM_204485; Gallus gallus), (AB015627; Streptomyces sp. KO-3988), (AF542543; Nicotiana attenuata), (AB037907; Kitasatospora griseola), (AX128213, providing the sequence encoding a truncated HMGR; Saccharomyces cerevisiae), and (NC_001145: complement (115734 . . . 118898; Saccharomyces cerevisiae)); MK: (L77688; Arabidopsis thaliana), and (X55875; Saccharomyces cerevisiae); PMK: (AF429385; Hevea brasiliensis), (NM_06556; Homo sapiens), (NC_001145. complement 712315 . . . 713670; Saccharomyces cerevisiae); MPD: (X97557; Saccharomyces cerevisiae), (AF290095; Enterococcus faecium), and (U49260; Homo sapiens); and IDI: (NC_000913, 3031087 . . . 3031635; E. coli), and (AF082326; Haematococcus pluvialis).

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

DXP Pathway

In some embodiments, a subject genetically modified host cell is one that is genetically modified with one or more nucleic acids comprising nucleotide sequences encoding gene products that are active in the DXP pathway (FIG. 3). In some embodiments, each of the DXP pathway gene products is encoded on separate nucleic acids. In other embodiments, two or more DXP pathway gene products are encoded on a single nucleic acid. In general, the DXP pathway gene product-encoding nucleic acids are expression vectors. In many embodiments, the nucleotide sequences encoding DXP pathway gene products are operably linked to an inducible promoter.

For example, in some embodiments, a subject genetically modified host cell is one that is genetically modified with one or more nucleic acids comprising nucleotide sequences encoding 1-deoxy-D-xylulose-5-phosphate synthase ("Dxs"), 1-deoxy-D-xylulose-5-phosphate reductoisomerase ("IspC"), 4-diphosphocytidyl-2-C-methyl-D-erythritol synthase ("IspD"), 4-diphosphocytidyl-2-C-methyl-D-erythritol kinase ("IspE"), 2C-methyl-D-erythritol 2,4-cyclodiphosphate synthase ("IspF"), 1-hydroxy-2-methyl-2-(E)-butenyl 4-diphosphate synthase ("IspG"), and isopentenyl/dimethylallyl diphosphate synthase ("IspH") (DXP pathway enzymes 1-7). In other embodiments, a subject genetically modified host cell is one that is genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-E)-butenyl 4-diphosphate synthase, and isopentenyl/dimethylallyl diphosphate synthase (DXP pathway enzymes 3-7).

In particular embodiments of interest, the genetically modified host cell is a eukaryotic cell (e.g., a yeast cell). Thus, in some embodiments, a subject genetically modified host cell is a eukaryotic cell (e.g., a yeast cell) that is genetically modified with one or more nucleic acids comprising nucleotide sequences encoding 1-deoxy-D-xylulose-5-phosphate synthase ("Dxs"), 1-deoxy-D-xylulose-5-phosphate reductoisomerase ("IspC"), 4-diphosphocytidyl-2-C-methyl-D-erythritol synthase ("IspD"), 4-diphosphocytidyl-2-C-methyl-D-erythritol kinase ("IspE"), 2C-methyl-D-erythritol 2,4-cyclodiphosphate synthase ("IspF"), 1-hydroxy-2-methyl-2-(E)-butenyl 4-diphosphate synthase ("IspG"), and isopentenyl/dimethylallyl diphosphate synthase ("IspH") (DXP pathway enzymes 1-7). In other embodiments, a subject genetically modified host cell is a eukaryotic cell (e.g., a yeast cell) that is genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase (DXP pathway enzymes 3-7).

Prenyl Transferases

In some embodiments, a subject genetically modified host cell is genetically modified to include one or more nucleic acids comprising a nucleotide sequence(s) encoding one or more terpene biosynthetic pathway gene products (e.g., a MEV pathway enzyme, or a DXP pathway enzyme), as described above; and a nucleic acid comprising a nucleotide sequence that encodes a prenyl transferase. In these embodiments, the genetically modified host cell synthesizes a prenyl transferase whose product is growth inhibiting for the genetically modified host cell.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 5 isoprene units to about 6000 isoprene units or more, e.g., from about 5 isoprene units to about 10 isoprene units, from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50-isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; Homo sapiens); farnesyl diphosphate synthetase (FPP) gene (GenBank Accession No. J05091; Saccharomyces cerevisiae); isopentenyl diphosphate:dimethylallyl diphosphate isomerase gene (J05090; *Saccharomyces cerevisiae*); Wang and Ohnuma (2000) *Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

In some embodiments, a host cell is genetically modified with a nucleic acid comprising nucleotide sequences encoding mevalonate kinase, phosphomevalonate kinase, mevalonate pyrophosphate decarboxylase, isopentenyl pyrophosphate isomerase, and a prenyl transferase. For example, in some embodiments, a host cell is genetically modified with a nucleic acid comprising nucleotide sequences encoding mevalonate kinase, phosphomevalonate kinase, mevalonate pyrophosphate decarboxylase, isopentenyl pyrophosphate isomerase, and a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. As one non-limiting example, in some embodiments, a host cell is genetically modified with a nucleic acid comprising nucleotide sequences encoding mevalonate kinase, phosphomevalonate kinase, mevalonate pyrophosphate decarboxylase, isopentenyl pyrophosphate isomerase, and a farnesyl pyrophosphate synthase.

In other embodiments, a host cell is genetically modified with a first nucleic acid comprising nucleotide sequences encoding acetoacetyl-CoA thiolase, hydroxymethylglutaryl-CoA synthase, and hydroxymethylglutaryl-CoA reductase; and a second nucleic acid comprising nucleotide sequences encoding encoding mevalonate kinase, phosphomevalonate kinase, mevalonate pyrophosphate decarboxylase, isopentenyl pyrophosphate isomerase, and a prenyl transferase. For example, in some embodiments, a host cell is genetically modified with a first nucleic acid comprising nucleotide sequences encoding acetoacetyl-CoA thiolase, hydroxymethylglutaryl-CoA synthase, and hydroxymethylglutaryl-CoA reductase; and a second nucleic acid comprising nucleotide sequences encoding encoding mevalonate kinase, phosphomevalonate kinase, mevalonate pyrophosphate decarboxylase, isopentenyl pyrophosphate isomerase, and a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. As one non-limiting example, in some embodiments, a host cell is genetically modified with a first nucleic acid comprising nucleotide sequences encoding acetoacetyl-CoA thiolase, hydroxymethylglutaryl-CoA synthase, and hydroxymethylglutaryl-CoA reductase; and a second nucleic acid comprising nucleotide sequences encoding encoding mevalonate kinase, phosphomevalonate kinase, mevalonate pyrophosphate decarboxylase, isopentenyl pyrophosphate isomerase, and a farnesyl pyrophosphate synthase.

In some embodiments, a host cell is genetically modified with one or more nucleic acids comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, isopentenyl/dimethylallyl diphosphate synthase, and a prenyl transferase. For example, in some embodiments, a host cell is genetically modified with one or more nucleic acids comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, isopentenyl/dimethylallyl diphosphate synthase, and a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase.

In some embodiments, a host cell is genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and a prenyl transferase. For example, in some embodiments, a host cell is genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase.

Codon Usage

In some embodiments, the nucleotide sequence encoding a biosynthetic pathway gene product is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Additional Genetic Modifications

In some embodiments, a subject genetically modified host cell is one that is genetically modified to include one or more nucleic acids comprising a nucleotide sequence(s) that encode terpene biosynthetic pathway gene product(s); and that is further genetically modified to achieve enhanced production of a terpene biosynthetic pathway intermediate, and/or that is further genetically modified such that an endogenous terpene biosynthetic pathway gene is functionally disabled. The term "functionally disabled," as used herein in the context of an endogenous terpene biosynthetic pathway gene, refers to a genetic modification of a terpene biosynthetic pathway gene, which modification results in production of a gene product encoded by the gene that is produced at below normal levels, and/or is non-functional.

Genetic modifications that enhance production of an endogenous terpene biosynthetic pathway intermediate include, but are not limited to, genetic modifications that result in a reduced level and/or activity of a phosphotransacetylase in the host cell. The intracellular concentration of a terpene biosynthetic pathway intermediate is enhanced by increasing the intracellular concentration of acetyl-CoA. *E. coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the genetically modified host cell is one that is genetically modified with a nucleic acid comprising nucleotide sequences encoding one or more MEV pathway gene products.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like.

In some embodiments, the endogenous pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci USA* 97(12): p. 6640-5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

In some embodiments, a subject genetically modified host cell is one that is genetically modified to include one or more nucleic acids comprising a nucleotide sequence(s) that encode MEV biosynthetic pathway gene product(s); and that is further genetically modified such that an endogenous DXP biosynthetic pathway gene is functionally disabled. In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, where subject genetically modified host cell is a prokaryotic host cell that is genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

In other embodiments, where subject genetically modified host cell is a prokaryotic host cell that is genetically modified with nucleic acid(s) comprising nucleotide sequences encoding one or more DXP pathway gene products, the host cell will be further genetically modified such that one or more endogenous MEV pathway genes is functionally disabled. Endogenous MEV pathway genes that can be functionally disabled include one or more of the genes encoding any of the following MEV gene products: HMGS, HMGR, MK, PMK, MPD, and IDI. An endogenous MEV pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Compositions Comprising a Subject Genetically Modified Host Cell

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Genetically Modified Host Cell Libraries

The present invention provides a genetically modified host cell library. A subject genetically modified host cell library comprises at least two members, each of which members comprises a different nucleic acid(s) comprising a nucleotide sequence encoding a different biosynthetic pathway enzyme(s). In many embodiments, the genetically modified host cells in a subject library are microbial cells. In some embodiments, the cells are eukaryotic cells (e.g., yeast cells, algal cells, mammalian cells, etc., as described supra), that can be grown in in vitro cell culture as unicellular entities. In other embodiments, the cells are prokaryotic cells, e.g., bacterial cells.

A subject genetically modified host cell library includes from about 2 member genetically modified host cells to about 50 member genetically modified host cells, each of which member host cell comprises a nucleic acid comprises a nucleotide sequence encoding a different biosynthetic pathway enzyme, e.g., a subject genetically modified host cell library includes from about 2 member genetically modified host cells to about 4 member genetically modified host cells, from about 4 member genetically modified host cells to about 6 member genetically modified host cells, from about 6 member genetically modified host cells to about 8 member genetically modified host cells, from about 8 member genetically modified host cells to about 10 member genetically modified host cells, from about 10 member genetically modified host cells to about 12 member genetically modified host cells, from about 12 member genetically modified host cells to about 14 member genetically modified host cells, from about 14 member genetically modified host cells to about 16 member genetically modified host cells, from about 16 member bacteria to about 18 member genetically modified host cells, from about 18 member genetically modified host cells to about 20 member genetically modified host cells, or from about 20 member genetically modified host cells to about 50 genetically modified host cells, or more, each of which member genetically modified host cells comprises a nucleic acid comprises a nucleotide sequence encoding a different biosynthetic pathway enzyme from other member genetically modified host cells.

Typically, a plurality of each member host cell is present in the library, e.g., a subject genetically modified host cell library comprises two or more member host cells, where from about 10 to about $10^2$, from about $10^2$ to about $10^4$, from about $10^4$ to about $10^6$, or from about $10^6$ to about $10^8$ or more of each member genetically modified host cells is present in the library.

In some embodiments, a subject genetically modified host cell library comprises two or more member genetically modified host cells, each of which genetically modified host cells comprises a different enzyme in a terpene biosynthetic pathway. The following are non-limiting examples.

Genetically Modified Prokaryotic Host Cell Libraries

In some embodiments, a subject genetically modified host cell library is a genetically modified bacterial library. A subject genetically modified bacterial library includes from about 2 member bacteria to about 50 member bacteria, each of which member bacteria comprises a nucleic acid comprises a nucleotide sequence encoding a different prenyl synthase, e.g., a subject genetically modified bacterial library includes from about 2 member bacteria to about 4 member bacteria, from about 4 member bacteria to about 6 member bacteria, from about 6 member bacteria to about 8 member bacteria, from about 8 member bacteria to about 10 member bacteria, from about 10 member bacteria to about 12 member bacteria, from about 12 member bacteria to about 14 member bacteria, from about 14 member bacteria to about 16 member bacteria, from about 16 member bacteria to about 18 member bacteria, from about 18 member bacteria to about 20 member bacteria, or from about 20 member bacteria to about 50 member bacteria, or more, each of which member genetically modified bacteria comprises a nucleic acid comprises a nucleotide sequence encoding a different prenyl synthase from the other member bacteria. Typically, a plurality of each member genetically modified bacterium is present in the population, e.g., a subject genetically modified bacterial library comprises two or more member bacteria, where from about 10 to about $10^2$, from about $10^2$ to about $10^4$, from about $10^4$ to about $10^6$, or from about $10^6$ to about $10^8$ or more of each member genetically modified bacterium is present in the library.

In some embodiments, a subject genetically modified host cell library includes at least two member bacteria, each of which comprises one or more nucleic acids comprising a nucleotide sequence encoding mevalonate kinase (MK), phosphomevalonate kinase (PMK), mevalonate pyrophosphate decarboxylase (MPD), and isoprenyl diphosphate isomerase (IDI); and a further nucleic acid comprising a nucleotide sequence encoding a different prenyl transferase from other member bacteria. In other embodiments, a subject genetically modified host cell library includes at least two member bacteria, each of which comprises one or more nucleic acids comprising a nucleotide sequence encoding acetoacetyl-CoA thiolase, hydroxymethylglutaryl-CoA synthase (HMGS), and hydroxymethylglutaryl-CoA reductase (HMGR); a further nucleic acid comprising a nucleotide sequence encoding MK, PMK, MPD, and IDI; and a third nucleic acid comprising a nucleotide sequence encoding a different prenyl transferase from other member bacteria. In other embodiments, a subject genetically modified host cell library includes at least two member bacteria, each of which comprises one or more nucleic acids comprising a nucleotide sequence encoding acetoacetyl-CoA thiolase, HMGS, HMGR, MK, PMK, MPD, and IDI; and a further nucleic acid comprising a nucleotide sequence encoding a different prenyl transferase from other member bacteria.

In some embodiments, each of the member bacteria comprises a first nucleic acid, where the first nucleic acid is a single nucleic acid comprising nucleotide sequences encoding MK, PMK, MPD, and IDI, and where the nucleotide sequences encoding MK, PMK, MPD, and IDI are operably linked to a common control element; and a second nucleic acid comprising a nucleotide sequence encoding a prenyl transferase. In some embodiments, each of the member bacteria comprise a first nucleic acid, where the first nucleic acid is a single nucleic acid comprising nucleotide sequences encoding MK, PMK, MPD, and IDI, where the nucleotide sequences encoding MK, PMK, MPD, and IDI are operably linked to a common control element, and where the control element is an inducible promoter; and a second nucleic acid comprising a nucleotide sequence encoding a prenyl transferase.

In some embodiments, each of the member genetically modified bacteria comprises a first nucleic acid, where the first nucleic acid is a single nucleic acid comprising nucleotide sequences encoding acetoacetyl-CoA thiolase, HMGS, and HMGR, and where the nucleotide sequences encoding acetoacetyl-CoA thiolase, HMGS, and HMGR are operably linked to a common control element. In some embodiments, each of the member genetically modified bacteria comprise a first nucleic acid, where the first nucleic acid is a single nucleic acid comprising nucleotide sequences encoding acetoacetyl-CoA thiolase, HMGS, and HMGR, where the nucleotide sequences encoding acetoacetyl-CoA thiolase, HMGS, and HMGR are operably linked to a common control element, and where the control element is an inducible promoter.

In some embodiments, a subject genetically modified host cell library includes at least two member bacteria, each of which comprises one or more nucleic acids comprising a nucleotide sequence encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase ("DXP pathway enzymes 1-6"); and a further nucleic acid comprising a nucleotide sequence encoding a different prenyl transferase from other member bacteria. In some embodiments, a subject genetically modified host cell library includes at least two member bacteria, each of which comprises one or more nucleic acids comprising a nucleotide sequence encoding DXP pathway enzymes 1-6 and isopentenyl/dimethylallyl diphosphate synthase; and a further nucleic acid comprising a nucleotide sequence encoding a different prenyl transferase from other member bacteria. In other embodiments, a subject genetically modified host cell library includes at least two member bacteria, each of which comprises one or more nucleic acids comprising a nucleotide sequence encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase ("DXP pathway enzymes 3-6"); and a further nucleic acid comprising a nucleotide sequence encoding a different prenyl transferase from other member bacteria. In other embodiments, a subject genetically modified host cell library includes at least two member bacteria, each of which comprises one or more nucleic acids comprising a nucleotide sequence encoding DXP pathway enzymes 3-6 and isopentenyl/dimethylallyl diphosphate synthase; and a further nucleic acid comprising a nucleotide sequence encoding a different prenyl transferase from other member bacteria. In some embodiments, DXP enzyme pathways 1-6 (and optionally also isopentenyl/dimethylallyl diphosphate synthase), or DXP enzyme pathways 3-6 (and optionally also isopentenyl/dimethylallyl diphosphate synthase), are encoded by nucleotide sequences that are operably linked to a common control element, e.g., an inducible promoter.

For example, a subject genetically modified bacterial library comprises two or more members each member comprising a nucleic acid comprising a nucleotide sequence encoding a different prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase.

The following are non-limiting examples of a subject genetically modified host cell library, where the genetically modified host cells are bacteria. In some embodiments, a subject genetically modified bacterial library comprises at least two member genetically modified bacteria, the first member bacterium comprising a nucleic acid comprising nucleotide sequences encoding MK, PMK, MPD, and IDI, and a nucleic acid comprising a nucleotide sequence encoding an FPP synthase; and the second member bacterium comprising a nucleic acid comprising nucleotide sequences encoding MK, PMK, MPD, and IDI, and a nucleic acid comprising a nucleotide sequence encoding a GPP synthase.

In other embodiments, a subject genetically modified bacterial library comprises at least three member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; and the third member bacterium comprising a nucleic acid comprising nucleotide sequences encoding MK, PMK, MPD, and IDI, and a nucleic acid comprising a nucleotide sequence encoding a GGPP synthase.

In other embodiments, a subject genetically modified bacterial library comprises at least four member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; and the fourth member bacterium comprising a nucleic acid comprising nucleotide sequences encoding MK, PMK, MPD, and IDI, and a nucleic acid comprising a nucleotide sequence encoding a HexPP synthase.

In other embodiments, a subject genetically modified bacterial library comprises at least five member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; and the fifth member bacterium comprising a nucleic acid comprising nucleotide sequences encoding MK, PMK, MPD, and IDI, and a nucleic acid comprising a nucleotide sequence encoding a HepPP synthase.

In other embodiments, a subject genetically modified bacterial library comprises at least six member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; the fifth member bacterium comprising a nucleic acid comprising nucleotide sequences encoding MK, PMK, MPD, and IDI, and a nucleic acid comprising a nucleotide sequence encoding a HepPP synthase and the sixth member bacterium comprising a nucleic acid comprising nucleotide sequences encoding MK, PMK, MPD, and IDI, and a nucleic acid comprising a nucleotide sequence encoding an OPP synthase.

In other embodiments, a subject genetically modified bacterial library comprises at least seven member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; the fifth member bacterium comprising a nucleic acid comprising nucleotide sequences encoding MK, PMK, MPD, and IDI, and a nucleic acid comprising a nucleotide sequence encoding a HepPP synthase the sixth member bacterium comprising a nucleic acid comprising nucleotide sequences encoding MK, PMK, MPD, and IDI, and a nucleic acid comprising a nucleotide sequence encoding an OPP synthase; and the seventh member bacterium comprising a nucleic acid comprising nucleotide sequences encoding MK, PMK, MPD, and ID, and a nucleic acid comprising a nucleotide sequence encoding an SPP synthase.

In other embodiments, a subject genetically modified bacterial library comprises at least eight member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; the fifth member bacterium comprising a nucleic acid comprising nucleotide sequences encoding MK, PMK, MPD, and IDI, and a nucleic acid comprising a nucleotide sequence encoding a HepPP synthase the sixth member comprising a nucleic acid comprising nucleotide sequences encoding MK, PMK, MPD, and IDI, and a nucleic acid comprising a nucleotide sequence encoding an OPP synthase; the seventh member bacterium comprising a nucleic acid comprising nucleotide sequences encoding MK, PMK, MPD, and IDI, and a nucleic acid comprising a nucleotide sequence encoding an SPP synthase; and the eighth member bacterium comprising a nucleic acid comprising nucleotide sequences encoding MK, PMK, MPD, and IDI, and a nucleic acid comprising a nucleotide sequence encoding a DPP synthase.

In other embodiments, a subject genetically modified bacterial library comprises at least nine member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; the fifth member bacterium comprising a nucleic acid comprising nucleotide sequences encoding MK, PMK, MPD, and IDI, and a nucleic acid comprising a nucleotide sequence encoding a HepPP synthase the sixth member bacterium comprising a nucleic acid comprising nucleotide sequences encoding MK, PMK, MPD, and IDI, and a nucleic acid comprising a nucleotide sequence encoding an OPP synthase; the seventh member bacterium comprising a nucleic acid comprising nucleotide sequences encoding MK, PMK, MPD, and IDI, and a nucleic acid comprising a nucleotide sequence encoding an SPP synthase; the eighth member bacterium comprising a nucleic acid comprising nucleotide sequences encoding MK, PMK, MPD, and IDI, and a nucleic acid comprising a nucleotide sequence encoding a DPP synthase; and the ninth member bacterium comprising a nucleic acid comprising nucleotide sequences encoding MK, PMK, MPD, and IDI, and a nucleic acid comprising a nucleotide sequence encoding an NPP synthase.

In other embodiments, a subject genetically modified bacterial library comprises at least ten member genetically modified bacteria, the first member bacterium comprising a nucleic acid comprising nucleotide sequences encoding MK, PMK, MPD, and IDI, and a nucleic acid comprising a nucleotide sequence encoding an FPP synthase; the second member bacterium comprising a nucleic acid comprising nucleotide sequences encoding MK, PMK, MPD, and IDI, and a nucleic acid comprising a nucleotide sequence encoding a GPP synthase; the third member bacterium comprising a nucleic acid comprising nucleotide sequences encoding MK, PMK, MPD, and IDI, and a nucleic acid comprising a nucleotide sequence encoding a GGPP synthase; the fourth member bacterium comprising a nucleic acid comprising nucleotide sequences encoding MK, PMK, MPD, and IDI, and a nucleic acid comprising a nucleotide sequence encoding a HexPP synthase; the fifth member bacterium comprising a nucleic acid comprising nucleotide sequences encoding MK, PMK, MPD, and IDI, and a nucleic acid comprising a nucleotide sequence encoding a HepPP synthase the sixth member bacterium comprising a nucleic acid comprising nucleotide sequences encoding MK, PMK, MPD, and IDI, and a nucleic acid comprising a nucleotide sequence encoding an OPP synthase; the seventh member bacterium comprising a nucleic acid comprising nucleotide sequences encoding MK, PMK, MPD, and IDI, and a nucleic acid comprising a nucleotide sequence encoding an SPP synthase; the eighth member bacterium comprising a nucleic acid comprising nucleotide sequences encoding MK, PMK, MPD, and IDI, and a nucleic acid comprising a nucleotide sequence encoding a DPP synthase; the ninth member bacterium comprising a nucleic acid comprising nucleotide sequences encoding MK, PMK, MPD, and IDI, and a nucleic acid comprising a nucleotide sequence encoding an NPP synthase; and the tenth member bacterium comprising a nucleic acid comprising nucleotide sequences encoding MK, PMK, MPD, and IDI, and a nucleic acid comprising a nucleotide sequence encoding a UPP synthase.

In other embodiments, a subject genetically modified bacterial library comprises at least two member genetically modified bacteria, the first member bacterium comprising a first nucleic acid comprising nucleotide sequences encoding acetoacetyl-CoA thiolase, HMGS, and HMGR; a second nucleic acid comprising a nucleotide sequence encoding MK, PMK, MPD, and IDI; and a third nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase; and a second member bacterium comprising a first nucleic acid comprising nucleotide sequences encoding acetoacetyl-CoA thiolase, HMGS, and HMGR; a second nucleic acid comprising a nucleotide sequence encoding MK, PMK, MPD, and IDI; and a third nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase, where the third nucleic acid in the second bacterium comprises a nucleotide sequence encoding a prenyl transferase that is different from the prenyl transferase encoded by the third nucleic acid in the first bacterium.

In other embodiments, a subject genetically modified bacterial library comprises at least two member genetically modified bacteria, the first member bacterium comprising a first nucleic acid comprising nucleotide sequences encoding acetoacetyl-CoA thiolase, HMGS, HMGR, MK, PMK, MPD, and IDI; and a second nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase; and a second member bacterium comprising a first nucleic acid comprising nucleotide sequences encoding acetoacetyl-CoA thiolase, HMGS, HMGR, MK, PMK, MPD, and IDI; and a second nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase, where the second nucleic acid in the second bacterium comprises a nucleotide sequence encoding a prenyl transferase that is different from the prenyl transferase encoded by the second nucleic acid in the first bacterium.

In some embodiments, a subject genetically modified bacterial library comprises at least two member genetically modified bacteria, the first member bacterium comprising a nucleic acid comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase (collectively referred to as "DXP pathway enzymes 1-6"), and optionally also isopentenyl/dimethylallyl diphosphate synthase, and a nucleic acid comprising a nucleotide sequence encoding an FPP synthase; and the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase.

In other embodiments, a subject genetically modified bacterial library comprises at least three member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; and the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase.

In other embodiments, a subject genetically modified bacterial library comprises at least four member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; and the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase.

In other embodiments, a subject genetically modified bacterial library comprises at least five member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6, and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; and the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase.

In other embodiments, a subject genetically modified bacterial library comprises at least six member genetically modified bacteria, the first member bacterium comprising a nucleic acid comprising nucleotide sequences encoding DXP pathway enzymes 1-6, and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase and the sixth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an OPP synthase.

In other embodiments, a subject genetically modified bacterial library comprises at least seven member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an OPP synthase; and the seventh member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an SPP synthase.

In other embodiments, a subject genetically modified bacterial library comprises at least eight member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic-acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an SPP synthase; and the eighth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a DPP synthase.

In other embodiments, a subject genetically modified bacterial library comprises at least nine member genetically modified bacteria, the first member bacterium comprising a nucleic acid comprising nucleotide sequences DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an SPP synthase; the eighth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a DPP synthase; and the ninth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an NPP synthase.

In other embodiments, a subject genetically modified bacterial library comprises at least ten member genetically modified bacteria, the first member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an SPP synthase; the eighth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a DPP synthase; the ninth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding an NPP synthase; and the tenth member bacterium comprising a nucleic acid comprising nucleotide sequences encoding DXP pathway enzymes 1-6 (and optionally also isopentenyl/dimethylallyl diphosphate synthase), and a nucleic acid comprising a nucleotide sequence encoding a UPP synthase.

In other embodiments, a subject genetically modified bacterial library comprises at least two member genetically modified bacteria, the first member bacterium comprising a first nucleic acid comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase (collectively referred to as "DXP pathway enzymes 3-6") and optionally also isopentenyl/dimethylallyl diphosphate synthase; and a second nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase; and a second member bacterium comprising a first nucleic acid comprising nucleotide sequences encoding DXP pathway enzymes 3-6 and optionally also isopentenyl/dimethylallyl diphosphate synthase; and a second nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase, where the second nucleic acid in the second bacterium comprises a nucleotide sequence encoding a prenyl transferase that is different from the prenyl transferase encoded by the second nucleic acid in the first bacterium.

Genetically Modified Eukaryotic Host Cell Libraries

In some embodiments, a subject genetically modified host cell library is a genetically modified eukaryotic host cell library. In some embodiments, the genetically modified eukaryotic host cells are yeast cells (e.g., *Saccharomyces cerevisiae, Pichia*, and the like). The following description exemplifies yeast cells; however, it should be understood that a subject genetically modified eukaryotic host cell library is in no way limited to genetically modified yeast cells.

A subject genetically modified yeast library includes from about 2 member yeast to about 50 member yeast cells, each of which member yeast cells comprises a nucleic acid comprises a nucleotide sequence encoding a different prenyl synthase, e.g., a subject genetically modified yeast library includes from about 2 member yeast to about 4 member yeast cells, from about 4 member yeast cells to about 6 member yeast cells, from about 6 member yeast cells to about 8 member yeast cells, from about 8 member yeast cells to about 10 member yeast, cells from about 10 member yeast cells to about 12 member yeast cells, from about 12 member yeast cells to about 14 member yeast cells from about 14 member yeast cells to about 16 member yeast cells, from about 16 member yeast cells to about 18 member yeast cells, from about 18 member yeast cells to about 20 member yeast cells, or from about 20 member yeast cells to about 50 member yeast cells, or more, each of which member genetically modified yeast cells comprises a nucleic acid comprises a nucleotide sequence encoding a different prenyl synthase from the other member yeast cells. Typically, a plurality of each member genetically modified yeast cell is present in the library, e.g., a subject genetically modified yeast library comprises two or more member yeast cells, where from about 10 to about $10^2$, from about $10^2$ to about $10^4$, from about $10^4$ to about $10^6$, or from about $10^6$ to about $10^8$ or more of each member genetically modified yeast cells is present in the library.

In some embodiments, a subject genetically modified host cell library includes at least two member yeast cells, each of which comprises one or more nucleic acids comprising nucleotide sequences encoding MK, PMK, MPD, and IDI; and a further nucleic acid comprising a nucleotide sequence encoding a different prenyl transferase from other member yeast cells. In other embodiments, a subject genetically modified host cell library includes at least two member yeast cells, each of which comprises one or more nucleic acids comprising a nucleotide sequence encoding acetoacetyl-CoA thiolase, HMGS, and HMGR; one or more nucleic acids comprising a nucleotide sequence encoding N, PMK, MPD, and IDI; and a further nucleic acid comprising a nucleotide sequence encoding a different prenyl transferase from other member yeast cells.

In some embodiments, each of the member genetically modified yeast cells comprises one or more nucleic acids comprising nucleotide sequences encoding MK, PMK, MPD, and IDI, and where at least one of the nucleotide sequences is operably linked to an inducible promoter; and a further nucleic acid comprising a nucleotide sequence encoding a prenyl transferase. In some embodiments, each of the member genetically modified yeast cells comprises one or more nucleic acids comprising nucleotide sequences encoding MK, PMK, MPD, and IDI, where at least one of the nucleotide sequences is operably linked to an inducible promoter; and a further nucleic acid comprising a nucleotide sequence encoding a prenyl transferase.

In some embodiments, each of the member genetically modified yeast cells comprises nucleic acids comprising nucleotide sequences encoding acetoacetyl-CoA thiolase, HMGS, and HMGR, and where at least one of the nucleotide sequences is operably linked to an inducible promoter.

In some embodiments, a subject genetically modified host cell library includes at least two member genetically modified yeast cells, each of which comprises one or more nucleic acids comprising nucleotide sequences encoding DXP pathway enzymes 1-6; and a further nucleic acid comprising a nucleotide sequence encoding a different prenyl transferase from other member genetically modified yeast cells. In other embodiments, a subject genetically modified host cell library includes at least two member genetically modified yeast cells, each of which comprises one or more nucleic acids comprising a nucleotide sequence encoding DXP pathway enzymes 3-6; and a further nucleic acid comprising a nucleotide sequence encoding a different prenyl transferase from other member genetically modified yeast cells. In some embodiments, at least one of the nucleotide sequences encoding one of DXP enzyme pathways 1-6, or DXP enzyme pathways 3-6, is operably linked to an inducible promoter.

For example, a subject genetically modified host cell library comprises two or more member genetically modified yeast cells, each member genetically modified yeast cell a nucleic acid comprising a nucleotide sequence encoding a different prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. Any of the above-described specific examples of a subject genetically modified bacterial library can be modified such that the genetically modified host cells are yeast.

In some embodiments, a subject genetically modified yeast cells library comprises at least two member genetically modified yeast cells, the first member yeast cell comprising one or more nucleic acids comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2C-methyl-D-erythritol kinase, 2C-methyl-D-erythritol 2,4-cyclodiphosphate synthase, and 1-hydroxy-2-methyl-2-(E)-butenyl 4-diphosphate synthase (collectively referred to as "DXP pathway enzymes 1-6"), and optionally also isopentenyl/dimethylallyl diphosphate synthase, and a nucleic acid comprising a nucleotide sequence encoding an FPP synthase; and the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase.

In other embodiments, a subject genetically modified yeast cell library comprises at least three member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; and the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase.

In other embodiments, a subject genetically modified yeast cell library comprises at least four member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GFPP synthase; and the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase.

In other embodiments, a subject genetically modified yeast cell library comprises at least five member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6, and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; and the fifth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HepPP synthase.

In other embodiments, a subject genetically modified yeast cell library comprises at least six member genetically modified yeast cells, the first member yeast cell comprising one or more nucleic acids comprising nucleotide sequences encoding DXP pathway enzymes 1-6, and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HepPP synthase and the sixth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an OPP synthase.

In other embodiments, a subject genetically modified yeast cell library comprises at least seven member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an OPP synthase; and the seventh member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an SPP synthase.

In other embodiments, a subject genetically modified yeast cell library comprises at least eight member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an SPP synthase; and the eighth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a DPP synthase.

In other embodiments, a subject genetically modified yeast cell library comprises at least nine member genetically modified yeast cells, the first member yeast cell comprising one or more nucleic acids comprising nucleotide sequences DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an SPP synthase; the eighth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a DPP synthase; and the ninth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an NPP synthase.

In other embodiments, a subject genetically modified yeast cell library comprises at least ten member genetically modified yeast cells, the first member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an FPP synthase; the second member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GPP synthase; the third member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a GGPP synthase; the fourth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a HexPP synthase; the fifth member yeast cell comprising one or more nucleic comprising nucleotide sequences encoding DXP pathway enzymes 1-6 (and optionally also isopentenyl/dimethylallyl diphosphate synthase), and a nucleic acid comprising a nucleotide sequence encoding a HepPP synthase the sixth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an OPP synthase; the seventh member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an SPP synthase; the eighth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a DPP synthase; the ninth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding an NPP synthase; and the tenth member yeast cell comprising one or more nucleic acids comprising nucleotide sequences encoding DXP pathway enzymes 1-6 (and optionally also isopentenyl/dimethylallyl diphosphate synthase), and a nucleic acid comprising a nucleotide sequence encoding a UPP synthase.

In other embodiments, a subject genetically modified yeast cell library comprises at least two member genetically modified yeast cells, the first member yeast cell comprising one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase (collectively referred to as "DXP pathway enzymes 3-6") and optionally also isopentenyl/dimethylallyl diphosphate synthase; and a further nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase; and a second member yeast cell comprising one or more nucleic acids comprising nucleotide sequences encoding DXP pathway enzymes 3-6 and optionally also isopentenyl/dimethylallyl diphosphate synthase; and a further nucleic acid comprising a nucleotide sequence encoding a prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase, where the further nucleic acid in the second yeast cell comprises a nucleotide sequence encoding a prenyl transferase that is different from the prenyl transferase encoded by the further nucleic acid in the first yeast cell.

Further Genetic Modifications

In some embodiments, the cells in a subject genetically modified host cell library are genetically modified with one or more nucleic acids comprising a nucleotide sequences encoding a terpene biosynthetic pathway enzyme(s), and a nucleic acid comprising a nucleotide sequence encoding a prenyl transferase, and will further comprise one or more genetic modifications that increase the intracellular concentration of a terpene biosynthetic pathway intermediate that is growth inhibiting toward the genetically modified host cell.

In some embodiments, a genetically modified host cell in a subject genetically modified host cell library is a host cell that is genetically modified with one or more nucleic acids encoding a MEV pathway enzyme(s), and that is genetically modified such that one or more endogenous DXP pathway genes is functionally disabled. In some embodiments, a genetically modified host cell in a subject genetically modified host cell library is a prokaryotic host cell that is genetically modified with one or more nucleic acids encoding a MEV pathway enzyme(s), and that is genetically modified such that one or more endogenous DXP pathway genes is functionally disabled. In some of these embodiments, one or more of an endogenous gene encoding 1-deoxy-D-xylulose-5-phosphate synthase, an endogenous gene encoding 1-deoxy-D-xylulose-5-phosphate reductoisomerase, an endogenous gene encoding 4-diphosphocytidyl-2-C-methyl-D-erythritol synthase, an endogenous gene encoding 4-diphosphocytidyl-2-C-methyl-D-erythritol kinase, an endogenous gene encoding 2C-methyl-D-erythritol 2,4-cyclodiphosphate synthase, and an endogenous gene encoding 1-hydroxy-2-methyl-2-(E)-butenyl 4-diphosphate synthase is functionally disabled, e.g., by deleting all or a portion of the gene. For example, in some embodiments, all or a portion of the IspC gene is deleted.

In some embodiments, a genetically modified host cell in a subject genetically modified host cell library is a host cell that is genetically modified with one or more nucleic acids encoding a DXP pathway enzyme(s), and that is genetically modified such that one or more endogenous MEV pathway genes is functionally disabled. In some embodiments, a genetically modified host cell in a subject genetically modified host cell library is a eukaryotic host cell that is genetically modified with a nucleic acid encoding a DXP pathway enzyme, and that is genetically modified such that one or more endogenous MEV pathway genes is functionally disabled. In some of these embodiments, one or more of an endogenous gene encoding acetoacetyl-CoA thiolase, an endogenous gene encoding HMGS, an endogenous gene encoding HMGR, an endogenous gene encoding MK, an endogenous gene encoding PMK, and an endogenous gene encoding MPD is functionally disabled, e.g., by deleting all or a portion of the gene.

In some embodiments, a genetically modified host cell in a subject genetically modified host cell library is a prokaryotic host cell that is genetically modified with one or more nucleic acids encoding a MEV pathway enzyme(s), and that is genetically modified such that intracellular concentration of acetyl CoA is increased. In some of these embodiments, an endogenous pta gene in the prokaryotic host cell is disabled, e.g., by deleting all or part of the pta gene in the host cell.

Compositions Comprising a Subject Genetically Modified Host Cell

The present invention further provides compositions comprising a subject genetically modified host cell library. A subject composition comprises a subject genetically modified host cell library; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Screening Methods

The present invention provides methods of identifying a gene product having activity in a biosynthetic pathway. The methods generally involve: a) producing a test cell by introducing into a genetically modified host cell an exogenous nucleic acid comprising a nucleotide sequence encoding a candidate gene product, wherein the genetically modified host cell produces a biosynthetic pathway intermediate, which intermediate is produced in an amount effective to inhibit growth of the genetically modified host cell; and b) determining the effect, if any, of expression of the candidate gene product on the growth of the test cell. A reduction in growth inhibition indicates that the exogenous nucleic acid encodes a gene product having activity in the biosynthetic pathway.

The biosynthetic pathway intermediate is produced in the genetically modified host cell in an amount that inhibits growth of the test cell, e.g., the intracellular concentration of the intermediate inhibits the growth of the test cell. Typically, the intermediate accumulates in the test cell in an amount that inhibits growth of the test cell by at least about 10%, at least about 20%, at least about 30%, at least about 40%, at least about 50%, at least about 60%, at least about 70%, at least about 80%, or at least about 90%, or more, compared to the growth rate of a control host cell that is not genetically modified, or compared to the growth rate of the test cell that is cultured under conditions that are not conducive to synthesis of growth-inhibiting amounts of the intermediate. In some embodiments, the intermediate accumulates intracellularly in the test cell in an amount that is lethal to the test cell, e.g., induces death of the test cell.

The test cell is cultured in vitro under conditions such that the biosynthetic pathway intermediate accumulates intracellularly in an amount that is growth inhibiting and/or death inducing. In some embodiments, the test cell is cultured in the presence of a substrate for an enzyme in the biosynthetic pathway. In other embodiments, the test cell is cultured in the presence of an inducer that induces expression of a nucleotide sequence encoding a biosynthetic pathway enzyme, where the nucleotide sequence is under control of an inducible promoter.

Whether the intermediate is present in the test cell in an amount that inhibits growth of the test cell can be determined using any standard method for detecting growth inhibition of a cell. For example, growth is frequently measured as an increase in optical density when cells are grown in liquid culture; and growth inhibition can be detected by comparing the optical density (e.g., at 600 nm) of a liquid culture of genetically modified host cells that produce a growth-inhibiting amount of the intermediate, with the optical density of a liquid culture of the same genetically modified host cells that do not produce a growth-inhibiting amount of the intermediate. Growth inhibition can also be detected by visually inspecting the colony size of cells plated on agar containing suitable growth media.

A subject screening method involves introducing an exogenous nucleic acid into a genetically modified host cell, producing a test cell, where the genetically modified host cell is one that exhibits growth inhibition when the biosynthetic pathway intermediate is produced in a growth-inhibiting amount. When an exogenous nucleic acid comprising a nucleotide sequence that encodes an enzyme that modifies the intermediate is introduced into the genetically modified host cell, growth inhibition of the test cell is relieved. Thus, a reduction in growth inhibition indicates that the exogenous nucleic acid encodes a gene product having activity in the biosynthetic pathway. A reduction in growth inhibition includes an at least about 20%, at least about 30%, at least about 40%, at least about 50%, at least about 60%, at least about 70%, at least about 80%, at least about 90%, or more, reduction in growth inhibition. In some embodiments, the gene product having activity in the biosynthetic pathway reduces the growth inhibition such that the rate of cell growth is restored to the rate of cell growth of the genetically modified cell when grown under conditions such that the intermediate is not produced.

In some embodiments, e.g., where the exogenous nucleic acid is a plurality of exogenous nucleic acids (e.g., a cDNA library, a genomic library, a population of nucleic acids, each encoding a terpene synthase with a different amino acid sequence, etc.), the exogenous nucleic acid are introduced into a plurality of genetically modified host cells, forming a plurality of test cells. The test cells are in some embodiments grown in liquid culture under conditions such that the intermediate is accumulated intracellularly in a growth inhibiting and/or death-inducing amount; those test cells comprising an exogenous nucleic acid that comprises nucleotide sequences encoding one or more gene products active in the biosynthetic pathway will grow faster than test cells that do not comprise an exogenous nucleic acid that comprises nucleotide sequences encoding one or more gene products active in the biosynthetic pathway, or those test cells comprising an exogenous nucleic acid that comprises nucleotide sequences encoding one or more gene products active in the biosynthetic pathway will live, while test cells that do not comprise an exogenous nucleic acid that comprises nucleotide sequences encoding one or more gene products active in the biosynthetic pathway will die.

In some embodiments, the intermediate is produced in the test cell in an amount that results in death of the genetically modified host cell. In many of these embodiments, the nucleotide sequence encoding the biosynthetic pathway gene product is under control of an inducible promoter, such that when the promoter is not induced substantially no intermediate is produced, or the intermediate is produced in an amount that does not kill the genetically modified cell. In many embodiments, the biosynthetic pathway gene product is one that consumes a substrate that is added to the culture medium, such that in the absence of the substrate, substantially no intermediate is produced, or the intermediate is produced in an amount that is not growth inhibiting. In some of these embodiments, the methods involve introducing into the genetically modified host cell a nucleic acid-comprising a nucleotide sequence that encodes an enzyme that modifies the intermediate; inducing expression of the nucleic acid comprising a nucleotide sequence that encodes an enzyme that modifies the intermediate, e.g., by adding inducer to the culture medium; and determining the effect, if any, of the nucleic acid on cell death. In these embodiments, a genetically modified host cell that is grown in in vitro culture in the presence of the biosynthetic pathway substrate, but into which an exogenous nucleic acid has not been introduced, serves as a control cell that dies upon intracellular accumulation of the biosynthetic pathway intermediate. In many embodiments, determining the effect of the exogenous nucleic acid on cell death involves identifying genetically modified host cells that are not killed by the intermediate, e.g., identifying survivors. Identification of survivors is readily achieved by allowing survivors to multiply.

For example, where the genetically modified host cell is a bacterium, survivors are identified by plating the cells on agar containing bacterial culture medium, where the survivors form colonies, and the dead cells do not. Where the genetically modified host cell is a eukaryotic cell such as a yeast cell, survivors are identified by plating the cells on agar containing yeast culture medium, where the survivors form colonies, and the dead cells do not. Where the genetically modified host cell is a eukaryotic cell such as a mammalian cell grown as unicellular entities, survivors are identified by culturing the cells in suitable culture medium, and allowing survivors to multiply. Where the genetically modified host cell is a eukaryotic cell such as a mammalian cell grown as unicellular entities, survivors can also be identified using fluorescence-activated cell sorting, e.g., using any of a number of methods to discriminate between live and dead cells, e.g., using propidium iodide to stain dead cells.

In some embodiments, live test cells are separated from dead test cells by buoyant density separation, using well-established methods. In some embodiments, test cells are separated into two groups, the first group including metabolically inactive cells (e.g., dead cells), and mitotically inactive cells; and the second group including mitotically active cells (e.g., live cells), and metabolically active cells. See, e.g. Glaser et al. (1989) *J. Bacteriol.* 171:4992. Test cells that exhibit a reduction in biosynthetic pathway intermediate-induced growth inhibition are expected to be mitotically active and/or metabolically active. Test cells that exhibit growth inhibition, e.g., are not rescued from growth inhibition by a gene product encoded by an exogenous nucleic acid, are expected to be mitotically inactive and/or metabolically inactive.

In some embodiments, a subject screening method for identifying a gene product having activity in a biosynthetic pathway involves a) introducing into a plurality of genetically modified host cells (e.g., genetically modified host cells in in vitro culture) an exogenous nucleic acid encoding a candidate gene product, forming test cells, where the genetically modified host cells are genetically modified with a nucleic acid comprising a nucleotide sequence encoding a biosynthetic pathway enzyme, and where synthesis of the enzyme in the test cells results in conversion of a substrate for the enzyme into a biosynthetic pathway intermediate, which intermediate is produced in an amount effective to inhibit growth of the test cell; and b) determining the effect, if any, of expression of the candidate gene product on the growth of the test cells, where a reduction in growth inhibition indicates that the exogenous nucleic acid encodes a gene product having activity in the biosynthetic pathway.

In some embodiments, a subject screening method for identifying a gene product having activity in a biosynthetic pathway involves a) introducing into a plurality of genetically modified host cells in in vitro culture a plurality of exogenous nucleic acids, each encoding a candidate gene product, forming test cells, where the genetically modified host cells are genetically modified with a nucleic acid comprising a nucleotide sequence encoding a biosynthetic pathway enzyme, and where synthesis of the enzyme in the test cells results in conversion of a substrate for the enzyme into a biosynthetic pathway intermediate, which intermediate is produced in an amount effective to inhibit growth of the test cell; and b) determining the effect, if any, of expression of the candidate gene product on the growth of the test cells, where a reduction in growth inhibition identifies an exogenous nucleic acid that encodes a gene product having activity in the biosynthetic pathway.

In some embodiments, a subject method of identifying a gene product having activity in a biosynthetic pathway involves: a) introducing into a plurality of genetically modified host cells in in vitro culture a plurality of exogenous nucleic acids, each comprising a nucleotide sequence encoding a candidate gene product, forming test cells, where the genetically modified host cells are genetically modified with a nucleic acid comprising a nucleotide sequence encoding a biosynthetic pathway enzyme, and where synthesis of the enzyme in the test cells results in conversion of a substrate for the enzyme into a biosynthetic pathway intermediate, which intermediate is produced in an amount effective to induce death of the test cells; and b) upon detecting cell death in control cells into which an exogenous nucleic acid has not been introduced, detecting test cells that survive the intermediate-induced cell death, where survival of a test cell identifies an exogenous nucleic acid that encodes a gene product having activity in the biosynthetic pathway. Thus, a test cell that survives the intermediate-induced cell death comprises a candidate gene product having activity in the biosynthetic pathway.

In some embodiments, the biosynthetic pathway enzyme substrate is added to the in vitro culture medium. In other embodiments, the genetically modified cell produces the biosynthetic pathway enzyme substrate.

In some embodiments, the genetically modified host cells are genetically modified by introducing into a host cell a nucleic acid comprising a nucleotide sequence encoding a biosynthetic pathway enzyme, where synthesis of the biosynthetic pathway enzyme in the genetically modified host cell results in conversion of a substrate for the enzyme into a biosynthetic pathway intermediate that is produced in the cell and/or accumulates in the cell in an amount that is effective to inhibit growth of the cell. In some embodiments, the nucleotide sequence encoding the biosynthetic pathway enzyme is under control of an inducible promoter that is responsive to an inducing agent. In these embodiments, an inducing agent is added to the culture medium, the biosynthetic pathway enzyme is synthesized following addition of the inducing agent, and the biosynthetic pathway intermediate is produced in the cell and/or accumulates in the cell in an amount that is effective to inhibit growth of the cell. In some embodiments, both an inducing agent and a substrate for the biosynthetic pathway enzyme are added to the culture medium.

In other embodiments, the genetically modified cell is genetically modified by mutating one or more genes that affect synthesis of the biosynthetic pathway intermediate in the cell, such that the biosynthetic pathway intermediate is produced in the cell and/or accumulates in the cell in an amount that is effective to inhibit growth of the cell.

Methods of Identifying an Agent that Inhibits a Metabolic Pathway

In some embodiments, the present invention provides methods of identifying an agent that inhibits a metabolic pathway in a genetically modified host cell in which a metabolic pathway intermediate is produced in the cell and/or accumulates in the cell in an amount that is effective to inhibit growth of the cell. Thus, in some embodiments, the present invention provides a method of identifying an agent that inhibits a metabolic pathway in a cell, the method generally involving: a) contacting a test cell with a test agent, wherein the test cell produces a metabolic pathway intermediate, which intermediate is produced in an amount effective to inhibit growth of the test cell; and b) determining the effect, if any, of the agent on growth of the test cell. A reduction in growth inhibition indicates the agent inhibits the metabolic pathway. In some embodiments, the metabolic pathway is a biosynthetic pathway. In other embodiments, the metabolic pathway is an anabolic pathway.

The terms "candidate agent," "test agent," "agent," "substance," and "compound" are used interchangeably herein. Candidate agents encompass numerous chemical classes, in some embodiments synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents are in some embodiments small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In some embodiments, the test agent is an exogenous nucleic acid that is introduced into the test cell. In these embodiments, the method generally involves producing a test cell by introducing into a genetically modified host cell an exogenous nucleic acid comprising a nucleotide sequence encoding a candidate gene product, wherein the genetically modified host cell produces a metabolic pathway intermediate, which intermediate is produced in an amount effective to inhibit growth of the genetically modified host cell; and determining the effect, if any, of expression of the candidate gene product on growth of the test cell, wherein a reduction in growth inhibition indicates the candidate gene product inhibits a metabolic pathway involving the metabolic pathway intermediate. Non-limiting examples of gene products that would inhibit a metabolic pathway, and therefore relieve the metabolic pathway-mediated growth inhibition, include, but are not limited to, a protein that inhibits an enzyme in the metabolic pathway that produces the growth-inhibiting intermediate; a protein that proteolytically degrades one or more enzymes in the metabolic pathway hat produces the growth-inhibiting intermediate; a protein that consumes (e.g., modifies) a non-toxic precursor to the growth-inhibiting intermediate; a transcriptional control element that down-regulates the metabolic pathway that produces the growth-inhibiting intermediate, at the level of transcription and/or translation; a protein that modifies the growth-inhibiting intermediate; and the like.

Agents identified using the above-described method for identifying agents that inhibit a metabolic pathway are useful for inhibiting a variety of metabolic pathways, including, e.g., a cholesterol biosynthetic pathway, an insect pheromone biosynthetic pathway, and the like.

Isolating Exogenous Nucleic Acid from a Test Cell

In some embodiments, the method further involves isolating an exogenous nucleic acid from a test cell, where the exogenous nucleic acid is one that that relieves growth inhibition in a subject screening method. Methods of isolating the exogenous nucleic acid from a test cell are well known in the art. Suitable methods include, but are not limited to, any of a number of alkaline lysis methods that are standard in the art.

In some embodiments, live test cells are separated from dead test cells by density gradient centrifugation, where the live and/or mitotically active test cells have a different buoyant density from the buoyant density of dead and/or mitotically inactive test cells. Exogenous nucleic acids are then isolated from the live or mitotically active test cells.

Further Characterization of a Candidate Gene Product

In some embodiments, a subject screening method will further comprise further characterizing a candidate gene product. In these embodiments, the exogenous nucleic acid comprising nucleotide sequence(s) encoding one or more candidate gene products having activity in a metabolic pathway (e.g., a biosynthetic pathway, or an anabolic pathway) are isolated from a test cell; the gene product(s) are expressed in a cell and/or in an in vitro cell-free transcription/translation system. In some embodiments, the exogenous nucleic acid is subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists. In addition, the gene product(s) are expressed in a cell and/or in an in vitro cell-free transcription/translation system; and the effect of the gene product(s) on a metabolic pathway intermediate or other metabolite is analyzed.

For example, as discussed in more detail below, in some embodiments, a subject screening method identifies candidate gene products having activity in a terpene metabolic pathway, e.g., a terpene biosynthetic pathway. Whether a gene product is active in a terpene biosynthetic pathway is readily determined using any known method. For example, where a terpene biosynthetic pathway gene product is a terpene synthase, a nucleic acid comprising a nucleotide sequence encoding the candidate gene product is introduced into a genetically modified host cell, and the genetically modified host cell comprising the exogenous nucleic acid is cultured under conditions such that the genetically modified host cell produces an intermediate that is a substrate for the candidate gene product, and a the candidate gene product catalyzes the modification of the intermediate, to form a product. If the candidate gene product is a terpene synthase, the product will be a terpenoid compound. Methods of identifying a terpenoid compound are well known in the art, and include gas chromatography-mass spectrometry (GC-MS) analysis of the product. By comparing retention times and mass spectra of the putative terpenoid compound with retention times and mass spectra of known terpenoid compounds, an identification of the putative terpenoid compound can be made.

Exogenous Nucleic Acids

Exogenous nucleic acids that are suitable for introducing into a genetically modified host cell include, but are not limited to, naturally-occurring nucleic acids isolated from a cell; naturally-occurring nucleic acids that have been modified (e.g., by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like.

Exogenous nucleic acids that are suitable for introducing into a genetically modified host cell include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis.

In some embodiments, exogenous nucleic acids are a cDNA library made from cells, either prokaryotic cells or eukaryotic cells. In some embodiments, exogenous nucleic acids are a genomic DNA library made from cells, either prokaryotic cells or eukaryotic cells. In some embodiments, an exogenous nucleic acid will comprise nucleotide sequences encoding two or more gene products that have activity in a biosynthetic pathway.

In other embodiments, exogenous nucleic acids are a library of nucleic acids, each comprising a nucleotide sequence encoding a biosynthetic pathway enzyme comprising an amino acid sequence that differs from an amino acid sequence of a known biosynthetic pathway enzyme by from about 1 amino acid to about 50 amino acids, e.g., from about 1 amino acid to about 5 amino acids, from about 5 to about 10 amino acids, from about 10 amino acids to about 15 amino acids, from about 15 amino acids to about 20 amino acids, from about 20 amino acids to about 30 amino acids, from about 30 amino acids to about 40 amino acids, or from about 40 amino acids to about 50 amino-acids. In other embodiments, exogenous nucleic acids are a library of nucleic acids, each comprising a nucleotide sequence encoding a terpene synthase comprising an amino acid sequence that differs from an amino acid sequence of a known terpene synthase by from about 1 amino acid to about 50 amino acids, e.g., from about 1 amino acid to about 5 amino acids, from about 5 to about 10 amino acids, from about 10 amino acids to about 15 amino acids, from about 15 amino acids to about 20 amino acids, from about 20 amino acids to about 30 amino acids, from about 30 amino acids to about 40 amino acids, or from about 40 amino acids to about 50 amino acids.

Nucleic acids will in some embodiments be mutated before being introduced into a host cell. Methods of mutating a nucleic acid are well know in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (e.g., diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable methods for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/0,000 genes) in the genome of the cell. Examples of genes encoding DNA repair enzymes include but are not limited to Mut H, Mut S, Mut L, and Mut U, and the homologs thereof in other species (e.g., MSH 1-6, PMS 1-2, MLH 1, GTBP, ERCC-1, and the like). Methods of mutating nucleic acids are well known in the art, and any known method is suitable for use. See, e.g., Stemple (2004) *Nature* 5:1-6; Chiang et al. (1993) *PCR Methods Appl* 2(3): 210-217; Stemmer (1994) *Proc. Natl. Acad. Sci. USA* 91:10747-51; and U.S. Pat. Nos. 6,033,861, and 6,773,900.

In many embodiments, the exogenous nucleic acid is inserted into an expression vector. Expression vectors that are suitable for use in prokaryotic and eukaryotic host cells are known in the art and any suitable expression vector can be used. Suitable expression vectors are as described above.

Nucleic Acid Sources

As noted above, an exogenous nucleic acid will in some embodiments be isolated from a cell or an organism in its natural environment. In some embodiments, the nucleic acid of the cell or organism will be mutated before nucleic acid is isolated from the cell or organism. In other embodiments, the exogenous nucleic acid is synthesized in a cell-free system in vitro.

Exogenous nucleic acids that are suitable for introducing into a genetically modified host cell include nucleic acids isolated from cells or organism of a different species from the genetically modified host cell. Suitable sources of exogenous nucleic acids include, but are not limited to, a cell or organism of any of the six kingdoms, e.g., Bacteria (e.g., Eubacteria); Archaebacteria; Protista; Fungi; Plantae; and Animalia. Suitable sources of exogenous nucleic acids include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., *Euglena*), amoeboids (e.g., amoeba), sporozoans (e.g, Apicomplexa, Myxozoa, Microsporidia), and ciliates (e.g., *Paramecium*). Suitable sources of exogenous nucleic acids include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sources of exogenous nucleic acids include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of exogenous nucleic acids include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Plaiyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., suitable cells include cells from organisms that include, but are not limited to, a protozoan, a plant, a fungus, an algae, a yeast, a reptile, an amphibian, a mammal, a marine microorganism, a marine invertebrate, an arthropod, an isopod, an insect, an arachnid, an archaebacterium, and a eubacterium.

Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota. Suitable eubacteria include, but are not limited to, any member of Hydrogenobacteria, Thermotogales, Green nonsulfphur bacteria, Denococcus Group, Cyanobacteria, Purple bacteria, *Planctomyces*, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

In some embodiments, nucleic acid will be isolated from a tissue taken from an organism; from a particular cell or group of cells isolated from an organism; etc. For example, where the organism is a plant, the nucleic acid will in some embodiments be isolated from the xylem, the phloem, the cambium layer, leaves, roots, etc. Where the organism is an animal, the nucleic acid will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

Cells, either unicellular organisms or cells isolated from a multicellular organism, and multicellular organisms, will in some embodiments be exposed to one or more internal or external signals before nucleic acid (e.g., mRNA) is isolated from the cell or the organism. External and internal signals that affect gene expression include, but are not limited to, infection of a cell by a microorganism, including, but not limited to, a bacterium (e.g., *Mycobacterium* spp., *Shigella, Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); infection of a plant with an insect (e.g., a spider mite, an aphid, a tobacco worm, etc.); withholding of water (e.g., withholding water from a plant); stress; infection of a plant with an arachnid; a wound (e.g., wounding a plant leaf, stem, or root); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; light; dark; mitogens, including, but not limited to, lipopolysaccharide (LPS), pokeweed mitogen; antigens; sleep pattern; electrical charge; ion concentration of the medium in which a cell is maintained or an internal ion concentration, exemplary ions including sodium ions, potassium ions, chloride ions, calcium ions, and the like; presence or absence of a nutrient; metal ions; a transcription factor; a tumor suppressor; cell-cell contact; and the like.

Methods of isolating nucleic acids from a cell or an organism are well known in the art. In some embodiments, genomic DNA will be isolated from the cell or the organism. In other embodiments, RNA will be isolated from the cell or the organism; and a cDNA copy of the RNA (e.g., mRNA) will be synthesized in vitro.

In many embodiments, a cDNA library of mRNA isolated from a cell or an organism will be used as the source of exogenous nucleic acid. In some embodiments, the cDNA library will be constructed using an expression vector that is configured such that the inserted cDNA will include a tag, where the tag is one that provides for ease of isolating a candidate gene product.

Synthetic Nucleic Acids

In some embodiments, nucleic acids that are introduced into a genetically modified host cell synthetic nucleic acids, including recombinant nucleic acids, nucleic acids synthesized in a cell-free system in vitro, and the like. Methods of synthesizing nucleic acids are well known in the art. In some embodiments, the synthetic nucleic acid will comprise a nucleotide sequence that encodes a variant of a known biosynthetic pathway gene product. In some of these embodiments, the exogenous nucleic acid will be mutated, using any of the above-described methods.

In some embodiments, the synthetic nucleic acid comprises a nucleotide sequence encoding a terpene synthase that differs in amino acid sequence by one or more amino acids from a naturally-occurring terpene synthase or other parent terpene synthase, e.g., a variant terpene synthase. A "parent terpene synthase" is a terpene synthase that serves as a reference point for comparison. Variant terpene synthases include consensus terpene synthases and hybrid terpene synthases. In some embodiments, the synthetic nucleic acid comprises a nucleotide sequence encoding a consensus terpene synthase. In other embodiments, the synthetic nucleic acid comprises a nucleotide sequence encoding a hybrid terpene synthase.

Variant Terpene Synthases

In some embodiments, a synthetic nucleic acid comprises a nucleotide sequence encoding a variant terpene synthase, e.g., a terpene synthase that differs in amino acid sequence by one or more amino acids from a naturally-occurring terpene synthase or other parent terpene synthase. In some embodiments, a variant terpene synthase differs in amino acid sequence by one amino acid, two amino acids, three amino acids, four amino acids, five amino acids, six amino acids, seven amino acids, eight amino acids, nine amino acids, or amino acids, or more, compared to the amino acid sequence of a naturally-occurring parent terpene synthase. In some embodiments, a variant terpene synthase differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30-amino acids to about 35 amino acids, from about 35 amino acids to about 40 amino acids, from about 40 amino acids to about 50 amino acids, or from about 50 amino acids to about 60 amino acids, or more, compared to the amino acid sequence of a naturally-occurring parent terpene synthase.

In some embodiments, a nucleic acid comprising a nucleotide sequence encoding a naturally-occurring terpene synthase is mutated, using any of a variety of well-established methods, giving rise to a nucleic acid comprising a nucleotide sequence encoding a variant terpene synthase. Suitable mutagenesis methods include, but are not limited to, chemical mutation methods, radiation-induced mutagenesis, and methods of mutating a nucleic acid during synthesis, as described supra. Thus, e.g., a nucleic acid comprising a nucleotide sequence encoding a naturally-occurring terpene synthase is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant terpene synthase. See, e.g., Greener et al., "An Efficient Random Mutagenesis Technique Using an *E. coli* Mutator Strain", *Methods in Molecular Biology*, 57:375-385 (1995). Saturation mutagenesis techniques employing a polymerase chain reaction (PCR) are also well known and can be used. See, e.g., U.S. Pat. No. 6,171,820. Nucleic acids comprising a nucleotide sequence encoding a variant terpene synthase are identified by the ability to relieve growth inhibition by a terpene biosynthetic pathway intermediate.

Nucleotide sequences encoding terpene synthases are known in the art, and any known terpene synthase-encoding nucleotide sequence can be altered to generate a synthetic nucleic acid for use in a subject method. For example, the following terpene synthase-encoding nucleotide sequences, followed by their GenBank accession numbers and the organisms in which they were identified, are known and can be modified: (−)-germacrene D synthase mRNA (AY438099; *Populus balsamifera* subsp. *trichocarpa* x *Populus deltoids*); E,E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; *Zea mays*); terpene synthase 4 (TPS4) mRNA (AY518312; *Zea mays*); myrcene/ocimene synthase (TPS10) (At2g24210) mRNA (NM_127982; *Arabidopsis thaliana*); geraniol synthase (GES) mRNA (AY362553; *Ocimum basilicum*); pinene synthase mRNA (AY237645; *Picea sitchensis*); myrcene synthase 1e20 mRNA (AY195609; *Antirrhinum majus*); (E)-β-ocimene synthase (0e23) mRNA (AY195607; *Antirrhinum majus*); E-β-ocimene synthase mRNA (AY151086; *Antirrhinum majus*); terpene synthase mRNA (AF497492; *Arabidopsis thaliana*); (−)-camphene synthase (AG6.5) mRNA (U87910; *Abies grandis*); (−)-4S-limonene synthase gene (e.g., genomic sequence) (AF326518; *Abies grandis*); delta-selinene synthase gene (AF326513; *Abies grandis*); amorpha-4,11-diene synthase mRNA (AJ251751; *Artemisia* annua); E-α-bisabolene synthase mRNA (AF006195; *Abies grandis*); gamma-humulene synthase mRNA (U92267; *Abies grandis*); δ-selinene synthase mRNA (U92266; *Abies grandis*); pinene synthase (AG3.18) mRNA (U87909; *Abies grandis*); myrcene synthase (AG2.2) mRNA (U87908; *Abies grandis*); etc.

In some embodiments, a synthetic nucleic acid comprising a nucleotide sequence encoding a variant terpene synthase is one that hybridizes under suitable hybridization conditions to a nucleic acid comprising a nucleotide sequence encoding any known terpene synthase. In some embodiments, a synthetic nucleic acid comprising a nucleotide sequence encoding a variant terpene synthase is one that hybridizes under suitable hybridization conditions to a nucleic acid comprising a nucleotide sequence encoding a naturally-occurring terpene synthase. In some embodiments, a synthetic nucleic acid comprising a nucleotide sequence encoding a variant terpene synthase comprises a variant terpene synthase-encoding nucleotide sequence that has less than about 95% nucleotide sequence identity to a known terpene synthase-encoding nucleotide sequence, e.g., the variant terpene synthase-encoding nucleotide sequence has no more than from about 90% to about 95%, from about 85% to about 90%, from about 80% to about 85%, from about 75% to about 80%, from about 70% to about 75%, from about 65% to about 70%, from about 60% to about 65%, from about 55% to about 60%, or from about 50% to about 55% nucleotide sequence identity to a known terpene synthase-encoding nucleotide sequence.

In some embodiments, the nucleotide sequence encoding a variant terpene synthase encodes a terpene synthase that has from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% amino acid sequence identity to the amino acid sequence of a known terpene synthase. Amino acid sequences of a number of terpene synthases are known in the art.

For example, amino acid sequences of the following terpene synthases are found under the GenBank Accession numbers shown in parentheses, along with the organism in which each was identified, following each terpene synthase: (−)-germacrene D synthase (AAR99061; *Populus balsamifera* subsp. *trichocarpa* x *Populus deltoids*); D-cadinene synthase (P93665; *Gossypium hirsutum*); 5-epi-aristolochene synthase (Q40577; *Nicotiana tabacum*); E,E-alpha-farnesene synthase (AAU05951; *Cucumis sativus*); 1,8-cineole synthase (AAU01970; *Arabidopsis thaliana*); (R)-limonene synthase 1 (Q8L5K3; *Citrus limon*); syn-copalyl diphosphate synthase (AAS98158; *Oryza sativa*); a taxadiene synthase (Q9FT37; *Taxus chinensis*; Q93YA3; *Taxus bacca*; Q41594; *Taxus brevifolia*); a D-cadinene synthase (Q43714; *Gossypium arboretum*); terpene synthase 5 (AAS88575; *Zea mays*); terpene synthase 4 (AAS88573; *Zea mays*); terpenoid synthase (AAS79352; *Vitis vinifera*); geraniol synthase (AAR11765; *Ocimum basilicum*); myrcene synthase 1e20 (AAO41727; *Antirrhinum majus*); 5-epi-aristolochene synthase 37 (AAP05762; *Nicotiana attenuata*); (+)-3-carene synthase (AAO73863; *Picea abies*); (−)-camphene synthase (AAB70707; *Abies grandis*); abietadiene synthase (AAK83563; *Abies grandis*); amorpha-4,11-diene synthase (CAB94691; *Artemisia annua*); trichodiene synthase (AAC49957; *Myrothecium roridum*); gamma-humulene synthase (AAC05728; *Abies grandis*); δ-selinene synthase (AAC05727; *Abies grandis*); etc.

Consensus Terpene Synthases

In some embodiments, a synthetic nucleic acid comprises a nucleotide sequence encoding a terpene synthase comprising a consensus amino acid sequence. A consensus amino acid sequence is derived by aligning three or more amino acid sequences, and identifying amino acids that are shared by at least two of the sequences. In some embodiments, the encoded terpene synthase comprises a consensus sequence derived from determining a consensus sequence of two or more naturally occurring plant terpene synthases. In some embodiments, the encoded terpene synthase comprises a consensus sequence derived from determining a consensus sequence of two or more naturally occurring animal terpene synthases. In some embodiments, the encoded terpene synthase comprises a consensus sequence derived from determining a consensus sequence of two or more naturally occurring bacterial terpene synthases. In some embodiments, the encoded terpene synthase comprises a consensus sequence derived from determining a consensus sequence of two or more naturally occurring terpene synthases from two or more different kingdoms, phyla, classes, order, families, genuses, or species. As one non-limiting example, a consensus terpene synthase amino acid sequence is derived by comparing (−)-limonene synthases from two, three, four, or more different plant species. As another non-limiting example, a consensus terpene synthase amino acid sequence is derived by comparing (E)-α-bisabolene synthase, myrcene synthase, δ-selinene synthase, and abietadiene synthase amino acid sequences (see, e.g., Bohlmann et al. (1998) *Proc. Natl. Acad. Sci. USA* 95:4126-2133).

Hybrid Terpene Synthases

In some embodiments, a synthetic nucleic acid comprises a nucleotide sequence encoding a hybrid terpene synthase. Hybrid terpene synthases comprise amino acid sequences from two or more different terpene synthases.

In some embodiments, the hybrid terpene synthase comprises, in order from N-terminus to C-terminus, from about 2 to about 90, e.g., from about 2 to about 5, from about 5 to about 7, from about 7 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 75 to about 80, from about 80 to about 85, or from about 85 to about 90 contiguous amino acids of a first terpene synthase; and from about 2 to about 90, e.g., from about 2 to about 5, from about 5 to about 7, from about 7 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 75 to about 80, from about 80 to about 85, or from about 85 to about 90 contiguous amino acids of a second terpene synthase, where the first and second terpene synthases are different.

In some embodiments, the hybrid terpene synthase further comprises from about 2 to about 90, e.g., from about 2 to about 5, from about 5 to about 7, from about 7 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 75 to about 80, from about 80 to about 85, or from about 85 to about 90 contiguous amino acids of a third terpene synthase, where the third terpene synthase is different from the first and second terpene synthases.

In still other embodiments, a hybrid terpene synthase further comprises from about 2 to about 90, e.g., from about 2 to about 5, from about 5 to about 7, from about 7 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 75 to about 80, from about 80 to about 85, or from about 85 to about 90 contiguous amino acids of a fourth terpene synthase, where the fourth terpene synthase is different from the first, second, and third terpene synthases.

As one non-limiting example, a hybrid terpene synthase comprises amino acid sequences from two or more members of the Tspa gene family; two or more members of the Tspb gene family; two or more members of the Tspc gene family; two or more members of the Tspd gene family; two or more members of the Tspe gene family; two or more members of the Tspf gene family; or two or more members of the Tspg gene family. See, e.g., Bohmann et al. (1998), supra; and Dudareva et al. (2003) *The Plant Cell* 15:1277-1241.

Hybrid terpene synthases can be generated using any known method, including, but not limited to, exon shuffling, domain swapping, and the like. Exon shuffling methods are well known in the art. See, e.g., Nixon et al. (1997) *Proc. Natl. Acad. Sci. USA* 94:1069-1073; Fisch et al. (1996) *Proc Natl Acad Sci USA* 93(15):7761-7766. Methods of generating nucleic acids encoding hybrid terpene synthases are well known in the art; and any known method can be used. See, e.g., Meyerhans et al. "DNA recombination using PCR" *Nucleic Acids Res.* 18:1687-1691 (1990); Klug et al. (1991) "Creating chimeric molecules by PCR directed homologous DNA recombination." *Nucl. Acids Res.* 19(10): 2793; Ho et al. "Site-directed mutagenesis by overlap extension using the polymerase chain reaction" *Gene* 77:51-59 (1989); Calogero et al. "In vivo recombination and the production of hybrid genes" *Microbiol. Lett.* 97:41-44 (1992); and U.S. Pat. Nos. 6,653,072, 6,177,263.

As one non-limiting example, exons encoding the Tspd-type terpene synthases γ-humulene and δ-selinine can be shuffled to generate a hybrid terpene synthase, e.g., where a synthetic nucleic acid is generated that comprises exons IX, X, and XI of a γ-humulene gene and exons XII, XIII, and XIV of a δ-selinine gene. The exon/introns structures of numerous terpene synthase genes are known and have been published. See, e.g., Trapp and Croteau (2001) *Genetics* 168:811-832; and Cseke et al. (1998) *Mol Biol Evol.* 15(11):1491-8.

Hybrid terpene synthases can be generated by a domain swapping method. Functional domains of terpene synthases are known in the art. See, e.g., Back and Chappell ((1996) *Proc. Natl. Acad. Sci. USA* 93:6841-6845). For example, exon 4 of the 5-epi-aristolochene synthase gene of *Nicotiana tabacum* encodes an amino acid sequence conferring product specificity for the predominant reaction products of the tobacco terpene synthase; while exon 6 of the vetispiradiene synthase gene of *Hyoscyamus muticus* encodes an amino acid sequence conferring product specificity for the predominant reaction products of the *Hyoscyamus* terpene synthase.

Biosynthesis Pathway Gene Products

Biosynthetic pathway gene products that can be identified using a subject method include gene products that have activity in a biosynthetic pathway that produces an intermediate that is growth inhibiting (e.g.; toxic) for a prokaryotic or eukaryotic host cell that produces the intermediate.

As one non-limiting example, *E. coli* expressing the *S. cerevisiae* HMG-CoA synthase accumulate HMG-CoA at levels that are growth inhibiting. An exogenous nucleic acid comprising a nucleotide sequence encoding HMG-CoA reductase relieves the growth inhibition caused by accumulation of HMG-CoA.

As another non-limiting example, a prokaryotic host cell is genetically modified with a nucleic acid comprising nucleotide sequences that encode gene products in a biosynthetic pathway, where the biosynthetic pathway produces an antibiotic (the toxic, or growth-inhibiting, intermediate). Exogenous nucleic acids are introduced into the genetically modified host cell; and nucleic acids comprising nucleotide sequences encoding gene products that provide for antibiotic resistance are identified by their ability to relieve the growth inhibition caused by the antibiotic. In this example, gene products include proteins that provide for export of the antibiotic from the cell; and enzymes that modify the antibiotic such that it no longer inhibits growth of the cell.

Terpene Biosynthetic Pathways

The present invention provides screening methods, for identifying a gene product having activity in a terpene biosynthetic pathway. The methods generally involve a) introducing into a genetically modified host cell an exogenous nucleic acid comprising a nucleotide sequence encoding a candidate gene product, where the genetically modified host cell is genetically modified with a nucleic acid comprising a nucleotide sequence encoding one or more terpene biosynthetic pathway enzymes, where synthesis of the enzyme(s) in the host cell results in conversion of a substrate for the enzyme into a biosynthetic pathway intermediate, which intermediate is produced in an amount effective to inhibit growth of the host cell; and b) determining the effect, if any, of expression of the candidate gene product on the growth of the host cell. A reduction in growth inhibition indicates that the exogenous nucleic acid encodes a gene product having activity in the terpene biosynthetic pathway.

Terpene biosynthetic pathway intermediates that inhibit growth of a host cell include, but are not limited to, IPP, DMAPP, and polyprenyl diphosphates (e.g., GPP, FPP, GGPP, GFPP, HexPP, HepPP, OPP, SPP, DPP, NPP, UPP, etc.).

In some embodiments, a subject screening method for identifying a gene product having activity in a terpene biosynthetic pathway involves a) introducing into a plurality of genetically modified host cells in in vitro culture an exogenous nucleic acid encoding a candidate gene product, forming test cells, where the genetically modified host cells are genetically modified with a nucleic acid comprising a nucleotide sequence encoding a terpene biosynthetic pathway enzyme, and where synthesis of the enzyme in the test cells results in conversion of a substrate for the enzyme into a terpene biosynthetic pathway intermediate, which intermediate is produced in an amount effective to inhibit growth of the test cell; and b) determining the effect, if any, of expression of the candidate gene product on the growth of the test cells, where a reduction in growth inhibition indicates that the exogenous nucleic acid encodes a gene product having activity in the terpene biosynthetic pathway.

In some embodiments, a subject screening method for identifying a gene product having activity in a terpene biosynthetic pathway involves a) introducing into a plurality of genetically modified host cells in in vitro culture a plurality of exogenous nucleic acids, each exogenous nucleic acid comprising a nucleotide sequence encoding a candidate gene product, forming test cells, where the genetically modified host cells are genetically modified with a nucleic acid comprising a nucleotide sequence encoding a terpene biosynthetic pathway enzyme, and where synthesis of the enzyme in the test cells results in conversion of a substrate for the enzyme into a terpene biosynthetic pathway intermediate, which intermediate is produced in an amount effective to inhibit growth of the test cell; and b) determining the effect, if any, of expression of the candidate gene product on the growth of the test cells, where a reduction in growth inhibition identifies an exogenous nucleic acid that encodes a gene product having activity in the terpene biosynthetic pathway.

In some embodiments, a subject method of identifying a gene product having activity in a terpene biosynthetic pathway involves: a) introducing into a plurality of genetically modified host cells in in vitro culture a plurality of exogenous nucleic acids, each comprising a nucleotide sequence encoding a candidate gene product, forming test cells, where the genetically modified host cells are genetically modified with a nucleic acid comprising a nucleotide sequence encoding a terpene biosynthetic pathway enzyme, and where synthesis of the enzyme in the test cells results in conversion of a substrate for the enzyme into a terpene biosynthetic pathway intermediate, which intermediate is produced in an amount effective to induce death of the test cells; and b) upon detecting cell death in control cells into which an exogenous nucleic acid has not been introduced, detecting test cells that survive the intermediate-induced cell death, where survival of a test cell identifies an exogenous nucleic acid that encodes a gene product having activity in the terpene biosynthetic pathway. Thus, a test cell that survives the intermediate-induced cell death comprises a candidate gene product having activity in the terpene biosynthetic pathway.

In some embodiments, the biosynthetic pathway enzyme substrate is added to the in vitro culture medium. In some embodiments, the genetically modified host cells are genetically modified with a nucleic acid comprising a nucleotide sequence encoding a biosynthetic pathway enzyme, where the nucleotide sequence encoding the biosynthetic pathway enzyme is under control of an inducible promoter. In these embodiments, an inducer is added to the culture medium. In some embodiments, both inducer and substrate are added to the culture medium.

One non-limiting example of terpene synthase genes that may be identified by the method of the present invention are amorphadiene synthase genes. When the functional biosynthetic genes sought to be identified are terpene synthase genes, the source for the exogenous nucleic acid is in some embodiments an isoprenoid-producing cell or organism. In other embodiments, the exogenous nucleic acid is a synthetic nucleic acid.

The intermediate in the terpene biosynthesis pathway is typically a prenyl diphosphate such as IPP, DMAPP, or a polyprenyl diphosphate. Polyprenyl diphosphates include, but are not limited to, geranyl diphosphate, farnesyl diphosphate, geranylgeranyl diphosphate, geranylfarnesyl diphosphate, hexaprenyl diphosphate, heptaprenyl diphosphate, octaprenyl diphosphate, solanesyl diphosphate, decaprenyl diphosphate, undecaprenyl diphosphate, dehydrodolichyl diphosphate, natural rubber, and a Z-isoprenyl diphosphate.

When the concentration of the prenyl diphosphate intermediate reaches a certain level, the genetically modified host cell exhibits growth inhibition, which may be accompanied by cell death, mutation of cellular DNA, or entry of the cell into a quiescent state. The growth inhibition of the genetically modified host cell is relieved if the exogenous nucleic acid comprises a nucleotide sequence encoding a terpene synthase gene. The terpene synthase is produced in the cell and catalyzes a modification of the prenyl diphosphate intermediate, such that the intermediate is no longer growth inhibiting and/or the level of the intermediate is reduced to a level that is not growth inhibiting. Thus, in those situations where the genetically modified host cell exhibits relief of growth inhibition, the exogenous nucleic acid is isolated and characterized.

Exogenous nucleic acids that relieve the growth inhibition are isolated and characterized for the presence of a nucleotide sequence that encodes a terpene synthase and/or other enzymes that modify the intermediate or a downstream product. For example, the terpene synthase encoded by the exogenous nucleic acid will catalyze the conversion of a prenyl diphosphate to form a terpene.

As non-limiting examples, a terpene synthase identified using a subject screening method will catalyze the exemplary prenyl diphosphates listed above to form the following terpenes: IPP will be modified by a terpene synthase to form a 5-carbon hemiterpene; DMAPP will be modified by a terpene synthase to form a 5-carbon hemiterpene; GPP will be modified by a terpene synthase to form a 10-carbon monoterpene; FPP will be modified by a terpene synthase to from a 15-carbon sesquiterpene; and GGPP will be modified by a terpene synthase to form a 20-carbon diterpene. Of course it is understood that this list is merely exemplary and that the method of the claimed invention may be used to identify terpene cyclase genes that catalyze the modification of any prenyl diphosphate.

Because the amount of terpenes isolated from the genetically modified host cell is dependent on the amount of prenyl diphosphate generated in genetically modified host cell, increasing the amount of prenyl diphosphate will consequently increase the amount of terpenes isolated from the host microorganism.

Where a subject method is a screening method to identify a gene product having activity in a terpene biosynthetic pathway, the genetically modified host cell will in some embodiments be engineered to convert acetyl-CoA or mevalonate to a prenyl diphosphate.

In some embodiments, a subject screening method will identify candidate gene products that modify a product of a terpene synthase. As an example, the crtN gene was found in *Heliobacillus mobilis* (Xiang et al. (1988) *Proc. Natl. Acad. Sci. USA* 95:14851-14856) to encode diapophytoene dehydrogenase is a part of the carotenoid biosynthesis pathway. Thus, in some embodiments, a subject screening method will identify multiple (two or more) genes products that are active in a terpene biosynthetic pathway). For example, in some embodiments, a subject screening method will identify an operon that encodes multiple enzymes in a terpene biosynthetic pathway.

Exemplary Embodiments

Any of the above-described genetically modified cells can be used in a subject screening method. In some embodiments, a subject genetically modified cell library is used in a subject screening method. The following are non-limiting examples of use of a subject genetically modified cell in a subject screening method.

In some embodiments, the genetically modified host cells are prokaryotic cells that comprise a nucleic acid comprising nucleotide sequences encoding acetoacetyl-CoA thiolase, HMGS, HMGR, MK, PMK, MPD, IDI, and an prenyl transferase, where the nucleotide sequences are part of a transcriptional unit operably linked to an inducible promoter, and where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. When the inducer is added to the medium, the enzymes are synthesized, and growth-inhibiting (e.g., toxic, or cell death-inducing) amounts of the polyprenyl diphosphate intermediate are produced. When death is detected in control cells, survival of polyprenyl diphosphate intermediate-induced death is detected in test cells into which exogenous nucleic acids were introduced. In some embodiments, the exogenous nucleic acid is isolated from the test cells.

For example, in some embodiments, the genetically modified host cells are prokaryotic cells that comprise a nucleic acid comprising nucleotide sequences encoding acetoacetyl-CoA thiolase, HMGS, HMGR, MK, PMK, MPD, IDI, and an FPP synthase, where the nucleotide sequences are part of a transcriptional unit operably linked to an inducible promoter. When the inducer is added to the medium, the enzymes are synthesized, and growth-inhibiting (e.g., toxic, or cell death-inducing) amounts of the terpene biosynthetic pathway intermediate FPP are produced. When death is detected in control cells, survival of FPP-induced death is detected in test cells into which exogenous nucleic acids were introduced. In some embodiments, the exogenous nucleic acid is isolated from the test cells.

In other embodiments, the genetically modified host cells are prokaryotic cells that comprise a first nucleic acid that comprises nucleotide sequences encoding acetoacetyl-CoA thiolase, HMGS, HMGR, MK, PMK, MPD, and IDI, where the nucleotide sequences are part of a transcriptional unit operably linked to an inducible promoter; and a second nucleic acid comprising a nucleotide sequence encoding a prenyl transferase, where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. Typically, the nucleotide sequence encoding the prenyl transferase is also operably linked to an inducible promoter, which may be induced by the same or different inducer as the inducible promoter operably linked to the nucleotide sequences encoding acetoacetyl-CoA thiolase, HMGS, HMGR, MK, PMK, MPD, and IDI. When the inducer(s) is added to the medium, the enzymes are synthesized, and toxic amounts of the terpene biosynthetic pathway polyprenyl diphosphate intermediate are produced. When death is detected in control cells, survival of polyprenyl diphosphate intermediate-induced death is detected in test cells into which exogenous nucleic acids were introduced. In some embodiments, the exogenous nucleic acid is isolated from the test cells.

In some embodiments, the genetically modified host cells are prokaryotic cells that comprise a nucleic acid comprising nucleotide sequences encoding MK, PMK, MPD, IDI, and an prenyl transferase, where the nucleotide sequences are part of a transcriptional unit operably linked to an inducible promoter, and where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. When the inducer and mevalonate are added to the medium, the enzymes are synthesized, and growth-inhibiting (e.g., toxic, or cell death-inducing) amounts of the polyprenyl diphosphate intermediate are produced. When death is detected in control cells, survival of polyprenyl diphosphate intermediate-induced death is detected in test cells into which exogenous nucleic acids were introduced. In some embodiments, the exogenous nucleic acid is isolated from the test cells.

For example, in some embodiments, the genetically modified host cells are prokaryotic cells that comprise a nucleic acid comprising nucleotide sequences encoding MK, PMK, MPD, IDI, and an FPP synthase, where the nucleotide sequences are part of a transcriptional unit operably linked to an inducible promoter. When the inducer and mevalonate are added to the medium, the enzymes are synthesized, and growth-inhibiting (e.g., toxic, or cell death-inducing) amounts of the terpene biosynthetic pathway intermediate FPP are produced. When death is detected in control cells, survival of FPP-induced death is detected in test cells into which exogenous nucleic acids were introduced. In some embodiments, the exogenous nucleic acid is isolated from the test cells.

In other embodiments, the genetically modified host cells are prokaryotic cells that comprise a first nucleic acid that comprises nucleotide sequences encoding MK, PMK, MPD, and IDI, where the nucleotide sequences are part of a transcriptional unit operably linked to an inducible promoter; and a second nucleic acid comprising a nucleotide sequence encoding a prenyl transferase, where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. Typically, the nucleotide sequence encoding the prenyl transferase is also operably linked to an inducible promoter, which may be induced by the same or different inducer as the inducible promoter operably linked to the nucleotide sequences encoding MK, PMK, MPD, and IDI. When the inducer(s) and mevalonate are added to the medium, the enzymes are synthesized, and toxic amounts of the terpene biosynthetic pathway polyprenyl diphosphate intermediate are produced. When death is detected in control cells, survival of polyprenyl diphosphate intermediate-induced death is detected in test cells into which exogenous nucleic acids were introduced. In some embodiments, the exogenous nucleic acid is isolated from the test cells.

In other embodiments, the genetically modified host cells are eukaryotic cells that comprise a nucleic acid(s) that comprises nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase, where the nucleotide sequences are operably linked to an inducible promoter; and a second nucleic acid comprising a nucleotide sequence encoding a prenyl transferase, where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. When the inducer is are added to the medium, the enzymes are synthesized, and toxic amounts of the terpene biosynthetic pathway polyprenyl diphosphate intermediate are produced. When death is detected in control cells, survival of polyprenyl diphosphate intermediate-induced death is detected in test cells into which exogenous nucleic acids were introduced. In some embodiments; the exogenous nucleic acid is isolated from the test cells.

In other embodiments, the genetically modified host cells are eukaryotic cells that comprise a nucleic acid(s) that comprises nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase, where the nucleotide sequences are operably linked to an inducible promoter; and a second nucleic acid comprising a nucleotide sequence encoding a prenyl transferase, where the prenyl transferase is selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. When the inducer and methylerythritol are added to the medium, the enzymes are synthesized, and toxic amounts of the terpene biosynthetic pathway polyprenyl diphosphate intermediate are produced. When death is detected in control cells, survival of polyprenyl diphosphate intermediate-induced death is detected in test cells into which exogenous nucleic acids were introduced. In some embodiments, the exogenous nucleic acid is isolated from the test cells.

Increasing the Intracellular Concentration of a Biosynthetic Pathway Intermediate In some embodiments, the intracellular concentration (e.g., the concentration of the intermediate in the genetically modified host cell) of the biosynthetic pathway intermediate is increased. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

Increasing the Amount of a Substrate in the Culture Medium

In some embodiments, genetically modified host cells for use in a subject method are genetically modified to produce gene products in the MEV pathway. In some of these embodiments, the intracellular concentration of a terpene biosynthetic pathway intermediate is increased by increasing the amount of mevalonate in the culture medium. The concentration of mevalonate in the culture medium is generally in the range of from about 1 mM to about 50 mM, e.g., from about 1 mM to about 5 mM, from about 5 mM to about 10 mM, from about 10 mM to about 20 mM, from about 20 mM to about 30 mM, from about 30 mM to about 40 mM, or from about 40 mM to about 50 mM.

In some embodiments, genetically modified host cells for use in a subject method are genetically modified to produce gene products in the DXP pathway. Thus, in some embodiments, the genetically modified host cell is capable of converting 1-deoxy-D-xylulose-5-phosphate to a prenyl diphosphate. In some embodiments, the genetically modified host cell comprises a nucleic acid comprising nucleotide sequences encoding DXP pathway enzymes 1-6. In these embodiments, the genetically modified host cell is placed in a 1-deoxy-D-xylulose 5-phosphate-rich growth medium, thereby increasing intracellular concentrations of prenyl diphosphates until growth of the genetically modified host cell is inhibited. The concentration of 1-deoxy-D-xylulose-5-phosphate in the culture medium is generally in the range of from about 1 mM to about 50 mM, e.g., from about 1 mM to about 5 mM, from about 5 mM to about 10 mM, from about 10 mM to about 20 mM, from about 20 mM to about 30 mM, from about 30 mM to about 40 mM, or from about 40 mM to about 50 mM. In other embodiments, the host the genetically modified host cell comprises a nucleic acid comprising nucleotide sequences encoding DXP pathway enzymes 3-6. In these embodiments, the genetically modified host cell is placed in a methylerythritol-rich growth medium, thereby increasing intracellular concentrations of prenyl diphosphates until growth of the genetically modified host cell is inhibited. The concentration of methylerythritol in the culture medium is generally in the range of from about 1 mM to about 50 mM, e.g., from about 1 mM to about 5 mM, from about 5 mM to about 10 mM, from about 10 mM to about 20 mM, from about 20 mM to about 30 mM, from about 30 mM to about 40 mM, or from about 40 mM to about 50 mM.

Increasing Catalytic Activity of an Enzyme Having Activity in the Biosynthetic Pathway In some embodiments, the intracellular concentration of a biosynthetic pathway intermediate is increased by increasing catalytic activity of an enzyme in the biosynthetic pathway that leads to production of the intermediate. For example, where the genetically modified host cells for use in a subject method are genetically modified to produce gene products in the MEV pathway, the nucleotide sequence encoding MK and/or PMK and/or MPD are modified such that the encoded MK and/or PMK and/or MPD have increased catalytic activity, such that the amount of the growth-inhibiting terpene biosynthetic pathway intermediate is increased.

Nucleic acids comprising nucleotide sequences encoding variant terpene biosynthetic pathway enzymes (e.g., MK and/or PMK and/or MPD) that exhibit increase catalytic activity are generated using any of a variety of methods, e.g., by random mutagenesis (e.g., using chemical mutagenesis methods, radiation-induced mutagenesis, PCR-based mutagenesis methods, and the like).

Whether a nucleotide sequence encodes a variant terpene biosynthetic pathway enzyme(s) (e.g., MK and/or PMK and/or MPD) that exhibits increase catalytic activity can be readily determined. For example, a nucleic acid comprising a nucleotide sequence encoding a variant terpene biosynthetic pathway enzyme(s) (e.g., MK and/or PMK and/or MPD) that exhibits increase catalytic activity is introduced into a prokaryotic or eukaryotic host cell. In the presence of mevalonate in the culture medium, cells that exhibit growth inhibition at a faster rate than other cells may include a nucleic acid comprising a nucleotide sequence encoding a variant terpene biosynthetic pathway enzyme(s) (e.g., MK and/or PMK and/or MPD) that exhibits increase catalytic activity. For example, a nucleic acid comprising a nucleotide sequence encoding a variant terpene biosynthetic pathway enzyme(s) (e.g., MK and/or PMK and/or MPD) that exhibits increase catalytic activity can be identified as follows. Where the genetically modified host cell is a prokaryotic cell such as a bacterium, the genetically modified host cell is cultured in vitro under conditions such that the intermediate is produced; and the bacterium is plated out on a solid bacterial culture medium. Where intracellular concentrations of the intermediate inhibit cell growth, the colony size of the bacterial cells exhibiting growth inhibition will be smaller than the colony size of bacterial cells not exhibiting growth inhibition. Smaller colonies will in some embodiments contain nucleic acids encoding terpene biosynthetic pathway enzymes that have increased catalytic activity.

A similar scheme can be carried out to identify a nucleic acid comprising a nucleotide sequence encoding a variant terpene biosynthetic pathway enzyme(s) in the DXP pathway that exhibits increase catalytic activity. The genetically modified host cell may be screened for increased production of 1-deoxy-D-xylulose-5-phosphate (DXP) pathway products such as: (a) 1-deoxy-D-xylulose-5-phosphate; (b) 2-C-methyl-D-erythritol-4-phosphate; (c) 4-diphosphocytidyl-2-C-methyl-D-erythritol-2-phosphate; (d) 2-C-methylerythritol-2,4-cyclodiphosphate; and (e) 1-hydroxy-2-methyl-2-(E)-butenyl-4-diphosphate, such that DXP pathway genes isolated from the clones are selected as improved DXP pathway genes which are introduced into the host microorganism to engineer cells capable of producing increased amounts of the prenyl diphosphates.

Increasing Intracellular Production of a Primary Substrate

In some embodiments, the concentration of the prenyl diphosphate intermediate is increased by increasing the concentration of the primary substrate (e.g., acetyl-CoA, mevalonate, pyruvate, glyceraldehyde-3-phosphate, and the like) in the host cell. For example, in some embodiments, the intracellular concentration of a growth-inhibiting terpene biosynthetic pathway intermediate, flux through the MEV pathway is increased by increasing the production of acetyl-CoA, the universal precursor of the MEV pathway. Increasing production of acetyl-CoA is achieved by increasing the concentration of glucose in the culture medium.

In other embodiments, the intracellular concentration of acetyl-CoA in the host cell is increased by reducing the level and/or activity of phosphotransacetylase in the host cell. In some embodiments, the level of phosphotransacetylase in the host cell is reduced by rendering the gene encoding phosphotransacetylase non-functional. The pta gene can be rendered non-functional in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like. *E. coli* secretes a significant fraction of intracellular acetyl-CoA in the form of acetate into the medium. Holms (1986) *Curr Top Cell Regul.* 28:69-105. Deleting the gene encoding phosphotransacetylase, pta, the first enzyme responsible for transforming acetyl-CoA into acetate, has been shown to significantly reduce acetate secretion and increase the secretion of pyruvate, lactate, and other metabolites, while decreasing the growth rate on glucose. Chang (1999) *J. Bacteriol.* 181(21): 6656-63.

In some embodiments, the pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci USA* 97(12): p. 6640-5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

In some embodiments, genetically modified host cells for use in a subject method are genetically modified to produce gene products in the DXP pathway. Thus, in some embodiments, the genetically modified host cell is capable of converting 1-deoxy-D-xylulose-5-phosphate to a prenyl diphosphate. In these embodiments, the genetically modified host cell is placed in a 1-deoxy-D-xylulose 5-phosphate-rich growth medium, thereby increasing intracellular concentrations of prenyl diphosphates until growth of the genetically modified host cell is inhibited. The intracellular concentrations of the prenyl diphosphates are increased by increasing flux through the 1-deoxy-D-xylulose-5-phosphate (DXP) pathway by increasing production of glyceraldehydes 3-phosphate or pyruvate.

Kits

The present invention further provides a kit for carrying out a subject screening method. A subject kit will include at least one genetically modified host cell, where the host cell is genetically modified with a nucleic acid comprising a nucleotide sequence encoding a biosynthetic pathway enzyme. Under appropriate culture conditions, synthesis of the enzyme in the genetically modified host cell results in conversion of a substrate for the enzyme into a biosynthetic pathway intermediate, which intermediate is produced in an amount effective to inhibit growth of the genetically modified host cell. In some embodiments, the kit will further include a substrate for the biosynthetic pathway enzyme.

In some embodiments, a subject kit comprises any of the above-described subject genetically modified host cell libraries. In some embodiments, the member genetically modified host cell of a subject genetically modified host cell library is provided in separate containers (e.g., vials). In some embodiments, a subject kit will comprise two or more separate containers, each comprising genetically modified host cells, where the genetically modified host cells are cells that have been genetically modified with one or more nucleic acids comprising nucleotide sequences encoding MEV pathway enzymes; and further nucleic acid comprising a nucleotide sequence encoding a prenyl transferase, where each member genetically modified host cell comprises a nucleotide sequence encoding a different prenyl transferase. In some embodiments, a subject kit will comprise two or more separate containers, each comprising genetically modified host cells genetically modified with one or more nucleic acids comprising nucleotide sequences encoding DXP pathway enzymes; and further nucleic acid comprising a nucleotide sequence encoding a prenyl transferase, where each member genetically modified host cell comprises a nucleotide sequence encoding a different prenyl transferase. In other embodiments, the member genetically modified host cells are not in separate containers; instead, the member genetically modified host cells are packaged in the same container as a mixed population.

In some embodiments, a subject kit comprises a subject bacterial library comprising two or more members, each member being a bacterium that has been genetically modified to comprise one or more nucleic acids comprising nucleotide sequences encoding MEV pathway enzymes, and a nucleotide sequence encoding a different prenyl transferase selected from a GPP synthase, an FPP synthase, a GGPP synthase, a GFPP synthase, a HexPP synthase, a HepPP synthase, an OPP synthase, an SPP synthase, a DPP synthase, an NPP synthase, and a UPP synthase. Thus, e.g., in some embodiments, a subject kit will comprise a first bacterium genetically modified with one or more nucleic acids comprising nucleotide sequences encoding MK, PMK, MPD, and IDI; and a further nucleic acid comprising a nucleotide sequence encoding a GPP synthase; a second bacterium genetically modified with one or more nucleic acids comprising nucleotide sequences encoding MK, PMK, MPD, and IDI; and a further nucleic acid comprising a nucleotide sequence encoding an FPP synthase; a third bacterium genetically modified with one or more nucleic acids comprising nucleotide sequences encoding MK, PMK, MPD, and IDI; and a further nucleic acid comprising a nucleotide sequence encoding a GGPP synthase; a fourth bacterium genetically modified with one or more nucleic acids comprising nucleotide sequences encoding MK, PMK, MPD, and IDI; and a further nucleic acid comprising a nucleotide sequence encoding a GFPP synthase; a fifth bacterium genetically modified with one or more nucleic acids comprising nucleotide sequences encoding MK, PMK, MPD, and IDI; and a further nucleic acid comprising a nucleotide sequence encoding a HexPP synthase; a sixth bacterium genetically modified with one or more nucleic acids comprising nucleotide sequences encoding MK, PMK, MPD, and IDI; and a further nucleic acid comprising a nucleotide sequence encoding a HepPP synthase; a seventh bacterium genetically modified with one or more nucleic acids comprising nucleotide sequences encoding MK, PMK, MPD, and IDI; and a further nucleic acid comprising a nucleotide sequence encoding an OPP synthase; an eighth bacterium genetically modified with one or more nucleic acids comprising nucleotide sequences encoding MK, PMK, MPD, and IDI; and a further nucleic acid comprising a nucleotide sequence encoding an SPP synthase; a ninth bacterium genetically modified with one or more nucleic acids comprising nucleotide sequences encoding MK, PMK, MPD, and IDI; and a further nucleic acid comprising a nucleotide sequence encoding a DPP synthase; a tenth bacterium genetically modified with one or more nucleic acids comprising nucleotide sequences encoding MK, PMK, MPD, and IDI; and a further nucleic acid comprising a nucleotide sequence encoding an NPP synthase; and an eleventh bacterium genetically modified with one or more nucleic acids comprising nucleotide sequences encoding MK, PMK, MPD, and IDI; and a further nucleic acid comprising a nucleotide sequence encoding a UPP synthase.

In other embodiments, a subject kit will comprise a first bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a GPP synthase; a second bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding an FPP synthase; a third bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a GGPP synthase; a fourth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a GFPP synthase; a fifth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a HexPP synthase; a sixth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a HepPP synthase; a seventh bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding an OPP synthase; an eighth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding an SPP synthase; a ninth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a DPP synthase; a tenth bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding an NPP synthase; and an eleventh bacterium genetically modified with one or more nucleic acids comprising nucleotide sequences encoding acetoacetyl-CoA thiolase, HMGS, HMGR, MK, PMK, MPD, and IDI; and a further nucleic acid comprising a nucleotide sequence encoding a UPP synthase.

In some of the above-described embodiments, where the genetically modified host cell is a prokaryotic cell that is genetically modified with a nucleic acid(s) comprising nucleotide sequences encoding MEV pathway enzymes, the host cell further comprises a functionally disabled endogenous pta gene, e.g., a deletion of all or part of an endogenous pta gene. In some of the above-described embodiments, where the genetically modified host cell is a prokaryotic cell that is genetically modified with a nucleic acid(s) comprising nucleotide sequences encoding MEV pathway enzymes, the host cell further comprises a functionally disabled endogenous DXP pathway gene, e.g., a deletion of all or part of an IspC gene.

In other embodiments, a subject kit will comprise a first eukaryotic cell (e.g., a yeast cell) genetically modified with one or more nucleic acids comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase (DXP pathway enzymes 1-7); and a further nucleic acid comprising a nucleotide sequence encoding a GPP synthase; a second eukaryotic cell (e.g., a yeast cell) genetically modified with one or more nucleic acids comprising nucleotide sequences encoding DXP pathway enzymes 1-7; and a further nucleic acid comprising a nucleotide sequence encoding an FPP synthase; a third eukaryotic cell (e.g., a yeast cell) genetically modified with one or more nucleic acids comprising nucleotide sequences encoding DXP pathway enzymes 1-7; and a further nucleic acid comprising a nucleotide sequence encoding a GGPP synthase; a fourth eukaryotic cell (e.g., a yeast cell) genetically modified with one or more nucleic acids comprising nucleotide sequences encoding DXP pathway enzymes 1-7; and a further nucleic acid comprising a nucleotide sequence encoding a GFPP synthase; a fifth eukaryotic cell (e.g., a yeast cell) genetically modified with one or more nucleic acids comprising nucleotide sequences encoding DXP pathway enzymes 1-7; and a further nucleic acid comprising a nucleotide sequence encoding a HexPP synthase; a sixth eukaryotic cell (e.g., a yeast cell) genetically modified with one or more nucleic acids comprising nucleotide sequences encoding DXP pathway enzymes 1-7; and a further nucleic acid comprising a nucleotide sequence encoding a HepPP synthase; a seventh eukaryotic cell (e.g., a yeast cell) genetically modified with one or more nucleic acids comprising nucleotide sequences encoding DXP pathway enzymes 1-7; and a further nucleic acid comprising a nucleotide sequence encoding an OPP synthase; an eighth eukaryotic cell (e.g., a yeast cell) genetically modified with one or more nucleic acids comprising nucleotide sequences encoding DXP pathway enzymes 1-7; and a further nucleic acid comprising a nucleotide sequence encoding an SPP synthase; a ninth eukaryotic cell (e.g., a yeast cell) genetically modified with one or more nucleic acids comprising nucleotide sequences encoding DXP pathway enzymes 1-7; and a further nucleic acid comprising a nucleotide sequence encoding a DPP synthase; a tenth eukaryotic cell (e.g., a yeast cell) genetically modified with one or more nucleic acids comprising nucleotide sequences encoding DXP pathway enzymes 1-7; and a further nucleic acid comprising a nucleotide sequence encoding an NPP synthase; and an eleventh eukaryotic cell (e.g., a yeast cell) genetically modified with one or more nucleic acids comprising nucleotide sequences encoding DXP pathway enzymes 1-7; and a further nucleic acid comprising a nucleotide sequence encoding a UPP synthase.

In other embodiments, a subject kit will comprise a first eukaryotic cell (e.g., a yeast cell) genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase (DXP pathway enzymes 3-7); and a further nucleic acid comprising a nucleotide sequence encoding a GPP synthase; a second eukaryotic cell (e.g., a yeast cell) genetically modified with one or more nucleic acids comprising nucleotide sequences encoding DXP pathway enzymes 3-7; and a further nucleic acid comprising a nucleotide sequence encoding an FPP synthase; a third eukaryotic cell (e.g., a yeast cell) genetically modified with one or more nucleic acids comprising nucleotide sequences encoding DXP pathway enzymes 3-7; and a further nucleic acid comprising a nucleotide sequence encoding a GGPP synthase; a fourth eukaryotic cell (e.g., a yeast cell) genetically modified with one or more nucleic acids comprising nucleotide sequences encoding DXP pathway enzymes 3-7; and a further nucleic acid comprising a nucleotide sequence encoding a GFPP synthase; a fifth eukaryotic cell (e.g., a yeast cell) genetically modified with one or more nucleic acids comprising nucleotide sequences encoding DXP pathway enzymes 3-7; and a further nucleic acid comprising a nucleotide sequence encoding a HexPP synthase; a sixth eukaryotic cell (e.g., a yeast cell) genetically modified with one or more nucleic acids comprising nucleotide sequences encoding DXP pathway enzymes 3-7; and a further nucleic acid comprising a nucleotide sequence encoding a HepPP synthase; a seventh eukaryotic cell (e.g., a yeast cell) genetically modified with one or more nucleic acids comprising nucleotide sequences encoding DXP pathway enzymes 3-7; and a further nucleic acid comprising a nucleotide sequence encoding an OPP synthase; an eighth eukaryotic cell (e.g., a yeast cell) genetically modified with one or more nucleic acids comprising nucleotide sequences encoding DXP pathway enzymes 3-7; and a further nucleic acid comprising a nucleotide sequence encoding an SPP synthase; a ninth eukaryotic cell (e.g., a yeast cell) genetically modified with one or more nucleic acids comprising nucleotide sequences encoding DXP pathway enzymes 3-7; and a further nucleic acid comprising a nucleotide sequence encoding a DPP synthase; a tenth eukaryotic cell (e.g., a yeast cell) genetically modified with one or more nucleic acids comprising nucleotide sequences encoding DXP pathway enzymes 3-7; and a further nucleic acid comprising a nucleotide sequence encoding an NPP synthase; and an eleventh eukaryotic cell (e.g., a yeast cell) genetically modified with one or more nucleic acids comprising nucleotide sequences encoding DXP pathway enzymes 3-7; and a further nucleic acid comprising a nucleotide sequence encoding a UPP synthase.

In other embodiments, a subject kit will comprise a first eukaryotic cell (e.g., a yeast cell) genetically modified with one or more nucleic acids comprising nucleotide sequences encoding 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase (DXP pathway enzymes 1-6); and a further nucleic acid comprising a nucleotide sequence encoding a GPP synthase; a second eukaryotic cell (e.g., a yeast cell) genetically modified with one or more nucleic acids comprising nucleotide sequences encoding DXP pathway enzymes 1-6; and a further nucleic acid comprising a nucleotide sequence encoding an FPP synthase; a third eukaryotic cell (e.g., a yeast cell) genetically modified with one or more nucleic acids comprising nucleotide sequences encoding DXP pathway enzymes 1-6; and a further nucleic acid comprising a nucleotide sequence encoding a GGPP synthase; a fourth eukaryotic cell (e.g., a yeast cell) genetically modified with one or more nucleic acids comprising nucleotide sequences encoding DXP pathway enzymes 1-6; and a further nucleic acid comprising a nucleotide sequence encoding a GFPP synthase; a fifth eukaryotic cell (e.g., a yeast cell) genetically modified with one or more nucleic acids comprising nucleotide sequences encoding DXP pathway enzymes 1-6; and a further nucleic acid comprising a nucleotide sequence encoding a HexPP synthase; a sixth eukaryotic cell (e.g., a yeast cell) genetically modified with one or more nucleic acids comprising nucleotide sequences encoding DXP pathway enzymes 1-6; and a further nucleic acid comprising a nucleotide sequence encoding a HepPP synthase; a seventh eukaryotic cell (e.g., a yeast cell) genetically modified with one or more nucleic acids comprising nucleotide sequences encoding DXP pathway enzymes 1-6; and a further nucleic acid comprising a nucleotide sequence encoding an OPP synthase; an eighth eukaryotic cell (e.g., a yeast cell) genetically modified with one or more nucleic acids comprising a nucleotide sequences encoding DXP pathway enzymes 1-6; and a further nucleic acid comprising a nucleotide sequence encoding an SPP synthase; a ninth eukaryotic cell (e.g., a yeast cell) genetically modified with one or more nucleic acids comprising nucleotide sequences encoding DXP pathway enzymes 1-6; and a further nucleic acid comprising a nucleotide sequence encoding a DPP synthase; a tenth eukaryotic cell (e.g., a yeast cell) genetically modified with one or more nucleic acids comprising nucleotide sequences encoding DXP pathway enzymes 1-6; and a further nucleic acid comprising a nucleotide sequence encoding an NPP synthase; and an eleventh eukaryotic cell (e.g., a yeast cell) genetically modified with one or more nucleic acids comprising nucleotide sequences encoding DXP pathway enzymes 1-6; and a further nucleic acid comprising a nucleotide sequence encoding a UPP synthase.

In other embodiments, a subject kit will comprise a first eukaryotic cell (e.g., a yeast cell) genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase (DXP pathway enzymes 3-6); and a further nucleic acid comprising a nucleotide sequence encoding a GPP synthase; a second eukaryotic cell (e.g., a yeast cell) genetically modified with one or more nucleic acids comprising nucleotide sequences encoding DXP pathway enzymes 3-6; and a further nucleic acid comprising a nucleotide sequence encoding an FPP synthase; a third eukaryotic cell (e.g., a yeast cell) genetically modified with one or more nucleic acids comprising nucleotide sequences encoding DXP pathway enzymes 3-6; and a further nucleic acid comprising a nucleotide sequence encoding a GGPP synthase; a fourth eukaryotic cell (e.g., a yeast cell) genetically modified with one or more nucleic acids comprising nucleotide sequences encoding DXP pathway enzymes 3-6; and a further nucleic acid comprising a nucleotide sequence encoding a GFPP synthase; a fifth eukaryotic cell (e.g., a yeast cell) genetically modified with one or more nucleic acids comprising nucleotide sequences encoding DXP pathway enzymes 3-6; and a further nucleic acid comprising a nucleotide sequence encoding a HexPP synthase; a sixth eukaryotic cell (e.g., a yeast cell) genetically modified with one or more nucleic acids comprising nucleotide sequences encoding DXP pathway enzymes 3-6; and a further nucleic acid comprising a nucleotide sequence encoding a HepPP synthase; a seventh eukaryotic cell (e.g., a yeast cell) genetically modified with one or more nucleic acids comprising nucleotide sequences encoding DXP pathway enzymes 3-6; and a further nucleic acid comprising a nucleotide sequence encoding an OPP synthase; an eighth eukaryotic cell (e.g., a yeast cell) genetically modified with one or more nucleic acids comprising nucleotide sequences encoding DXP pathway enzymes 3-6; and a further nucleic acid comprising a nucleotide sequence encoding an SPP synthase; a ninth eukaryotic cell (e.g., a yeast cell) genetically modified with one or more nucleic acids comprising nucleotide sequences encoding DXP pathway enzymes 3-6; and a further nucleic acid comprising a nucleotide sequence encoding a DPP synthase; a tenth eukaryotic cell (e.g., a yeast cell) genetically modified with one or more nucleic acids comprising nucleotide sequences encoding DXP pathway enzymes 3-6; and a further nucleic acid comprising a nucleotide sequence encoding an NPP synthase; and an eleventh eukaryotic cell (e.g., a yeast cell) genetically modified with one or more nucleic acids comprising nucleotide sequences encoding DXP pathway enzymes 3-6; and a further nucleic acid comprising a nucleotide sequence encoding a UPP synthase.

In some of the above-described embodiments, where the genetically modified host cell is a eukaryotic cell that is genetically modified with a nucleic acid(s) comprising nucleotide sequences encoding DXP pathway enzymes, the host cell further comprises a functionally disabled endogenous MEV pathway gene, e.g., a deletion of all or part of an endogenous MEV pathway gene, e.g., a deletion of all or part of an endogenous MK gene.

Typically, a plurality of each member genetically modified host cell is present in the population (or in each separate vial) e.g., a subject genetically modified host cell population comprises two or more member host cells, where from about 10 to about $10^2$, from about $10^2$ to about $10^4$, from about $10^4$ to about $10^6$, or from about $10^6$ to about $10^8$ or more of each member genetically modified host cell. In some embodiments, the cells are eukaryotic cells. In other embodiments, the cells are prokaryotic cells, e.g., bacterial cells.

A subject kit will in some embodiments further comprise a biosynthetic pathway substrate, e.g. mevalonate, or methylerythritol. A subject kit will in some embodiments further include a genetically modified host cell that serves as a positive control in a subject screening method, where the control genetically modified host cell comprises one or more nucleic acids encoding MEV pathway or DXP pathway gene products, a prenyl transferase, and known terpene synthase, where the known terpene synthase is one that modifies a product of the prenyl transferase. As one non-limiting example, in some embodiments, a positive control genetically modified host cell is a prokaryotic cell that comprises one or more nucleic acids that comprise nucleotide sequences encoding MK, PMK, MPK, an FPP synthase, and amorphadiene synthase. As another non-limiting example, in some embodiments, a positive control genetically modified host cell is a eukaryotic cell (e.g., a yeast cell) that comprises one or more nucleic acids encoding DXP pathway enzymes 1-7 (or 3-7, or 1-6, or 3-6), an FPP synthase, and amorphadiene synthase.

In some embodiments, the kit will further include an informational package insert describing the use of the component(s) of the kit in carrying out a subject screening method. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disc (CD), etc., on which the information has been recorded. Other suitable media include, audiovisual media, e.g., digital versatile disk (DVD), videotape, and the like. Yet another means that may be present is a website address which may be used via the Internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Example 1

Identifying Terpene Synthase Genes Using E. coli Genetically Modified to Synthesize an Intermediate in the Mevalonate (MEV) Pathway Materials and Methods
Strains and Media.

E. coli DH10B was used as the cloning and isoprenoid expression strain. The bacterial strains and plasmid used are shown in Table 1. E. coli DH10B: Gibco-Life Technologies; E. coli DYM1: Kuzuyama et al. (1999) Biosci. Biotechnol. Biochem. 63:776-778; pCR4: Invitrogen; pTrc99A: Pharmacia; pBBR1MCS-3: Kovach et al. (1995)Gene 166:175-176; pBAD33: Guzman et al. (1995) J. Bacteriol. 177:4121-4130; pAC-LYC04: Cunningham et al. (1994) 6:1107-1121.

TABLE 1

| Strain or Plasmid | Description |
|---|---|
| E. coli DH10B | |
| E. coli DYM1 | dxr⁻ E. coli strain |
| pCR4 | TA cloning vector; $Ap^R$ |
| pTrc99A | High-copy expression plasmid; $Ap^R$ |
| pBBR1MCS-3 | Low-copy broad-host expression plasmid; $Tc^R$ |
| pBAD33 | Low-copy broad-host expression plasmid; $Cm^R$ |
| pLac33 | Low-copy broad-host expression plasmid; $Cm^R$ |
| pSOE4 | SOE4 operon expression plasmid; $Cm^R$ |
| pAC-LYC04 | Plasmid expressing the IPP isomerase (ippHp) isolated from Haematococcus pluvialis; $Cm^R$ |
| pMevB | MevB operon expression plasmid.; $Tc^R$ |
| pMBI | MBI operon expression plasmid.; $Tc^R$ |
| pMBIS | MBIS operon expression plasmid; $Tc^R$ |
| pMevT | MevT operon expression plasmid; $Cm^R$ |
| pADS | Synthetic amorphadiene synthase expression plasmid; $Ap^R$ |

In Table 1, $Ap^R$ indicates ampicillin resistance, $Tc^R$ indicates tetracycline resistance, and $Cm^R$ indicates chloramphenicol resistance.

Nucleotide sequences of polymerase chain reaction (PCR) primers used are as follows:

| Primer | Sequence |
|---|---|
| MK-f | 5'-GATCTGCAGTAGGAGGAATTAACCATGCATTACCGTTCTTAACT-3' (SEQ ID NO:1) |
| MK-r | 5'-TTGATCTGCCTCCTATGAAGTCCATGGTAAATT-3' (SEQ ID NO:2) |
| PMK-f | 5'-ACTTCATAGGAGGCAGATCAAATGTCAGAGTTGAGAGCCTTC-3' (SEQ ID NO:3) |
| PMK-r | 5'-GAGTATTACCTCCTATTTATCAAGATAAGTTTC-3' (SEQ ID NO:4) |
| MPD-f | 5'-GATAAATAGGAGGTAATACTCATGACCGTTTACACAGCATCC-3' (SEQ ID NO:5) |
| MPD-r | 5'-TACCTGCAGTTATTCCTTTGGTAGACCAGT-3' (SEQ ID NO:6) |
| atoB-f | 5'-GATGTCGACTAGGAGGAATATAAAATGAAAAATTGTGTCATCGTC-3' (SEQ ID NO:7) |
| atoB-r | 5'-TTAGCTGTCCTCCTTAATTCAACCGTTCAATCAC-3' (SEQ ID NO:8) |

-continued

| Primer | Sequence |
|---|---|
| HMGS-f | 5'-GATGTCGACAGGAGGACAGCTAAATGAAACTCTCAACTAAACTTTG-3' (SEQ ID NO:9) |
| HMGS-r | 5'-AGTGTAATCCTCCTTATTTTTAACATCGTAAG-3' (SEQ ID NO:10) |
| tHMGR-f | 5'-TTAAAAAATAAGGAGGATTACACTATGGTTTTAACCAATAAAACAG-3' (SEQ ID NO:11) |
| tHMGR-r | 5'-ATCGTCGACTTAGGATTTAATGCAGGTGACGGACC-3' (SEQ ID NO:12) |
| idi-f | 5'-ATCCCGGGAGGAGGATTACTATATGCAAACGGAACACGTC-3' (SEQ ID NO:13) |
| idi-r | 5'-ATCCCGGGTTATTTAAGCTGGGTAAATG-3' (SEQ ID NO:14) |
| ispa-f | 5'-AGATCCGCGGAGGAGGAATGAGTAATGGACTTTCCGCAGCAAC-3' (SEQ ID NO:15) |
| ispa-r | 5'-AGTGAGAGCTCTTATTTATTACGCTGGATGATG-3' |
| dxs1 | 5'-TTGGGCTAGCAGGAGGAATTCACCATGAGTTTTGATATTGCCAAATAC-3' (SEQ ID NO:16) |
| dxs2 | 5'-TCTGAGCAACGAACGAAGCATATATTTATGTCCTCCAGGCCTTGATTTTG-3' (SEQ ID NO:17) |
| ippHp1 | 5'-CAAAATCAAGGCCTGGAGGACATAAATATATGCTTCGTTCGTTGCTCAGA-3' (SEQ ID NO:18) |
| ippHp2 | 5'-GCATCCATGGTATCATCCTCCGTTGATGTGATG-3' (SEQ ID NO:19) |
| ispa1 | 5'-TGATACCATGGACTTTCCGCAGCAACTCG-3' (SEQ ID NO:20) |
| ipsa2 | 5'-GTACATGCATTTATTTATTACGCTGGATGATG-3' (SEQ ID NO:21) |
| SOE-f | 5'-GGTACCGGGCCCCCCCTCGCCTCTAGAGTCGACTAGGAGGAATTCACCATGAGTTTTG-3' (SEQ ID NO:22) |

For the growth studies, the optical density (OD) of cultures expressing the various recombinant pathways was measured with a microtiter plate reader (SpectraMax, Molecular Devices) from 200 μl cultures of LB broth in 96-well plates incubated at 37° C. with continuous shaking. (±)-Mevalonolactone was purchased from Sigma-Aldrich (St. Louis, Mo.) and 2-C-methyl-D-erythritol was synthesized from citraconic anhydride according to the protocol of Duvold-et al. Duvold et al. (1997) *Tetrahedron Lett.* 38:4769-4772. The ispC mutant *E. coli* strain DYM1 (Kuzuyama et al. (1999) *Biosci. Biotechnol. Biochem.* 63:776-778) was used to test the functionality of the synthetic mevalonate operons. The DYM1 strain was propagated on LB medium containing 0.5 mM methylerithrytol (ME) and transformed DYM1 cells were first allowed to recover on plates supplemented with ME before streaking them on test media. Media used to test the functionality of the operons were supplemented with 1 mM DL-mevalonate prepared by mixing 1 volume of 2 M DL-mevalonolactone with 1.02 volumes of 2 M KOH and incubating at 37° C. for 30 min. Campos (2001) *Biochem. J.* 353:59-67.

Synthesis of Amorphadiene Synthase Gene

The synthetic amorphadiene synthase (ADS) gene was designed using Calcgene (Hale and Thompson (1998) *Protein Exper. Purif.* 12:185-188 (1998)) and the protein sequence of the synthase isolated by Mercke et al. (Mercke et al. (2000) *Arch. Biochem. Biophys.* 381:173-180). The nucleotide sequence of the synthetic ADS is shown in FIGS. 12A-C (SEQ ID NO:23 and 24). To assemble the ADS gene, each of the 84 overlapping oligonucleotides (Gibco BRL), was dissolved in dH$_2$O a final concentration of 100 μM. A mixture was prepared by combining 10 μL of each of the individual oligonucleotides. The first PCR reaction in the two-step PCR assembly of ADS contained in 100 μL, 1×Pfu polymerase buffer (20 mM Tris-HCl pH 8.8, 2 mM MgSO$_4$ 10 mM KCl, 10 mM (NH$_4$)$_2$SO$_4$, 0.1% Triton X100, 0.1% mg/mL BSA), 0.25 mM of each dNTP, 1 μM of oligonucleotides mixture and 5 U Pfu polymerase (Stratagene). The PCR cycling program was 94° C. for 30 s, 40° C. for 2 min, 72° C. for 10 s followed by 40 cycles of 94° C. for 15 s, 40° C. for 30 s, 72° C. for 20 s+3 s per cycle. The second PCR reaction contained in 100 μL, 33 μL of the first assembly reaction, 1×Pfu buffer, 0.25 mM of each dNTP and 5 U Pfu polymerase. The PCR program for the second step of the assembly was as follows: 94° C. for 30 s, 40° C. for 10 s, 72° C. for 10 s followed by 25 cycles of 94° C. for 15 s, 40° C. for 30 s, 72° C. for 45 s+1 s per cycle. The DNA smear in the range of 1.7 kb was gel purified and used as template for a third and final PCR reaction containing in 100 μL, 1×Pfu buffer, 0.25 mM of each dNTP, 250 nM each of the two outside primers (T-1 and B-42), 10 μL of the gel purified DNA and 5 U Pfu polymerase. The PCR program was 40 cycles of 94° C. for 45 s and 72° C. for 4 min followed by a final step at 72° C. for 10 min. The expected 1.7 kb band was gel purified and ligated into pTrc99A using 5'-NcoI and 3'-XmaI sites designed into the gene sequence, thereby generating pADS. Two rounds of site-directed mutagenesis were needed to eliminate point mutations and generate a functional gene.

Construction of the DXP Pathway Operon

The dxs gene of *E. coli* was spliced to the IPP isomerase gene (ippHp) from pAC-LYC04 (Cunningham et al. (1994) *Plant Cell* 6:1107-1121) using overlapping extensions and PCR primers dxs1, dxs2, ippHp1 and ippHp2 (see above for primer sequences). The *E. coli* ispA gene was isolated by PCR using primers ispa1 and ipsa2 and ligated to the NcoI site 3' to ippHp. The three-gene DXP operon was amplified with primers SOE-f and ispa2 and cloned into the KpnI-PstI sites of pMevT thereby replacing the MevT operon with the SOE4 operon.

Construction of the Mevalonate Pathway Operons

The *Saccharomyces cerevisiae* mevalonate pathway was engineered as two separate, independently expressed operons. The genes encoding the last three enzymes of the biosynthetic pathway, mevalonate kinase (MK or ERG12), phosphomevalonate kinase (PMK or ERG18) and mevalonate pyrophosphate decarboxylase (MPD or ERG19) were isolated by PCR from chromosomal DNA preparations of *S. cerevisiae*, using the PCR primers shown above. The individual genes were spliced together (MevB, FIG. 13) using overlapping extensions from primers MK-f, MK-r, PMK-f, PMK-r, MPD-f and MPD-r. The genes encoding the first three enzymes of the mevalonate pathway, the acetoacetyl-CoA thiolase from *E. coli* (AACT or atoB), 3-hydroxy-3-methylglutaryl-CoA synthase (HMGS or ERG13) and a truncated version of 3-hydroxy-3-methylglutaryl-CoA reductase (Polakowsli et al. (1998) *Appl. Microbiol. Biotechnol.* 49:66-71) (tHMGR1) were isolated and spliced together as a single operon (MevT, FIG. 13) using the following primers: atoB-f, atoB-r, HMGS-f, HMGS-r, tHMGR-f and tHMGR-r. Individual genes were isolated via PCR using Pfu DNA polymerase and a standard PCR protocol. The synthetic operons were ligated into pCR4 (TA vector from Invitrogen), after the addition of 3' A-overhangs, and sequenced to ensure accuracy. The MevB operon was ligated into the PstI site of pBBR1MCS-3 (Kovach et al. (1995) *Gene* 166:175-176) generating pMevB. The idi gene was ligated into the XmaI site, 3' to MevB using primers idi-f and idi-r. The MBI operon was moved to the SalI-SacI sites of pBBR1MCS-3 to generate pMBI. The ispA gene from *E. coli* was ligated into the SacI-SacII sites of pMBI using primers ispa-f and ispa-r thereby producing pMBIS. The MevT operon was ligated into the XmaI-PstI sites of pBAD33 (Guzman et al. (1995) supra). To place the operon under control of the $P_{LAC}$ promoter, the araC-$P_{BAD}$ NsiI-XmaI fragment was replaced with the NsiI-XmaI fragment of pBBR1MCS thereby generating pMevT. To generate pLac33, the MevT operon was excised from pMevT with SalI.

Figure 13:
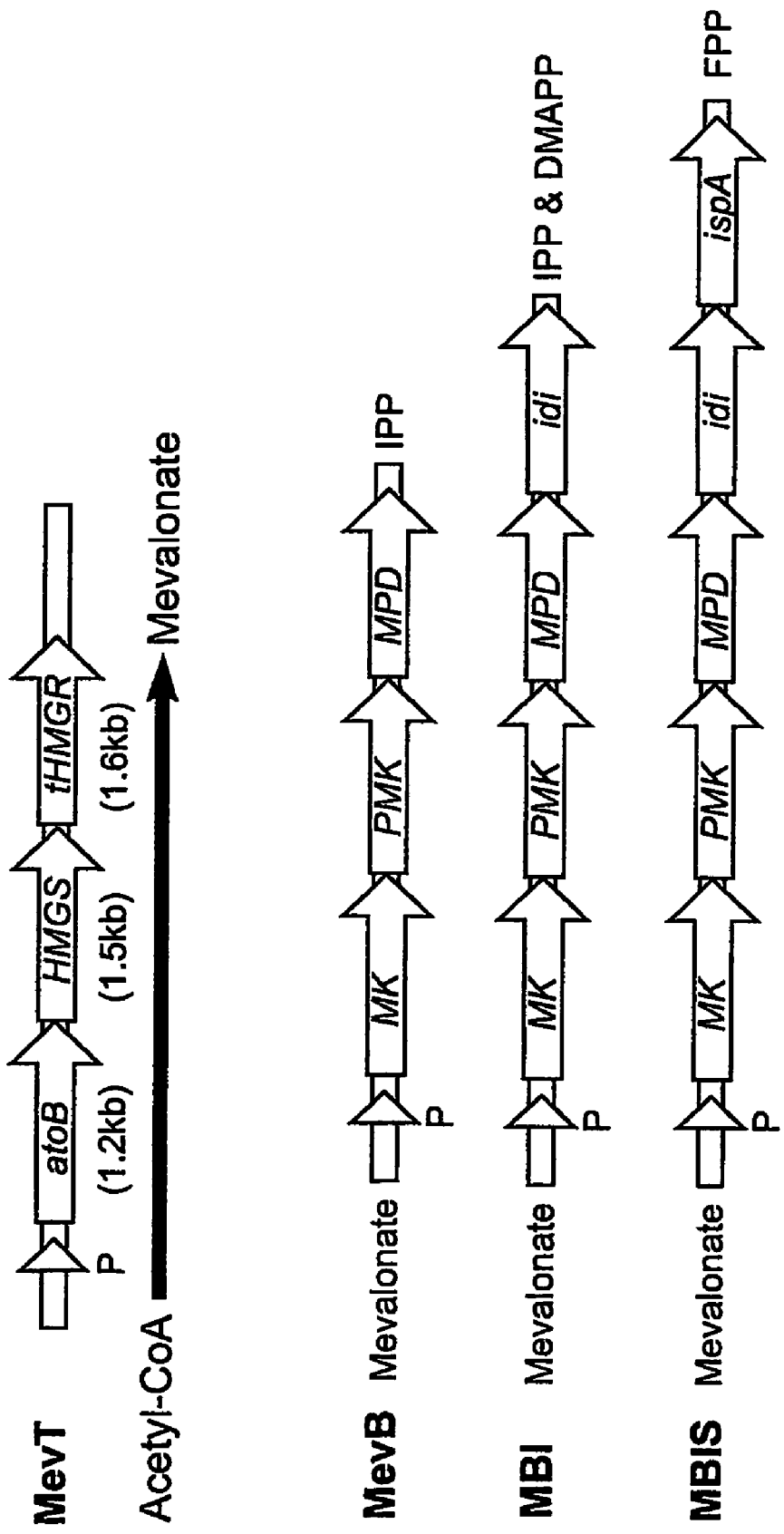
FIG. 13 depicts schematically the MevT, MevB, MBI, and MBIS operons.

Nucleotide sequences encoding acetoacetyl-CoA thiolase, HMGS, a truncated HMGR, MK, PMK, MPD, IDI, and FPP synthase are provided as SEQ ID NOs:25, 26, 27, 28, 29, 30, 34, and 35, respectively. Nucleotide sequences of the MevT operon, the MevB operon, the MBI operon, and the MBIS operon, as shown schematically in FIG. 13, are provided as SEQ ID NOs: 32, 33, 36, and 37, respectively. A single operon comprising nucleotide sequences encoding, in order from 5' to 3', IDI, acetoacetyl-CoA thiolase, HMGS, HMGR, MK, PMK, and MPD, is provided as SEQ ID NO:31. The single operon comprises a $P_{BAD}$ promoter (nt 1-18), and coding sequences for: IDI (nt 97-642), acetoacetyl-CoA thiolase (nt 684-1865), HMGS (nt 1882-3354), truncated HMGR (nt 3371-4876), MK (nt 4907-6235), PMK (nt 6251-7603), and MPD (nt 7619-8806).

GC-MS Analysis of Amorphadiene

Amorphadiene production by the various strains was measured by GC-MS as described in Martin et al. (Martin et al. (2001) *Biotechnol. Bioeng.* 75:497-503) by scanning only for two ions, the molecular ion (204 m/z) and the 189 m/z ion. Cells were grown in LB medium at 37° C. for 2 hrs and induced to express the ADS and the mevalonate pathway by the simultaneous addition of 0.5 mM IPTG and varying concentrations of (±)-mevalonate. Amorphadiene concentrations were converted to caryophyllene equivalents using a caryophyllene standard curve and the relative abundance of ions 189 and 204 m/z of the two compounds. The sesquiterpene caryophyllene was purchased from Sigma-Aldrich (St. Louis, Mo.).

Radio-HPLC Analysis of Intracellular Prenyl Pyrophosphates

Intracellular IPP+DMAPP and FPP levels were measured using a resting cell suspension assay supplemented with (R)-[5-$^3$H]-mevalonate (39 Ci/mmol, PerkinElmer Life Sciences, Boston Mass.). Cells induced with 0.5 mM IPTG cells then grown in LB broth at 37° C. to an $OD_{600}$ of ~0.6, harvested, washed once and suspended to 20-× concentration in 100 mM $KPO_4$ buffer (pH 7.4). Unlabeled (±)-mevalonate (10 mM) and $^3$H-radiolabeled (R)-mevalonate (60 µCi) were added to 8 mL of cell suspension and incubated at 37° C. Cells from 1.5 mL aliquots were washed twice with cold $KPO_4$ buffer and the intracellular IPP+DMAPP and FPP were extracted from cell pellets with 1 mL of methanol:chloroform (2:1). The cell extracts were dephosphorylated using potato acid phosphatase as previously described by Fujii et al. (Fujii et al. (1982) *Biochem. Biophys. Acta* 712:716-718). The prenyl alcohols were resolved on a reverse phase C-18 column (4.5 mm×250 mm 5µ particle size, Alltech) by HPLC (Agilent Technologies model 1100) using the method of Zhang and Poulter ((1993) *Anal. Biochem.* 213:356-361) and detected with a flow-through scintillation counter (Packard Bioscience, Radiomatic model 500TR).

Results

Genetically Modifying *E. coli* To Express the *S. cerevisiae* MEV Pathway

To increase the intracellular concentration of FPP substrate supplied to the amorphadiene synthase, the genes encoding the mevalonate-dependent isoprenoid pathway from *S. cerevisiae* were assembled into operons and expressed in *E. coli*. To simplify the task of engineering an eight-gene biosynthetic pathway, we divided the genes into two operons, referred to as the "top" and "bottom". The top operon, MevT, transforms the ubiquitous precursor acetyl-CoA to (R)-mevalonate in three enzymatic steps (FIG. 13). The bottom operon converts the (R)-mevalonate to IPP, DMAPP and/or FPP depending on the construct (FIG. 13). To test the functionality of the heterologous pathway, an *E. coli* strain deficient in isoprenoid synthesis (strain DYM1) was transformed with plasmids expressing the three different bottom operon constructs pMevB, pMBI and pMBIS (FIG. 13). Strain DYM1 has a deletion in the ispC gene, which encodes 1-deoxy-D-xylulose-5-phosphate reductoisomerase (Kuzuyama et al. (1999) supra) and therefore, cannot synthesize 2-C-methyl-D-erythritol 4-phosphate, an intermediate in the endogenous isoprenoid biosynthetic pathway (FIG. 3). As expected, all strains grew in the presence of 2-C-methyl-D-erythritol (ME), but only the strains harboring pMBI or pMBIS and not pMevB grew on plates supplemented with 1 mM mevalonate in the absence of ME. These results established that the synthetic MBI and MBIS operons were functional and capable of supplying IPP and DMAPP required for the growth of *E. coli*. Because the DXP pathway supplies the cells with IPP and DMAPP from a branch point, a mutation in ispC prohibits the synthesis of both pyrophosphate precursors. Although *E. coli* maintains a nonessential copy of the IPP isomerase gene on its chromosome, the expression of the gene appears to be too low to support the growth of *E. coli* when only IPP is supplied by the MevB operon.

To complete the mevalonate pathway and allow the synthesis of sesquiterpene precursors from a simple and inexpensive carbon source, the pMevT plasmid expressing the remaining three genes (atoB, HMGS and tHMGR) of the mevalonate isoprenoid pathway was co-transformed with either pMBI or pMBIS. Co-expression of the two operons, which together encode a complete pathway for the synthesis of isoprenoids from acetyl-CoA, was able to complement the ispC deletion even in the absence of mevalonate, indicating that the MevT operon was functional.

Amorphadiene Synthesis from Mevalonate

To achieve high-level production of amorphadiene and to determine if the supply of FPP to the terpene synthase was limiting amorphadiene yields, the mevalonate pathway was coupled to amorphadiene synthesis in *E. coli*. Cells harboring the ADS gene co-expressed with the MBIS bottom operon were grown in medium supplemented with exogenous mevalonate. GC-MS analysis of the culture extracts revealed that the peak amorphadiene concentration from these cultures was proportional to the amount of mevalonate added to the medium, up to a concentration of 40 mM mevalonate. These results indicated that flux from the MBIS operon did not limit amorphadiene production at the highest mevalonate concentration used. Cultures supplemented with 40 mM mevalonate produced a peak concentration of 3.4 µg caryophyllene equivalents/mL/$OD_{600}$, which is a 40- and 11-fold increase over the endogenous and engineered DXP pathway, respectively. The drop in amorphadiene concentration with time was due to the loss of the volatile terpene to the headspace, which means that these reported production values are certainly underestimated.

Severe growth inhibition was observed upon addition of greater than 10 mM mevalonate in the control cultures where the amorphadiene synthase was not expressed. To investigate the cause of this inhibition, measured the growth of E. coli DH10B from strains harboring either the pMKPMK, pMevB, pMBI or pMBIS plasmid in media supplemented with increasing concentrations of exogenous mevalonate was measured. While the addition of 5 mM mevalonate to the media inhibited the growth of cells harboring pMevB, this concentration of mevalonate did not affect the growth of cells harboring pMKPMK, pMBI or pMBIS. Expression of the operons in the absence of mevalonate or in media supplemented with 1 mM mevalonate resulted in only a slight decrease in growth. Thus, the data indicate that the accumulation of IPP, which occurs in cells with high flux through the mevalonate pathway, is toxic and inhibits normal cell growth. To compare the intracellular prenyl pyrophosphate pools in the same strains, resting cells harboring the different mevalonate operon constructs were fed radiolabeled mevalonate and the labeled metabolites were tracked. The strain expressing MevB accumulated IPP but not FPP, whereas the MBI and MBIS strains accumulated FPP but did not build up measurable levels of intracellular IPP. Simultaneous expression of the amorphadiene synthase consumed the excess FPP pool accumulated in the MBIS host, as shown by a decrease in intracellular FPP.

Because cells expressing MBIS accumulated FPP and exhibited growth inhibition in the presence of 10 mM mevalonate, it was postulated that the co-expression of the amorphadiene synthase would alleviate the growth inhibition by channeling the intracellular prenyl pyrophosphate intermediates to the volatile terpene olefin. Growth inhibition was only observed in strains lacking the ADS gene approximately 2 hours after addition of 1040 mM mevalonate and IPTG. In contrast, cells co-expressing the MBIS operon and the synthase gene both under control of IPTG-inducible promoters exhibited normal growth rates at all mevalonate concentrations. Amorphadiene production from these cultures increased proportionally with the addition of exogenous mevalonate, further supporting the conclusion that the conversion of FPP to amorphadiene plays a key role in minimizing growth inhibition. Taken together, these data strongly suggest that the engineered mevalonate pathway produces high levels of the pyrophosphate precursors. However, in the absence of the IPP isomerase, FPP synthase and terpene synthase to channel the pathway intermediates to the terpene olefin, toxic levels of intracellular pyrophosphates, especially IPP, may accumulate.

Exogenous Nucleic Acids Encoding Terpene Synthase Relieve Terpene Biosynthetic Pathway Intermediate-Induced Growth Inhibition E. coli was genetically modified to express the S. cerevisiae MEV pathway, as described above, and was grown in mevalonate-rich growth medium. Control cells were screened for growth inhibition. The cells were genetically modified with nucleic acid from an isoprenoid-producing organism. The cells produced an intermediate in the MEV pathway, which intermediate accumulated in the cell and inhibited growth of the cell. Exogenous nucleic acids were introduced into the growth-inhibited cells and were screened for relief of growth inhibition. The viable cells were then screened for terpene synthase genes. The results are shown in FIGS. 4-6.

Figure 4:
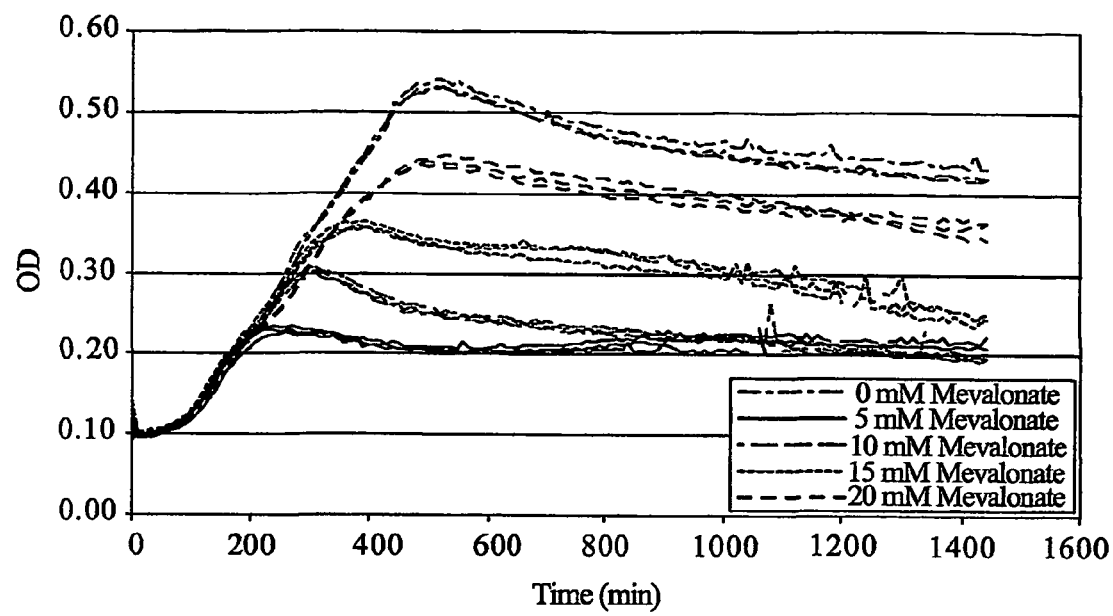
FIG. 4 depicts growth inhibition of genetically modified *Escherichia coli* (*E. coli*) cells due to overproduction of FPP.

FIG. 4. Triplicate cultures of E. coli, harboring the pTRC99A expression vector, express the genes encoding for mevalonate kinase, phosphomevalonate kinase, mevalonate diphosphate decarboxylase, IPP isomerase, and FPP synthase from the pBBR1MCS-2 plasmid with varying concentrations of mevalonate present in the culture medium.

Figure 5:
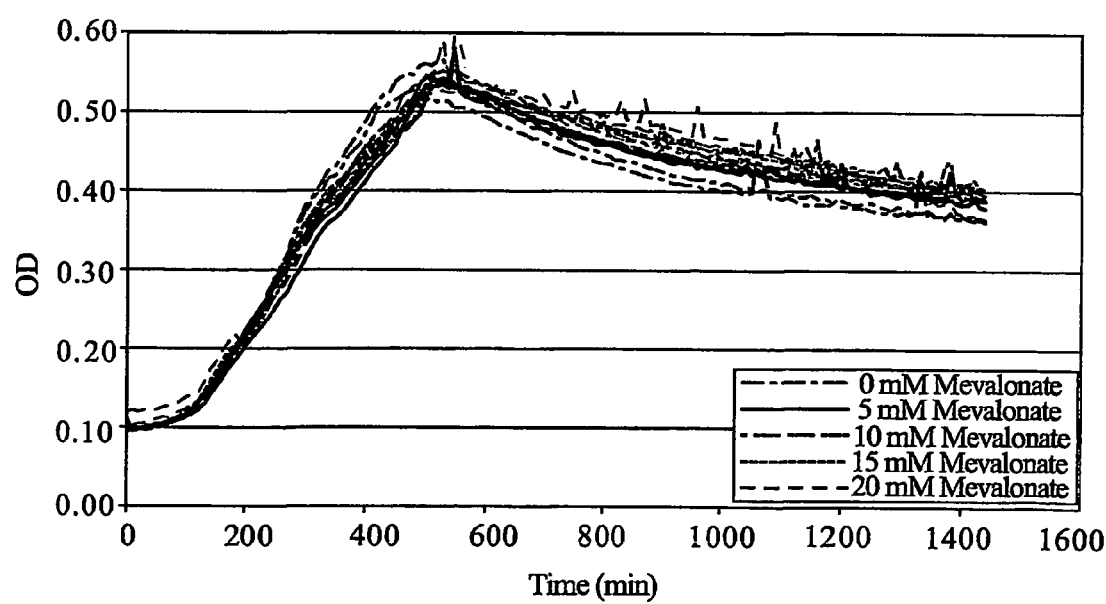
FIG. 5 depicts relief of growth inhibition of genetically modified *E. coli* at all concentrations of mevalonate as a result of the presence of a sesquiterpene synthase gene.

FIG. 5. Triplicate cultures of E. coli harboring the pTRCADS expression vector, a pTRC99A backbone containing the gene for amorphadiene synthase, which converts FPP to the sesquiterpene amorphadiene.

Figure 6:
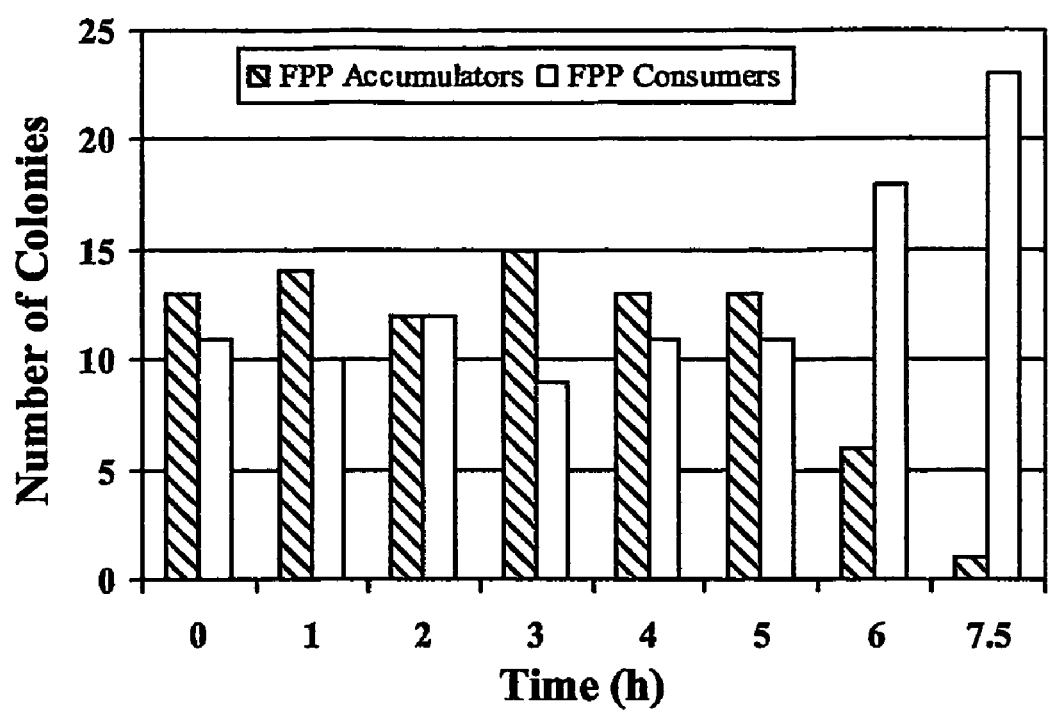
FIG. 6 depicts enrichment for bacteria capable of consuming FPP in a mixed population.

FIG. 6. A mixed population of E. coli is initially equally represented by bacteria capable of converting FPP to amorphadiene and those incapable of converting FPP to amorphadiene. Both populations of bacteria are equally capable of converting the mevalonate present in the culture medium to FPP.

Example 2

Identifying Terpene Synthase Gene Activity Exogenous Nucleic Acids

E. coli is genetically modified, e.g., as described in Example 1, to express MEV pathway enzymes MK, PMK, MPD, and IDI under the control of an inducible promoter. Control genetically modified cells are grown in mevalonate-rich growth medium, and monitored for growth inhibition, which may be accompanied by cell death, mutation of cellular DNA, or entry of the cell into a quiescent state. Test genetically modified cells are transformed with exogenous nucleic acids that may include nucleotide sequences encoding terpene biosynthetic pathway genes, including, e.g., terpene synthases, and enzymes downstream from a terpene synthase. The exogenous nucleic acid is a cDNA library generated from mRNA isolated from cells of a unicellular organism; a cDNA library generated from mRNA isolated from cells of a multicellular organism; a cDNA library generated from mRNA isolated from cells of a plant that has been wounded, infected with an insect, infected with an arachnid, subjected to water deprivation, or subjected to another type of stress; a library of synthetic terpene synthase-encoding nucleic acids; etc. Expression of the MEV pathway genes in the transformed test cells is induced by adding inducer (e.g., IPTG) to the culture medium. The transformed test cells are then grown in medium containing mevalonate, and screened for relief of growth inhibition. For example, the effect of the exogenous nucleic acid on the ability of the test host cells to survive the toxic terpene biosynthetic pathway intermediate is determined by identifying survivors. The viable cells are then screened for terpene synthase gene activity.

Example 3

Increasing Production of Prenyl Diphosphates in Genetically Modified E. coli Cells E. coli is genetically modified, e.g., as described in Example 1, to express MEV pathway enzymes MK, PMK, MPD, IDI, and FPP synthase under the control of an inducible promoter. Inducer (e.g., IPTG) and mevalonate are added to the growth medium, and cells are then screened for growth inhibition. Cells are plated on LB-agar plates at various times following addition of the inducer and mevalonate. Cells that form small colonies are further analyzed for the production of MEV pathway gene products that have increased catalytic activity.

Example 4

Isolation of a Nucleic Acid Encoding a Terpene Biosynthetic Pathway Intermediate-Modifying Gene Product from a Library of *Bacillus subtilis* 6051 Genomic DNA A genomic library from the isoprene-producing bacteria *Bacillus subtilis* 6051 was expressed from the pTrc99A plasmid in an *E. coli* strain engineered (genetically modified) to produce elevated levels of IPP and DMAPP. The engineered screening strain expressed nucleic acids encoding mevalonate kinase, phosphomevalonate kinase, mevalonate diphosphate decarboxylase, and IPP/DMAPP isomerase from the pBBR1MCS plasmid, as described in Example 1. Mevalonate was present in the growth medium at a concentration of 10 mM. After several rounds of growth, only plasmids containing genomic fragments with either yhfR or nudF were found in the genomic library. The data are shown in FIG. 7-9.

Figure 7:
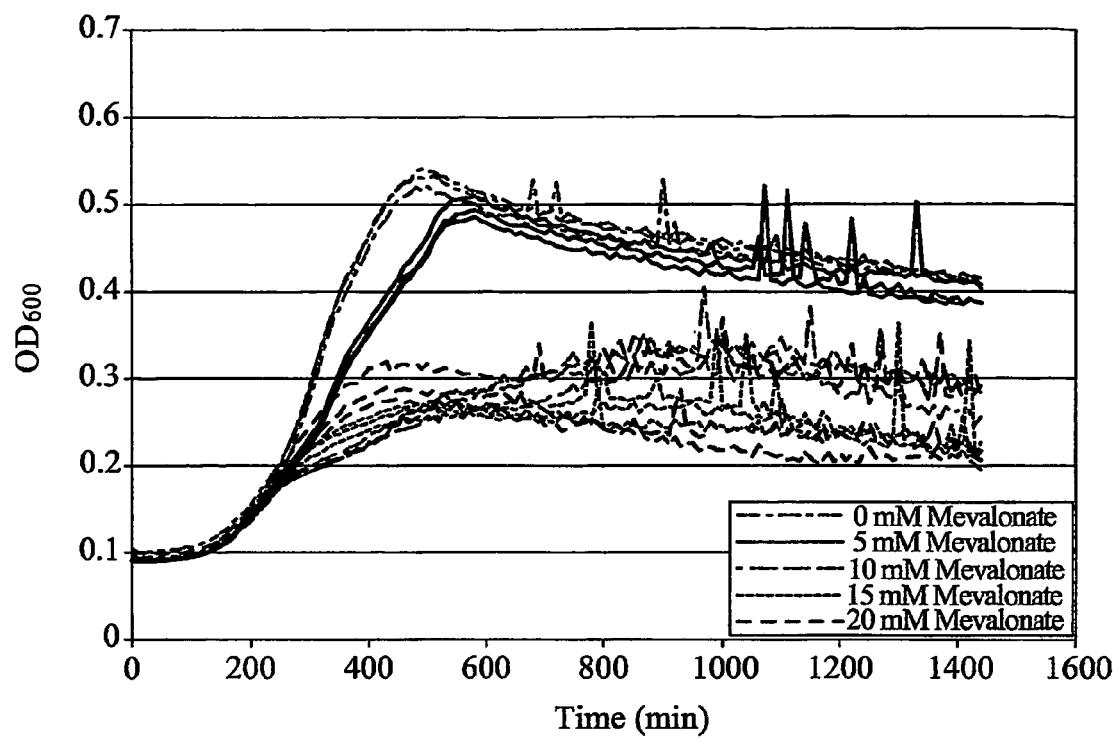
FIG. 7 depicts growth inhibition due to the overproduction of IPP and DMAPP.

FIG. 7. Growth inhibition due to the overproduction of IPP and DMAPP. Triplicate cultures of *E. coli* expressing the genes encoding for mevalonate kinase, phosphomevalonate kinase, mevalonate diphosphate decarboxylase, and IPP isomerase from the pBBR1MCS-2 plasmid were grown in the presence of various concentrations of mevalonate present in the culture medium. The cells also harbor the pTRC99A expression vector.

Figure 8:
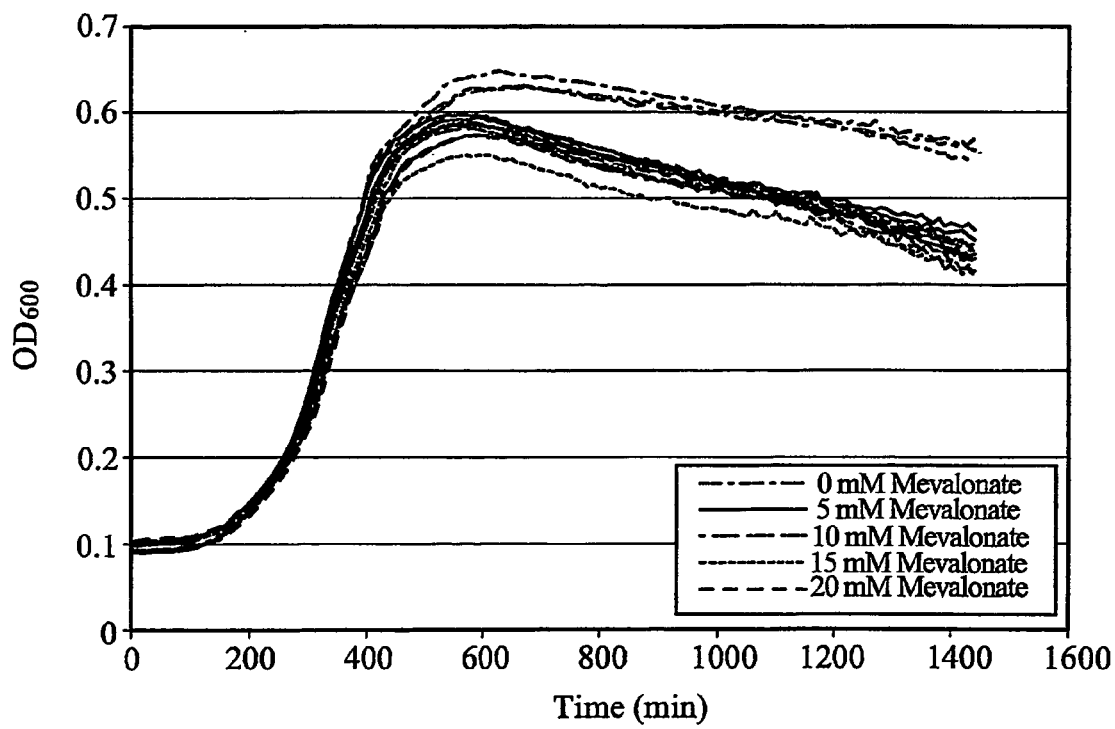
FIG. 8 depicts relief of growth inhibition by expression of yhfR.

FIG. 8. Relief of growth inhibition by expression of yhfR. Triplicate cultures were set up, which were identical to those depicted in FIG. 7, except that pTRC99A was replaced by pYhfR. The pYhfR plasmid is a pTrc99A backbone that contains the gene yhfR. The yhfR gene was isolated from a plasmid library containing genomic DNA from *Bacillus subtilis* 6051. No growth inhibition was observed in this system for all concentrations of mevalonate studied.

Figure 9:
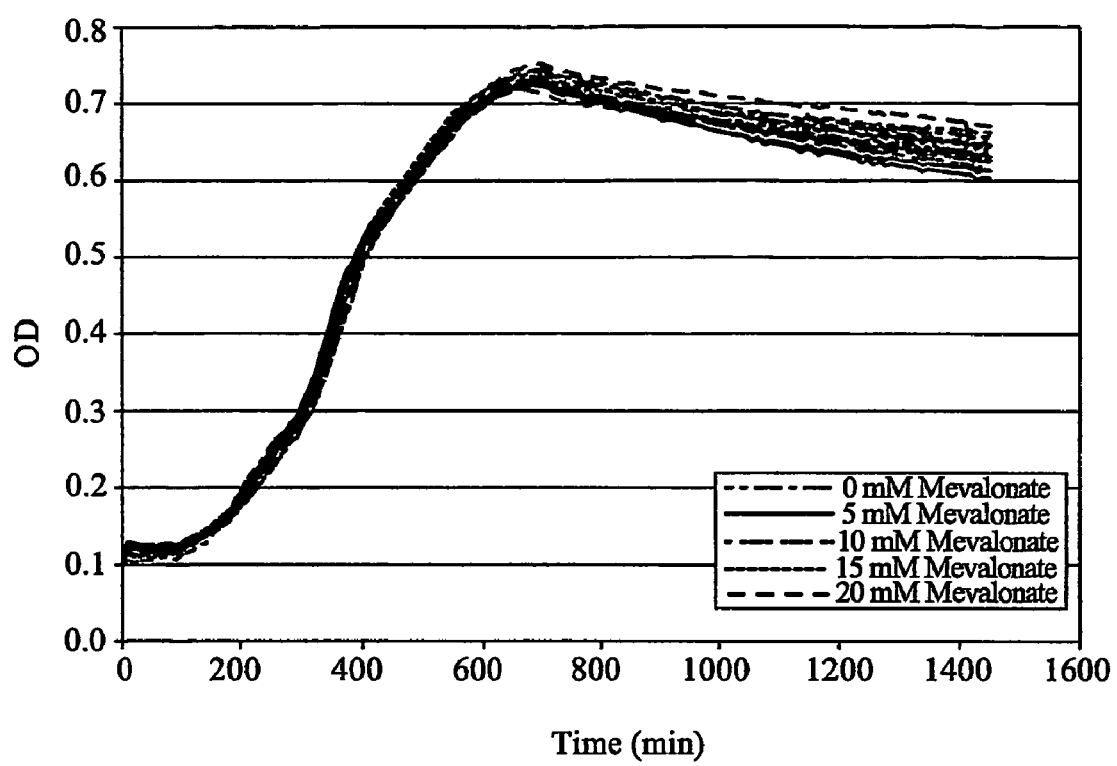
FIG. 9 depicts relief of growth inhibition by expression of nudF.

FIG. 9. Relief of growth inhibition by expression of nudF. Triplicate cultures were set up, which were identical to those in FIG. 7, except that pTRC99A was replaced by pC9b. The pC9b plasmid is a pTrc99A backbone that contains the gene nudF. The nudF gene was isolated from a plasmid library containing genomic DNA from *Bacillus subtilis* 6051. No growth inhibition was observed in this system for all concentrations of mevalonate studied.

Example 5

Identifying a Mevalonate Isoprenoid Pathway Gene with Increased Expression and/or Activity

*E. coli* is engineered to express a portion of the *S. cerevisiae* MEV pathway that produces a toxic intermediate. Control cells producing this toxic intermediate are screened for growth inhibition, which may be by either cell death or mutation. The cells are transformed with a gene or multiple genes that use the toxic intermediate as a substrate and are screened for relief of growth inhibition. The viable cells are then screened for improved expression and/or activity of the transformed gene.

As a specific example, the accumulation of hydroxymethylglutaryl-CoA (HMG-CoA) is toxic to engineered *E. coli*. As demonstrated in FIG. 10 and FIG. 11, expression of *S. cerevisiae* HMG-CoA synthase from plasmid pHMGS in engineered *E. coli* leads to the accumulation of HMG-CoA and growth inhibition of *E. coli*. Introduction of a second plasmid (pHMGR) expressing HMG-CoA reductase into the engineered strain of *E. coli* eliminates HMG-CoA accumulation and relieves growth inhibition (see FIGS. 10 and 11).

Figure 10:
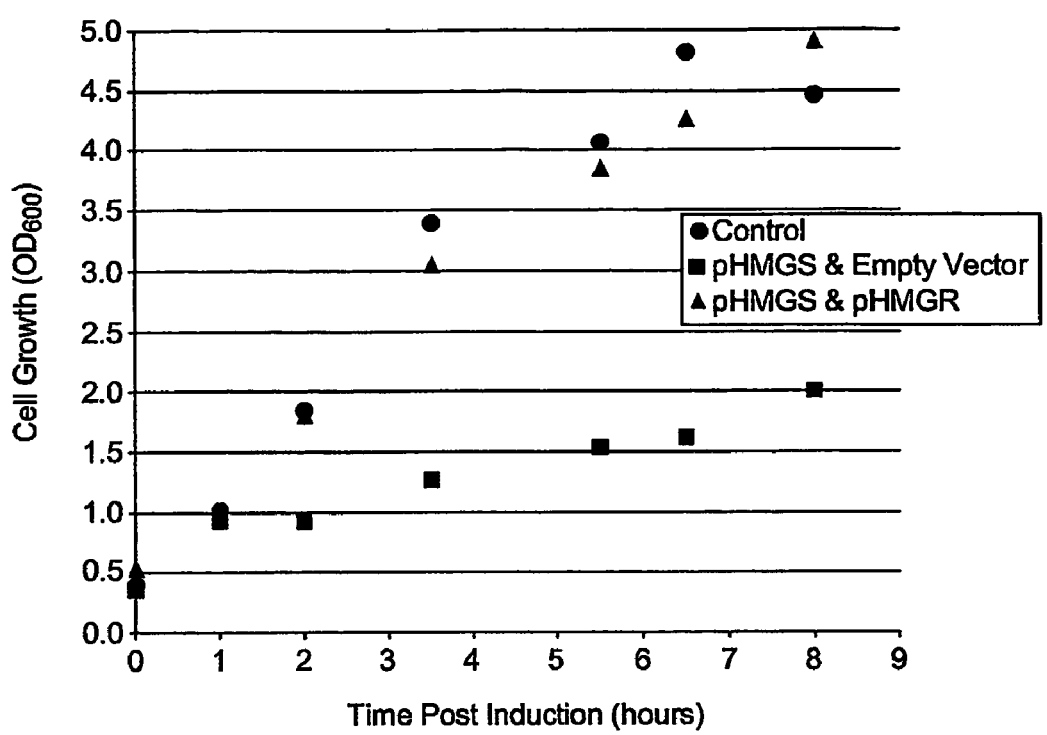
FIG. 10 is a graph depicting relief of growth inhibition of *E. coli* caused by HMG-CoA accumulation by co-expression of *S. cerevisiae* HMG-CoA reductase.

FIG. 10. Cultures of *E. coli* expressing either no heterologous genes (Control), the *S. cerevisiae* HMG-CoA synthase alone (pHMGS & Empty Vector), or both the *S. cerevisiae* HMG-CoA synthase and HMG-CoA reductase (pHMGS & pHMGR) on separate expression vectors. Expression of HMG-CoA synthase alone inhibited cell growth of *E. coli*, while the additional expression of HMG-CoA reductase relieved the growth inhibition.

Figure 11:
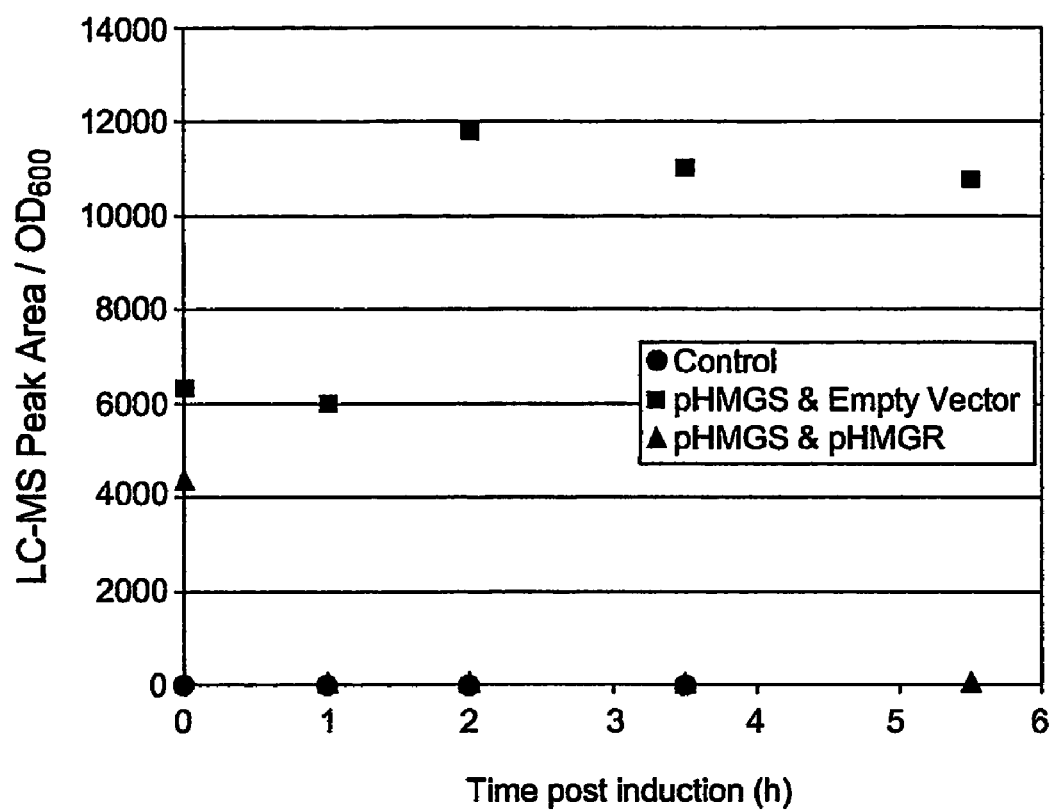
FIG. 11 is a graph depicting the effect of co-expression of *S. cerevisiae* HMG-CoA reductase on growth inhibition by the terpene biosynthesis pathway intermediate HMG-CoA.

FIG. 11. Metabolite analysis of cultures of *E. coli* expressing either no heterologous genes (Control), the *S. cerevisiae* HMG-CoA synthase alone (pHMGS and Empty Vector), or both the *S. cerevisiae* HMG-CoA synthase and HMG-CoA reductase (pHMGS and pHMGR) on separate expression vectors. *E. coli* expressing HMG-CoA synthase alone accumulated HMG-CoA. *E. coli* expressing both HMG-CoA reductase and HMG-CoA synthase did not accumulate HMG-CoA over time.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of identifying a gene product having activity in a terpene biosynthetic pathway, the method comprising:
 a) producing a test cell by introducing into a genetically modified host cell an exogenous nucleic acid comprising a nucleotide sequence encoding a candidate gene product, wherein the genetically modified host cell is genetically modified with one or more nucleic acids that comprise nucleotide sequences encoding one or more of acetoacetyl-CoA thiolase, hydroxymethylglutaryl-CoA synthase, hydroxymethylglutaryl-CoA reductase, mevalonate kinase, phosphomevalonate kinase, and mevalonate pyrophosphate decarboxylase, wherein said genetic modification results in production of a prenyl diphosphate intermediate in an amount effective to inhibit growth of the genetically modified host cell; and
 b) determining the effect, if any, of expression of the candidate gene product on growth of the test cell, wherein a reduction in growth inhibition indicates the candidate gene product has activity in the terpene biosynthetic pathway.

2. The method of claim 1, wherein the exogenous nucleic acid is isolated from a cell of a species that is different from the genetically modified host cell.

3. The method of claim 2, wherein the exogenous nucleic acid is isolated from a eukaryotic cell or a prokaryotic cell.

4. The method of claim 2, wherein the exogenous nucleic acid is isolated from a cell of an organism selected from a protozoan, a plant, a fungus, an algae, a yeast, a reptile, an amphibian, a mammal, a marine microorganism, a marine invertebrate, an arthropod, an isopod, an insect, an arachnid, an archaebacterium, and a eubacterium.

5. The method of claim 4, wherein the genome of the organism is mutated prior to isolation of nucleic acid from the organism.

6. The method of claim 1, wherein the exogenous nucleic acid is a cDNA.

7. The method of claim 1, wherein the exogenous nucleic acid is genomic DNA.

8. The method of claim 1, wherein the exogenous nucleic acid is synthetic DNA.

9. The method of claim 8, wherein the synthetic DNA is amplified using a polymerase chain reaction.

10. The method of claim 1, wherein the genetically modified host cell is a prokaryotic cell.

11. The method of claim 10, wherein the prokaryotic cell is *Escherichia coli*.

12. The method of claim 1, wherein the genetically modified host cell is a eukaryotic cell.

13. The method of claim 12, wherein the eukaryotic cell is a yeast cell.

14. The method of claim 13, wherein the yeast cell is *Saccharomyces cerevisiae*.

15. The method of claim 1, further comprising isolating the exogenous nucleic acid from the test cell.

16. The method of claim 1, further comprising separating growth-inhibited test cells from test cells that exhibit a reduction in growth inhibition by buoyant density separation; and isolating the exogenous nucleic acid from the test cells that exhibit reduced growth inhibition.

17. The method of claim 1, wherein the genetically modified host cell is further genetically modified with a nucleic acid comprising a nucleotide sequence encoding an isopentenyl pyrophosphate isomerase.

18. The method of claim 1, wherein the genetically modified host cell is further genetically modified with a nucleic acid comprising a nucleotide sequence encoding a prenyl transferase.

19. The method of claim 1, wherein the prenyl diphosphate is a monoprenyl diphosphate.

20. The method of claim 1, wherein the prenyl diphosphate is a polyprenyl diphosphate.

21. The method of claim 20, wherein the polyprenyl diphosphate is selected from geranyl diphosphate, farnesyl diphosphate, geranylgeranyl diphosphate, geranylfarnesyl diphosphate, hexaprenyl diphosphate, heptaprenyl diphosphate, octaprenyl diphosphate, solanesyl diphosphate, and decaprenyl diphosphate.

22. The method of claim 1, wherein the determining step is by monitoring optical density of a liquid culture comprising the test cell, or by identifying a viable test cell.

23. A method of identifying a gene product having activity in a terpene biosynthetic pathway, the method comprising:
   a) producing a test cell by introducing into a genetically modified host cell an exogenous nucleic acid comprising a nucleotide sequence encoding a candidate gene product, wherein the genetically modified host cell is genetically modified with one or more nucleic acids comprising nucleotide sequence encoding mevalonate kinase, phosphomevalonate kinase, and mevalonate pyrophosphate decarboxylase, wherein the genetically modified host cell is cultured in the presence of mevalonate, and wherein said genetic modification results in production of a prenyl diphosphate intermediate in an amount effective to inhibit growth of the genetically modified host cell; and
   b) determining the effect, if any, of expression of the candidate gene product on growth of the test cell, wherein a reduction in growth inhibition indicates the candidate gene product has activity in the terpene biosynthetic pathway.

24. The method of claim 23, wherein the genetically modified host cell is further genetically modified with a nucleic acid comprising a nucleotide sequence encoding an isopentenyl pyrophosphate isomerase.

25. The method of claim 23, wherein the genetically modified host cell is further genetically modified with a nucleic acid comprising a nucleotide sequence encoding a prenyl transferase.

26. The method of claim 23, wherein the exogenous nucleic acid is isolated from a cell of a species that is different from the genetically modified host cell.

27. The method of claim 23, wherein the exogenous nucleic acid is isolated from a eukaryotic cell or a prokaryotic cell.

28. The method of claim 23, wherein the exogenous nucleic acid is isolated from a cell of an organism selected from a protozoan, a plant, a fungus, an algae, a yeast, a reptile, an amphibian, a mammal, a marine microorganism, a marine invertebrate, an arthropod, an isopod, an insect, an arachnid, an archaebacterium, and a eubacterium.

29. The method of claim 28, wherein the genome of the organism is mutated prior to isolation of nucleic acid from the organism.

30. The method of claim 23, wherein the exogenous nucleic acid is a cDNA, a genomic DNA, or a synthetic DNA.

31. The method of claim 23, wherein the genetically modified host cell is a prokaryotic cell.

32. The method of claim 31, wherein prokaryotic cell is *Escherichia coli*.

33. The method of claim 23, wherein the genetically modified host cell is a eukaryotic cell.

34. The method of claim 33, wherein the eukaryotic cell is a yeast cell.

35. The method of claim 23, further comprising isolating the exogenous nucleic acid from the test cell.

36. The method of claim 23, further comprising separating growth-inhibited test cells from test cells that exhibit a reduction in growth inhibition by buoyant density separation; and isolating the exogenous nucleic acid from the test cells that exhibit reduced growth inhibition.

37. The method of claim 23, wherein the prenyl diphosphate is a monoprenyl diphosphate or a polyprenyl diphosphate.

38. The method of claim 37, wherein the polyprenyl diphosphate is selected from geranyl diphosphate, farnesyl diphosphate, geranylgeranyl diphosphate, geranylfarnesyl diphosphate, hexaprenyl diphosphate, heptaprenyl diphosphate, octaprenyl diphosphate, solanesyl diphosphate, and decaprenyl diphosphate.

39. The method of claim 23, wherein the determining step is by monitoring optical density of a liquid culture comprising the test cell, or by identifying a viable test cell.

40. A method of identifying a gene product having activity in a terpene biosynthetic pathway, the method comprising:
   a) producing a test cell by introducing into a genetically modified host cell an exogenous nucleic acid comprising a nucleotide sequence encoding a candidate gene product, wherein the genetically modified host cell is genetically modified with one or more nucleic acids comprising nucleotide sequences encoding 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, 1-hydroxy-2-methyl-2-(E)-butenyl 4-diphosphate synthase, and isopentenyl/dimethylallyl diphosphate synthase, and wherein said genetic modification results in production of a prenyl diphosphate intermediate in an amount effective to inhibit growth of the genetically modified host cell; and
   b) determining the effect, if any, of expression of the candidate gene product on growth of the test cell, wherein a reduction in growth inhibition indicates the candidate gene product has activity in the terpene biosynthetic pathway.

41. The method of claim 40, wherein the test cell is grown in the presence of methylerithritol.

42. The method of claim 40, wherein the genetically modified host cell is further genetically modified with one or more nucleic acids comprising nucleotide sequences encoding 1-deoxy-D-xylulose-5-phosphate synthase, and 1-deoxy-D-xylulose-5-phosphate reductoisomerase.

43. The method of claim 40, wherein the exogenous nucleic acid is isolated from a cell of a species that is different from the genetically modified host cell.

44. The method of claim 40, wherein the exogenous nucleic acid is isolated from a eukaryotic cell or a prokaryotic cell.

45. The method of claim 40, wherein the exogenous nucleic acid is isolated from a cell of an organism selected from a protozoan, a plant, a fungus, an algae, a yeast, a reptile, an amphibian, a mammal, a marine microorganism, a marine invertebrate, an arthropod, an isopod, an insect, an arachnid, an archaebacterium, and a eubacterium.

46. The method of claim 45, wherein the genome of the organism is mutated prior to isolation of nucleic acid from the organism.

47. The method of claim 40, wherein the exogenous nucleic acid is a cDNA, a genomic DNA, or a synthetic DNA.

48. The method of claim 40, wherein the genetically modified host cell is a prokaryotic cell.

49. The method of claim 48, wherein prokaryotic cell is *Escherichia coli*.

50. The method of claim 40, wherein the genetically modified host cell is a eukaryotic cell.

51. The method of claim 50, wherein the eukaryotic cell is a yeast cell.

52. The method of claim 40, further comprising isolating the exogenous nucleic acid from the test cell.

53. The method of claim 40, further comprising separating growth-inhibited test cells from test cells that exhibit a reduction in growth inhibition by buoyant density separation; and isolating the exogenous nucleic acid from the test cells that exhibit reduced growth inhibition.

54. The method of claim 40, wherein the prenyl diphosphate is a monoprenyl diphosphate or a polyprenyl diphosphate.

55. The method of claim 54, wherein the polyprenyl diphosphate is selected from geranyl diphosphate, farnesyl diphosphate, geranylgeranyl diphosphate, geranylfarnesyl diphosphate, hexaprenyl diphosphate, heptaprenyl diphosphate, octaprenyl diphosphate, solanesyl diphosphate, and decaprenyl diphosphate.

56. The method of claim 40, wherein the determining step is by monitoring optical density of a liquid culture comprising the test cell, or by identifying a viable test cell.

* * * * *